United States Patent
Hendricks et al.

(10) Patent No.: US 12,351,878 B2
(45) Date of Patent: Jul. 8, 2025

(54) IDENTIFICATION OF HER2 MUTATIONS IN LUNG CANCER AND METHODS OF TREATMENT

(71) Applicants: THE TRANSLATIONAL GENOMICS RESEARCH INSTITUTE, Phoenix, AZ (US); OHIO STATE UNIVERSITY, Columbus, OH (US)

(72) Inventors: William Hendricks, Phoenix, AZ (US); Muhammed Murtaza, Phoenix, AZ (US); Gwendolen Lorch, Columbus, OH (US)

(73) Assignees: THE TRANSLATIONAL GENOMICS RESEARCH INSTITUTE, Phoenix, AZ (US); OHIO STATE UNIVERSITY, Columbus, OH (US)

( * ) Notice: Subject to any disclaimer, the term of this patent is extended or adjusted under 35 U.S.C. 154(b) by 1042 days.

(21) Appl. No.: 17/413,488

(22) PCT Filed: Dec. 11, 2019

(86) PCT No.: PCT/US2019/065715
§ 371 (c)(1),
(2) Date: Jun. 11, 2021

(87) PCT Pub. No.: WO2020/123642
PCT Pub. Date: Jun. 18, 2020

(65) Prior Publication Data
US 2022/0056535 A1    Feb. 24, 2022

Related U.S. Application Data

(60) Provisional application No. 62/778,282, filed on Dec. 11, 2018.

(51) Int. Cl.
*C12Q 1/6886* (2018.01)
*A61K 45/06* (2006.01)

(52) U.S. Cl.
CPC ............ *C12Q 1/6886* (2013.01); *A61K 45/06* (2013.01); *C12Q 2600/156* (2013.01); *C12Q 2600/158* (2013.01)

(58) Field of Classification Search
CPC .................................................... C12Q 1/6886
See application file for complete search history.

(56) References Cited

FOREIGN PATENT DOCUMENTS

WO    WO-2018200505 A1 * 11/2018 ......... A61K 31/4709

OTHER PUBLICATIONS

Mariotti, E et al. Canine pulmonary adenocarcinoma tyrosine kinase receptor expression and phosphorylation. 2014. BMC Vet Research 10:19,1-13. (Year: 2014).*
Yamamto, Hiromasa et al., "Novel Germline Mutation in the Transmembrane Domain of HER2 in Familial Lung Adenocarcinomas", Journal of the National Cancer Institute, 106(1), pp. 1-4 (Dec. 7, 2013).

* cited by examiner

*Primary Examiner* — Samuel C Woolwine
*Assistant Examiner* — Lisa Horth
(74) *Attorney, Agent, or Firm* — FULLER IP LAW LLC; Rodney J. Fuller

(57) ABSTRACT

Methods are provided for treating lung cancer, and more particularly for treating pulmonary adenocarcinoma in a canine subject. The method may comprise assaying a biological sample from the canine subject, such as a tumor sample or a plasma sample, for a mutation in the HER2 gene. The mutation may include HER2 V659E, HER2 A664T, or HER2 K676E. If one or more of the mutations is present in the biological sample, the methods further include treating the canine subject by administering a therapeutically effective amount of an inhibitor of HER2. For example, a HER2 V659E may indicate increase sensitivity to a HER2 inhibitor. The HER2 inhibitor may include a small molecule HER2 inhibitor, such as trastuzumab, neratinib, lapatinib, erlotinib, and pertuzumab.

18 Claims, 72 Drawing Sheets

Specification includes a Sequence Listing.

Supplementary Table 1. Informatic tools utilized in primary canine lung cancer analysis

| Sequencing Platform | Tool | Version | Flags | Flag Purpose and/or Parameters where Applicable |
|---|---|---|---|---|
| Exome | BWA | 0.7.8 | -R "${RGTAG}" | RGTAGs consists of the flowcell ID, lane number and the library tag ID specific for every library prep and assay type |
| | | | -M | |
| | | | -t | 8 |
| | GATK- Recalibrate | 3.3.0 | -nct | 8 |
| | | | --disable_indel_quals | |
| | | | -knownsites | Known SNPs from dbSNP |
| | | | -cov | QualityScoreCovariate |
| | | | -cov | ReadGroupCovariate |
| | | | -cov | CycleCovariate |
| | | | -cov | ContextCovariate |
| | GATK- MarkDups | 3.3.0 | ASSUME_SORTED | TRUE |
| | | | REMOVE_DUPLICATES | FALSE |
| | | | MAX_RECORDS_IN_RAM | 18000000 |
| | | | CREATE_INDEX | TRUE |
| | | | VALIDATION_STRINGENCY | SILENT |
| | GATK - RealignerTargetCreator | 3.3.0 | -nt | 16 |
| | | | --maxIntervalSize | 350 |
| | | | -DBQ | 1 |
| | GATK--IndelRealigner | 3.3.0 | -DBQ | 1 |
| | | | --maxReadsInMemory | 5000000 |
| | | | --maxConsensuses | 24 |
| | | | --maxReadsForConsensuses | 80 |
| | | | --maxReadsForRealignment | 12000 |
| | | | -model | KNOWNS_ONLY |
| | | | -known | Known INDELs from dbSNP |
| | GATK -HaploTypeCaller | 3.3.0 | -nct | 8 |
| | | | -D | KNOWN |

FIG. 7A

| Sequencing Platform | Tool | Version | Flags | Flag Purpose and/or Parameters where Applicable |
|---|---|---|---|---|
| | Samtools-mpileup | 1.2 | --mbq | 10 |
| | | | -DSS0G | |
| | | | -C | 50 |
| | | | -F | 0.01 |
| | | | -vmO | v |
| | Freebayes | | --ploidy | 2 |
| | | | --min-repeat-entropy | 1 |
| | Seurat | 2.6 | --both_strands | |
| | | | --metrics | |
| | | | --indels | |
| | | | --allele-metrics | |
| | MuTect | 1.1.4 | --cosmic | cosmicVCF |
| | | | --dbsnp | dbSNP variants |
| | | | --fraction_contamination | 0.02 |
| | | | --minimum_mutation_cell_fraction | 0 |
| | | | --minimum_normal_allele_fraction | 0 |
| | | | --min_qscore | 5 |
| | | | --gap_events_threshold | 3 |
| | | | --heavily_clipped_read_fraction | 0.3 |
| | | | --required_maximum_alt_allele_mapping_quality_score | 20 |
| | | | --max_alt_alleles_in_normal_count | 2 |
| | | | --max_alt_alleles_in_normal_qscore_sum | 20 |
| | | | --max_alt_alleles_in_normal_fraction | 0.03 |
| | Picard - MultiMetrics | 1.128 | PROGRAM | CollectInsertSizeMetrics |
| | | | PROGRAM | CollectAlignmentSummaryMetrics |
| | | | PROGRAM | QualityScoreDistribution |
| | | | PROGRAM | MeanQualityByCycle |
| | | | ASSUME_SORTED | TRUE |

FIG. 7B

| Sequencing Platform | Tool | Version | Flags | Flag Purpose and/or Parameters where Applicable |
|---|---|---|---|---|
| | STAR | 2.4 | --limitOutSAMoneReadBytes | 90000000 |
| | | | --readFilesCommand | zcat |
| | | | --outFilterType | BySJout |
| | | | --outFilterMultimapNmax | 10 |
| | | | --outFilterMismatchNmax | 10 |
| | | | --outFilterMismatchNoverLmax | 0.1 |
| | | | --alignIntronMin | 20 |
| | | | --alignIntronMax | 1000000 |
| | | | --alignMatesGapMax | 1000000 |
| | | | --alignSJoverhangMin | 8 |
| | | | --alignSJDBoverhangMin | 8 |
| | | | --seedSearchStartLmax | 30 |
| | | | --chimSegmentMin | 15 |
| | | | --chimJunctionOverhangMin | 15 |
| | | | --runThreadn | 14 |
| | | | --genomeLoad | NoSharedMemory |
| | | | --outSAMstrandField | intronMotif |
| | | | --outSAMunmapped | Within |
| | | | --outSAMmapqUnique | 255 |
| | | | --outSAMattrRGline | $Rgtags |
| | | | --outSAMmode | Full |
| | tConut | | Default | |
| | delly-0.7.6 | | -q | 20 |
| Amplicon | picardtools | 2.10.3 | | |
| | FastQC | v0.11.5 | | |
| | EA utils | 1.1.2 | | |
| | samtools - view, index, sort, mpileup | 1.2 | | |

FIG. 7C

Supplementary Table 2. Extended clinical and multiplatform annotation of primary canine lung cancer cases.

Signalment and history

| Patient ID | Breed | Sex | Neutered/Spayed | Age at diagnosis (yr) | Clinical finding |
|---|---|---|---|---|---|
| CCB010381 | Labrador Retriever mix | Female | Yes | 10 | ND |
| CCB040231 | Poodle | Female | Yes | 13 | ND |
| CCB050342 | Flat-Coated Retriever | Female | Yes | 11 | Decreased energy level |
| OSU396622 | Schnauzer (Miniature) | Male | Yes | 12 | Incidental |
| CCB010109 | Labrador Retriever | Male | Yes | 11 | Cough |
| OSU361939 | Cocker Spaniel | Female | Yes | 13 | Cough, shaking, anorexia |
| CCB030383 | Labrador Retriever | Female | Yes | 10 | Incidental |
| CCB050097 | Schipperke | Female | Yes | 12 | Cough |
| CCB060156 | Great Dane | Male | No | 7 | ND |
| OSU428073 | Boston Terrier | Male | Yes | 11 | Cough |
| CCB050345 | Mixed Breed | Female | Yes | 11 | Seizures |
| CCB050350 | Norwegian Elkhound | Female | Yes | 15 | Incidental |
| OSU388285 | Basset Hound | Female | Yes | 9 | Lethary, pyrexia, cough |
| CCB040245 | Mixed Breed | Male | Yes | 13 | ND |
| CCB040385 | Australian Shepherd | Male | Yes | 9 | ND |
| OSU424354 | West Highland White Terrier | Male | Yes | 8 | Cough, respiratory ffort, no apetite |
| CCB010387 | Labrador Retriever | female | Yes | 13 | ND |
| OSU389339 | Basset Hound | Female | Yes | 9 | Cough |
| OSUK9PAPADO | Schnauzer (Miniature) | Male | Yes | 10 | Dyspnea |
| CCB050354 | Labrador Retriever | Male | No | 9 | Cough, exercise intolerance |
| OSUK9PAPADRe | Mixed Breed | Male | Yes | 9 | Hemoptysis |
| OSU419040 | Pomeranian | Female | Yes | 13 | Wheezing, collapse after exercise |
| CCB030381 | Labrador Retriever | Female | Yes | 12 | Cough |
| CCB060143 | Mixed Breed | Male | Yes | 11 | ND |

FIG. 8A

| Signalment and history | | | Neutered/ | Age at | |
|---|---|---|---|---|---|
| Patient ID | Breed | Sex | Spayed | diagnosis (yr) | Clinical finding |
| CCB070294 | Mixed Breed | Female | Yes | 9 | Lethargy |
| CCB050356 | Brittany Spaniel | Female | Yes | 11 | Cough |
| CLAC | Pointer | Male | No | 10 | ND |
| OSU429271 | Wheaten Terrier | Female | Yes | 9 | Incidental |
| CCB070214 | Mixed Breed | Female | Yes | 8 | ND |
| CCB070142 | Mixed Breed | Female | Yes | 12 | ND |
| CCB050081 | Weimaraner | Female | Yes | 12 | Incidental |
| OSU431895 | Lhasa Apso | Female | Yes | 13 | Cough |
| OSUK9PADSn | Shih Tzu | Male | Yes | 12 | Incidental |
| CCB050363 | Boxer | Male | Yes | 7 | Incidental |
| CCB020198 | Boxer | Male | Yes | 8 | Collapse, thoracic pain |
| CCB040005 | Labrador Retriever | Male | Yes | 10 | ND |
| OSUK9PADSQ | Mixed Breed | Female | Yes | 11 | Hemoptysis |
| CCB050243 | Shih Tzu | Female | Yes | 8 | ND |
| OSU381645 | German Shepherd | Male | Yes | 11 | Incidental |
| CCB050352 | Mixed Breed | Female | Yes | 12 | ND |
| OSU415281 | Mixed Breed | Male | Yes | 12 | Incidental |
| OSU422557 | Mixed Breed | Male | Yes | 14 | Weight loss |
| BACA | ND | ND | ND | ND | ND |
| CCB030382 | Bichon Frise | Female | Yes | 12 | Cough |
| CCB070152 | Mixed Breed | Male | Yes | 10 | ND |
| CCB050346 | Mixed Breed | Female | Yes | 10 | Cough after exercise |
| CCB020070 | Labrador Retriever | Female | Yes | 12 | Cough |
| CCB050200 | Mixed Breed | Male | Yes | 10 | ND |
| CCB020203 | Scottish Terrier | Male | Yes | 8 | Wheezing, cough, dyspnea |
| CCB060040 | Welsh Corgi, Pembroke | Male | Yes | 14 | ND |
| CCB060056 | Papillon | Female | Yes | 12 | ND |

FIG. 8B

| Signalment and history | | | | | |
|---|---|---|---|---|---|
| Patient ID | Breed | Sex | Neutered/Spayed | Age at diagnosis (yr) | Clinical finding |
| CCB040149 | Labrador Retriever | Male | Yes | 13 | ND |
| CCB010227 | Australian Shepherd | Female | Yes | 11 | Cough |
| CCB070114 | Bichon Frise | Female | Yes | 14 | ND |
| CCB070295 | Mixed Breed | Female | Yes | 12 | ND |
| CCB060157 | Golden Retriever | Male | Yes | 9 | ND |
| OSUK9PAPADSh | Dachshund | Female | Yes | 10 | Cough |
| CCB070006 | Labrador Retriever | Female | Yes | 13 | ND |
| CCB070296 | Bichon Frise | Female | Yes | 11 | ND |
| OSUK9PAPADI | Labrador Retriever mix | Female | Yes | 6 | Incidental |
| OSU421496 | American Bulldog | Male | No | 7 | Dyspnea |
| OSUK9PADBa | Golden Retriever | Male | Yes | 13 | Cough |
| CCB020251 | Border Collie | Male | Yes | 12 | Cough, dyspnea |
| CCB040011 | Weimaraner | Female | Yes | 12 | ND |
| CCB010336 | Mixed Breed | Male | Yes | 11 | ND |
| CCB050348 | Rat Terrier | Male | Yes | 10 | ND |
| CCB010105 | Shih Tzu | Male | Yes | 10 | Cough |
| CCB010131 | Bichon frise | Female | Yes | 11 | ND |
| CCB010262 | Mixed Breed | Male | Yes | 11 | ND |
| CCB010379 | Keeshound | Male | Yes | 13 | ND |
| CCB020051 | Schnauzer (Miniature) | Male | Yes | 12 | Hemoptysis |
| CCB020245 | Labrador Retriever | Male | Yes | 11 | Incidental |
| CCB020293 | Cocker Spaniel | Male | Yes | 9 | Incidental, painful abdomen |
| CCB040068 | Samoyed | Male | Yes | 11 | ND |
| CCB050181 | Mixed Breed | Female | Yes | 11 | ND |
| CCB050260 | Doberman Pinsher | Female | Yes | 11 | Dyspnea |
| CCB050349 | Mixed Breed | Female | Yes | 9 | Cough |
| OSU454408 | Boston Terrier | Female | Yes | 8 | Incidental |

FIG. 8C

| Signalment and history | | | | |
|---|---|---|---|---|
| Patient ID | Breed | Sex | Neutered/ Spayed | Age at diagnosis (yr) | Clinical finding |
| OSU452418 | Mixed Breed | Male | Yes | 10 | Cough, restless, panting |
| CCB070169 | English Cocker Spaniel | Male | Yes | 8 | ND |
| CCB050362 | Mixed Breed | Male | Yes | 11 | Hemoptysis |
| CCB010196 | Labrador Retriever | Female | Yes | 8 | ND |
| CCB010139 | Labrador Retriever | Male | No | 8 | Lame |
| CCB050227 | Labrador Retriever | Female | Yes | 11 | Cough |
| CCB010358 | Greyhound | Female | Yes | 12 | Dyspnea |
| OSULSCC1 | Labrador Retriever | Female | Yes | 10 | Cough |
| CCB010120 | Labrador Retriever | Male | Yes | 9 | ND |
| CCB050353 | Bichon Frise | Female | Yes | 8 | Cough |
| OSUK9PAPADRi | Labrador Retriever | Female | Yes | 11 | Cough |

\* Only tumor data
ND = no data

FIG. 8D

Supplementary Table 2 (cont1). Extended clinical and multiplatform annotation of primary canine lung cancer cases.

| Patient ID | Histopathological diagnosis | Anthracosis | Side lung affected | Lung lobe affected | Treatment |
|---|---|---|---|---|---|
| CCB010381 | Adenocarcinoma-Tubulopapillary | Anthracosis | Left | ND | ND |
| CCB040231 | Adenocarcinoma-Papillary | No | Left | Cranial | Left craiNDl lung lobectomy |
| CCB050342 | Adenocarcinoma-Tubulopapillary | No | Right | Caudal dorsal | Right caudal lung lobectomy |
| OSU396622 | Adenocarcinoma-Papillary | No | Left | Caudal | Left caudal lung lobectomy |
| CCB010109 | Adenocarcinoma-Papillary | No | ND | ND | Removal of mass only |
| OSU361939 | Adenocarcinoma-Papillary | No | Left | Cranial | Left cranial lung lobectomy and mediastinal mass removal + 5 FU infracavity chemotherapy followed by carboplatin infusion |
| CCB030383 | Adenocarcinoma-Papillary | No | Left | Cranial | Left cranial and caudal lung lobectomies |
| CCB050097 | Adenocarcinoma-Acinar | No | Left | Caudal | Left caudal lung lobectomy |
| CCB060156 | Adenocarcinoma-Tubulopapillary | No | Left | Caudal | Left caudal lung lobectomy |
| OSU428073 | Adenocarcinoma-Papillary | No | Right | Cranial and middle | Right cranial and middle lung lobectomy + carboplatin + vinblastine |
| CCB050345 | Adenocarcinoma-Papillary | Anthracosis | Right | Caudal | Right caudal lung lobectomy |
| CCB050350 | Adenocarcinoma-Papillary | No | Right | Cranial | Right cranial lung lobectomy |
| OSU388285 | Adenocarcinoma-Papillary | No | Right | Caudal and middle | Right middle and caudal lung lobectomies |
| CCB040245 | Adenocarcinoma-Papillary | No | ND | ND | Lung lobectomy |
| CCB040385 | Adenosquamous carcinoma | No | ND | ND | ND |
| OSU424354 | Adenocarcinoma-Papillary | No | Left | Cranial | Left cranial lung lobectomy |
| CCB010387 | Adenocarcinoma-Acinar | Anthracosis | Right | Cranial | Right cranial lung lobectomy |
| OSU369339 | Adenocarcinoma-Papillary | No | Left | Caudal | Left caudal lung lobectomy |
| OSUK9PAPADO | Adenocarcinoma-Papillary | ND | Right | Cranial | Right cranial and caudal lung lobectomies |
| CCB050354 | Adenocarcinoma-Papillary | Pneumoconiosis | Right | Middle | Right middle lung lobectomy; vinorelbine: 15 mg/m^2, 14.4 mg intravenously |
| OSUK9PAPADRe | Adenocarcinoma-Mucinous papillary | ND | Right | Cranial | Right cranial lung lobectomy |
| OSU419040 | Adenocarcinoma-Papillary | No | Right | Caudal and middle | Left caudal lung lobectomy (partial debulking)+ vinblastine and carboplatin |
| CCB030381 | Adenocarcinoma-Papillary | Anthracosis | Right | Caudal | Right caudal lung lobectomy |
| CCB060143 | Adenocarcinoma-Solid | No | Right | ND | Right caudal lung lobectomy |
| CCB070294 | Adenocarcinoma-Papillary | No | Left | Caudal | Left caudal lung lobectomy +toceranib |
| CCB050356 | Adenocarcinoma | No | Left | Caudal | None |
| CLAC | Adenocarcinoma | ND | ND | ND | ND |
| OSU429271 | Adenocarcinoma | No | Left | Cranial | Left cranial lung lobectomy |
| CCB070214 | Adenocarcinoma-Acinar | No | Left | Cranial | Left cranial lung lobectomy |
| CCB070142 | Adenocarcinoma-Acinar | Anthracosis | Left | Cranial and Caudal | Left cranial and caudal lung lobectomies, gemcitabine, carboplatin |
| CCB050081 | Adenocarcinoma-Papillary | No | Left | Caudal | Right caudal lung lobectomy |
| OSU431895 | Adenocarcinoma-Tubulopapillary | No | Right | Caudal | Right caudal lung lobectomy |
| OSUK9PADSn | Adenocarcinoma-Papillary | No | Left | Cranial | Left cranial lung lobectomy |

FIG. 8E

| Patient ID | Histopathological and imaging findings ||| Lung lobe affected | Treatment |
|---|---|---|---|---|---|
| | Histopathological diagnosis | Anthracosis | Side lung affected | | |
| CCB050363 | Adenocarcinoma-Papillary | Anthracosis | Right | Caudal | Right caudal lung lobectomy |
| CCB020198 | Adenocarcinoma-Tubulopapillary | ND | Left | Caudal | Left caudal lung lobectomy |
| CCB040005 | Adenocarcinoma-Papillary | No | Left | Caudal | Left caudal lung lobectomy |
| OSUK9PADSQ | Adenosquamous carcinoma | ND | Left | Caudal | Left caudal lung lobectomy |
| CCB050243 | Adenocarcinoma-Papillary | No | Left | Caudal | Left caudal lung lobectomy |
| OSU381645 | Adenocarcinoma-Papillary | No | Left | Caudal | Left caudal lung lobectomy |
| CCB050352 | Adenocarcinoma-Papillary | Anthracosis | Right | Cranial | Right cranial lung lobectomy |
| OSU415281 | Adenocarcinoma-Papillary | No | Left | Cranial | Left cranial lung lobectomy |
| OSU422557 | Adenosquamous carcinoma | No | Right | ND | Right caudal lung lobectomy -euthansia 2 days postop |
| BACA | Adenocarcinoma | ND | ND | ND | ND |
| CCB030382 | Adenocarcinoma-Papillary | No | Right | Caudal | Right lung lobectomy - all right lung lobes |
| CCB070152 | Squamous cell carcinoma | No | Right | Caudal | Right caudal and accessory lung lobectomies |
| CCB050346 | Adenocarcinoma-Papillary | No | Left | Caudal | Left caudal lung lobectomy; carboplatin at 10mg/kg |
| CCB020070 | Adenocarcinoma-Papillary | No | Right | Caudal | Right caudal lung lobectomy |
| CCB050200 | Adenocarcinoma | No | ND | ND | ND |
| CCB020203 | Adenocarcinoma-Papillary | No | Left | Caudal | Left caudal lung lobectomy |
| CCB060040 | Adenocarcinoma-Papillary | No | ND | ND | Lung lobectomy |
| CCB060056 | Adenosquamous carcinoma | No | Left | Cranial | Left cranial lung lobectomy |
| CCB040149 | Adenocarcinoma-Mucinous papillary | Anthracosis | ND | ND | Lung lobectomy |
| CCB010227 | Adenosquamous carcinoma | No | ND | ND | Navelbine and lung lobectomy |
| CCB070114 | Adenocarcinoma-Papillary | Anthracosis | Left | Caudal | Left caudal lung lobectomy |
| CCB070295 | Adenocarcinoma-Mucinous papillary | No | Left | Caudal | Left caudal lung lobectomy |
| CCB060157 | Adenocarcinoma-Tubulopapillary | No | Right | Cranial | Right cranial lung lobectomy |
| OSUK9PAPADSh | Adenocarcinoma-Papillary | ND | Right | Caudal | Right caudal lung lobectomy |
| CCB070006 | Adenocarcinoma-Papillary | No | Right | Caudal and accessory | Right caudal and accessory lung lobectomies |
| CCB070296 | Adenosquamous carcinoma | Anthracosis | Left | Caudal | Left caudal lung lobectomy |
| OSUK9PAPADI | Adenocarcinoma-Papillary | ND | Right | Caudal | Right caudal lung lobectomy |
| OSU421496 | Adenocarcinoma-Papillary | No | Right | Caudal | Right caudal lung lobectomy + toceranib |
| OSUK9PADBa | Adenocarcinoma-Papillary | No | Left | Caudal | Left caudal lung lobectomy |
| CCB020251 | Adenocarcinoma-Papillary | No | Left | Caudal | Left caudal lung lobectomy |
| CCB040011 | Adenosquamous carcinoma | No | ND | ND | Cytotoxic chemotherapy |
| CCB010336 | Adenocarcinoma-Papillary | No | ND | ND | Vinorelbine |
| CCB050348 | Adenocarcinoma-Acinar | No | Left | Cranial | Left cranial lung lobectomy, radiation |
| CCB010105 | Adenosquamous carcinoma | No | Left | Cranial | Left lobectomy |
| OSU421496 | Squamous cell carcinoma | No | Left | ND | Lung lobectomy |
| CCB010131 | Adenocarcinoma-Papillary | No | Left | ND | Lung lobectomy |
| CCB010262 | Adenocarcinoma-Papillary | No | Right | ND | Right middle lung lobectomy, prednisone |
| CCB010379 | Adenosquamous carcinoma | No | Left | Caudal | Left caudal lung lobectomy |
| CCB020051 | Adenocarcinoma | No | Left | Caudal | Left caudal lung lobectomy |

FIG. 8F

| Patient ID | Histopathological and imaging findings | | | | Treatment |
|---|---|---|---|---|---|
| | Histopathological diagnosis | Anthracosis | Side lung affected | Lung lobe affected | |
| CCB020245 | Adenocarcinoma-Solid | No | Right | Caudal | Right caudal lung lobectomy |
| CCB020293 | Adenocarcinoma-Tubulopapillary | No | Right | Caudal | Right caudal lung lobectomy |
| CCB040068 | Adenocarcinoma-Papillary | No | Left | ND | None |
| CCB050181 | Adenocarcinoma-Solid | Anthracosis | Right | Middle | Right middle lung lobectomy |
| CCB050260 | Adenocarcinoma-Papillary | No | Right | Caudal | Right caudal lung lobectomy |
| CCB050349 | Adenosquamous carcinoma | No | Right | Caudal | Right caudal lung lobectomy |
| OSU454408 | Adenocarcinoma-Tubulopapillary | No | Right | Middle | Right middle lung lobectomy + vinorelbine 8 treatments q. 2 wks |
| OSU452418 | Adenocarcinoma-Papillary | No | Left | Caudal | Left caudal lung lobectomy |
| CCB070169 | Adenocarcinoma-Acinar | Anthracosis | Right | ND | Lung lobectomy |
| CCB050362 | Adenocarcinoma-Papillary | Anthracosis | Right | Caudal | Right caudal and accessory lung lobectomies, vinorelbine #1 15mg/m^2 = 14mg IV |
| CCB010196 | Adenosquamous carcinoma | No | Right | Caudal | Vinorelbine and Right caudal lung lobectomy |
| CCB010139 | Adenocarcinoma-Acinar | No | Right | ND | Lomustine, CCNU, iron dextron 100mg/ml, maropitant 10mg, packed red blood cells (2 units), omeprazole 20mg, famotidine 10mg/ml, amlidipine 2.5mg tabs, benazepril 20mg tabs |
| CCB050227 | Adenocarcinoma-Papillary | Anthracosis | Left | Caudal | Left caudal lung lobectomy |
| CCB010358 | Adenocarcinoma-Papillary | Anthracosis | Right | Cranial | Right cranial lung lobectomy |
| OSULSCC1 | Squamous cell carcinoma | ND | Right | Caudal | Right caudal lung lobectomy |
| CCB010120 | Adenocarcinoma-Papillary | No | Left | Caudal dorsal | Lung lobectomy |
| CCB050353 | Adenocarcinoma-Papillary | Anthracosis | Right | Cranial | Right cranial lung lobectomy |
| OSUK9PAPADRi | Adenocarcinoma-Mucinous papillary | No | Right | Cranial | Right cranial lung lobectomy |

\* Only tumor data
ND= no data

FIG. 8G

Supplementary Table 2 (cont2). Extended clinical and multiplatform annotation of primary canine lung cancer cases.

| Patient ID | Sample type | Genetic analyses | | | | | | Immunohistochemistry |
|---|---|---|---|---|---|---|---|---|
| | | Exome sequencing | Amplicon sequencing | Sanger sequencing (HER2-V659E) | Sanger sequencing (whole HER2)* | Droplet digital PCR* (HER2-V659E) | Plasma droplet digital PCR (ERBB2-V659E) | RNA Expression | HER2 |
| CCB010381 | Tumor/Normal | ND | Yes | Yes | ND | ND | ND | Yes | ND |
| CCB040231 | Tumor/Normal | ND | Yes | ND | ND | ND | ND | ND | ND |
| CCB050342 | Tumor/Normal | ND | Yes | ND | ND | ND | ND | Yes | ND |
| OSU396622 | Tumor/Normal | Yes | ND | ND | ND | Yes | ND | ND | ND |
| CCB010109 | Tumor/Normal | ND | Yes | ND | ND | ND | ND | Yes | ND |
| OSU361939 | Tumor/Normal | ND | Yes | Yes | ND | ND | Yes | Yes | ND |
| CCB030383 | Tumor/Normal | ND | Yes | ND | ND | ND | ND | ND | ND |
| CCB050097 | Tumor/Normal | ND | Yes | ND | ND | ND | ND | Yes | ND |
| CCB060156 | Tumor/Normal | ND | Yes | Yes | ND | ND | ND | ND | ND |
| OSU428073 | Tumor/Normal | ND | Yes | Yes | ND | ND | Yes | Yes | Yes |
| CCB050345 | Tumor/Normal | ND | Yes | ND | ND | ND | ND | ND | ND |
| CCB050350 | Tumor/Normal | ND | Yes | ND | ND | ND | ND | Yes | ND |
| OSU388285 | Tumor/Normal | ND | Yes | Yes | ND | ND | Yes | ND | ND |
| CCB040245 | Tumor/Normal | ND | Yes | ND | ND | ND | ND | Yes | Yes |
| CCB040385 | Tumor/Normal | ND | Yes | ND | ND | ND | ND | Yes | ND |
| OSU424354 | Tumor/Normal | Yes | Yes | Yes | ND | ND | ND | Yes | Yes |
| CCB010387 | Tumor/Normal | ND | Yes | ND | ND | ND | ND | Yes | ND |
| OSU388339 | Tumor/Normal | ND | Yes | Yes | ND | ND | Yes | ND | Yes |
| OSUK9PAPADO | Cell line | ND | Yes | ND | Yes | Yes | ND | Yes | ND |
| CCB050354 | Tumor/Normal | Yes | Yes | ND | ND | Yes | ND | ND | ND |
| OSUK9PAPADRe | Cell line | ND | Yes | ND | Yes | Yes | ND | ND | Yes |
| OSU419040 | Tumor/Normal | ND | Yes | ND | ND | ND | ND | ND | ND |
| CCB030381 | Tumor/Normal | ND | Yes | ND | ND | Yes | ND | Yes | ND |
| CCB060143 | Tumor/Normal | ND | ND | ND | ND | ND | ND | ND | ND |
| CCB070294 | Tumor/Normal | ND | Yes | ND | Yes | Yes | ND | Yes | ND |
| CCB050358 | Tumor/Normal | ND | Yes | Yes | ND | ND | ND | Yes | ND |
| CLAC | Cell line | ND | Yes | Yes | Yes | ND | ND | ND | ND |
| OSU429271 | Tumor/Normal | ND | Yes | Yes | ND | ND | Yes | Yes | ND |
| CCB070214 | Tumor/Normal | ND | Yes | ND | ND | ND | ND | Yes | ND |
| CCB070142 | Tumor/Normal | ND | Yes | ND | ND | ND | ND | Yes | ND |
| CCB050081 | Tumor/Normal | ND | Yes | ND | ND | ND | ND | Yes | ND |
| OSU431895 | Tumor/Normal | Yes | ND | ND | ND | ND | Yes | ND | ND |
| OSUK9PADSn | Cell line | ND | Yes | Yes | Yes | Yes | ND | Yes | ND |
| CCB050363 | Tumor/Normal | ND | Yes | ND | ND | ND | ND | ND | ND |
| CCB020198 | Tumor/Normal | ND | Yes | Yes | ND | Yes | Yes | Yes | ND |
| CCB040005 | Tumor/Normal | ND | Yes | Yes | ND | ND | ND | Yes | ND |
| OSUK9PADSQ | Cell line | ND | Yes | Yes | ND | ND | ND | ND | ND |
| CCB050243 | Tumor/Normal | ND | Yes | Yes | ND | Yes | ND | Yes | ND |

FIG. 8H

| | | Genetic analyses | | | | | | Immunohistochemistry | |
|---|---|---|---|---|---|---|---|---|---|
| Patient ID | Sample type | Exome sequencing | Amplicon sequencing | Sanger sequencing* (HER2-V659E) | Sanger sequencing* (whole HER2)* | Droplet digital PCR* (HER2-V659E) | Plasma droplet digital PCR (ERBB2-V659E) | RNA Expression | HER2 |
| OSU381645 | Tumor/Normal | ND | Yes | Yes | ND | ND | | Yes | Yes |
| CCB050352 | Tumor/Normal | ND | Yes | ND | ND | ND | | Yes | ND |
| OSU415281 | Tumor/Normal | ND | Yes | Yes | ND | ND | | ND | ND |
| OSU422557 | Tumor/Normal | ND | Yes | Yes | ND | ND | | Yes | ND |
| BACA | Cell line | ND | Yes | Yes | Yes | ND | | ND | ND |
| CCB030382 | Tumor/Normal | ND | Yes | ND | ND | ND | | Yes | ND |
| CCB070152 | Tumor/Normal | ND | Yes | ND | ND | ND | | ND | ND |
| CCB050346 | Tumor/Normal | ND | Yes | Yes | ND | ND | | Yes | ND |
| CCB020070 | Tumor/Normal | ND | Yes | ND | ND | ND | | Yes | ND |
| CCB050200 | Tumor/Normal | ND | Yes | ND | ND | ND | | Yes | ND |
| CCB020203 | Tumor/Normal | ND | Yes | Yes | ND | ND | Yes | ND | ND |
| CCB060040 | Tumor/Normal | ND | Yes | ND | ND | ND | ND | Yes | ND |
| CCB060056 | Tumor/Normal | ND | Yes | ND | ND | ND | ND | ND | ND |
| CCB040149 | Tumor/Normal | ND | Yes | ND | ND | ND | ND | Yes | ND |
| CCB010227 | Tumor/Normal | ND | Yes | Yes | ND | ND | ND | Yes | ND |
| CCB070114 | Tumor/Normal | ND | Yes | ND | Yes | ND | ND | ND | ND |
| CCB070295 | Tumor/Normal | ND | Yes | ND | ND | Yes | ND | Yes | ND |
| CCB060157 | Tumor/Normal | ND | Yes | ND | ND | ND | ND | ND | ND |
| OSUK9PAPADSh | Cell line | ND | Yes | Yes | Yes | Yes | ND | Yes | ND |
| CCB070006 | Tumor/Normal | ND | Yes | ND | ND | ND | ND | Yes | ND |
| CCB070296 | Tumor/Normal | ND | Yes | ND | ND | ND | ND | Yes | ND |
| OSUK9PAPADI | Cell line | ND | Yes | ND | Yes | Yes | ND | Yes | ND |
| OSU421496 | Tumor/Normal | ND | Yes | Yes | Yes | ND | ND | Yes | ND |
| OSUK9PADBa | Cell line | ND | Yes | ND | Yes | Yes | ND | Yes | ND |
| CCB020251 | Tumor/Normal | ND | Yes | ND | ND | ND | ND | Yes | ND |
| CCB040011 | Tumor/Normal | ND | Yes | ND | ND | ND | ND | Yes | ND |
| CCB010336 | Tumor/Normal | ND | Yes | ND | ND | ND | ND | Yes | ND |
| CCB050348 | Tumor/Normal | ND | Yes | ND | ND | ND | ND | Yes | ND |
| CCB010105 | Tumor/Normal | ND | Yes | ND | ND | ND | ND | Yes | ND |
| CCB010131 | Tumor/Normal | ND | Yes | ND | ND | ND | ND | ND | ND |
| CCB010262 | Tumor/Normal | ND | Yes | ND | ND | Yes | ND | Yes | ND |
| CCB010379 | Tumor/Normal | ND | Yes | ND | ND | ND | ND | Yes | ND |
| CCB020051 | Tumor/Normal | ND | Yes | Yes | ND | ND | Yes | Yes | ND |
| CCB020245 | Tumor/Normal | ND | Yes | Yes | ND | ND | Yes | Yes | ND |
| CCB020293 | Tumor/Normal | ND | Yes | ND | ND | ND | Yes | Yes | ND |
| CCB040068 | Tumor/Normal | ND | Yes | ND | ND | ND | ND | Yes | Yes |
| CCB050181 | Tumor/Normal | ND | Yes | ND | ND | ND | ND | Yes | ND |
| CCB050260 | Tumor/Normal | ND | Yes | Yes | ND | Yes | ND | Yes | ND |
| CCB050349 | Tumor/Normal | ND | Yes | ND | ND | ND | ND | Yes | ND |
| OSU454408 | Tumor/Normal | ND | Yes | Yes | ND | ND | ND | ND | Yes |
| OSU452418 | Tumor/Normal | ND | Yes | ND | ND | ND | ND | Yes | ND |
| CCB070169 | Tumor/Normal | ND | Yes | ND | ND | ND | ND | Yes | ND |

FIG. 8I

| | | Genetic analyses | | | | | | Immunohistochemistry |
|---|---|---|---|---|---|---|---|---|
| Patient ID | Sample type | Exome sequencing | Amplicon sequencing | Sanger sequencing* (HER2-V659E) | Sanger sequencing (whole HER2)* | Droplet digital PCR* (HER2-V659E) | Plasma droplet digital PCR (ERBB2-V659E) | RNA Expression | HER2 |
| CCB050362 | Tumor/Normal | ND | Yes | Yes | ND | ND | ND | Yes | ND |
| CCB010196 | Tumor/Normal | ND | Yes | ND | ND | ND | ND | ND | ND |
| CCB010139 | Tumor/Normal | ND | Yes | ND | ND | ND | ND | Yes | ND |
| CCB050227 | Tumor/Normal | Yes | ND | ND | ND | Yes | ND | ND | ND |
| CCB010358 | Tumor/Normal | ND | Yes | ND | ND | ND | ND | Yes | ND |
| OSULSCC1 | Cell line | ND | Yes | Yes | Yes | ND | ND | ND | ND |
| CCB010120 | Tumor/Normal | ND | Yes | Yes | ND | ND | ND | Yes | ND |
| CCB050353 | Tumor/Normal | ND | ND | ND | ND | ND | ND | ND | ND |
| OSUK9PAPADRi | Cell line | | | Yes | Riley | | | | ND |

* Only tumor data
ND= no data

FIG. 8J

Supplementary Table 4. Somatic coding SNVs identified by exome sequencing of primary canine lung cancers.

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| CCB010387 | ENSCAFG00000024198 | ENSCAFT00000048483.2 | chr1:103124016A>G | | c.547A>G | p.Asn183Asp | Missense variant | 13% |
| CCB010387 | ENSCAFG00000031824 | ENSCAFT00000044443.1 | chr1:110344193G>A | | c.746G>A | p.Arg249His | Missense variant | 58% |
| CCB010387 | ENSCAFG00000001785 | ENSCAFT00000002602.3 | chr10:31022318G>A | | c.529G>A | p.Asp177Asn | Missense variant | 21% |
| CCB010387 | KCNK12 | ENSCAFT00000046978.1 | chr10:49671039G>T | | c.349C>A | p.Pro117Thr | Missense variant | 17% |
| CCB010387 | KDR | ENSCAFT00000003300.3 | chr13:47443084C>T | | c.3848-1G>A | | Splice acceptor variant | 41% |
| CCB010387 | TMPRSS11F | ENSCAFT00000044486.3 | chr13:58569540G>T | | c.128C>A | p.Thr43Asn | Missense variant | 15% |
| CCB010387 | HGF | ENSCAFT00000010288.3 | chr18:21342802AC>A | | c.1618+1delG | | Splice donor variant | 34% |
| CCB010387 | ENSCAFG00000024737 | ENSCAFT00000023283.3 | chr19:51478247A>C | | c.1055T>G | p.Leu352Arg | Missense variant | 23% |
| CCB010387 | ENSCAFG00000030414 | ENSCAFT00000046090.1 | chr22:59203429G>A | | c.728C>T | p.Thr243Ile | Missense variant | 11% |
| CCB010387 | ARPP21 | ENSCAFT00000007650.4 | chr23:5811527C>A | | c.1354+8C>A | | Splice region variant | 25% |
| CCB010387 | PRKG1 | ENSCAFT00000044295.2 | chr26:35767282C>T | | c.812G>A | p.Arg271Gln | Missense variant | 15% |
| CCB010387 | ACTA2 | ENSCAFT00000024861.3 | chr26:38707206G>A | | c.289C>T | p.Arg97Cys | Missense variant | 38% |
| CCB010387 | UNC13C | ENSCAFT00000025186.3 | chr30:19556056A>T | | c.607A>T | p.Met203Leu | Missense variant | 37% |
| CCB010387 | ISLR | ENSCAFT00000028352.3 | chr30:37326596G>A | | c.1447G>A | p.Val483Ile | Missense variant | 30% |
| CCB010387 | HLCS | ENSCAFT00000015393.3 | chr31:31943202C>T | | c.1682G>A | p.Ser561Asn | Missense variant | 34% |
| CCB010387 | ENSCAFG00000032143 | ENSCAFT00000046842.1 | chr33:5301141T>A | | c.794T>A | p.Val265Asp | Missense variant | 40% |
| CCB010387 | PHLDB1 | ENSCAFT00000019942.4 | chr5:15101566G>A | | c.3517C>T | p.Arg1173Trp | Missense variant | 50% |
| CCB010387 | IQCE | ENSCAFT00000036666.3 | chr6:14540101C>T | | c.217-3C>T | | Splice region variant | 6% |
| CCB010387 | ENSCAFG00000016834 | ENSCAFT00000026354.3 | chr6:17505745C>G | | c.583G>C | p.Asp195His | Missense variant | 8% |
| CCB010387 | USP33 | ENSCAFT00000032445.3 | chr6:69155680G>T | | c.1509G>T | p.Glu503Asp | Missense variant | 54% |
| CCB010387 | MIS18BP1 | ENSCAFT00000022361.4 | chr8:22647430A>C | | c.2037T>G | p.Cys679Trp | Missense variant | 13% |
| CCB010387 | ERBB2 | ENSCAFT00000025936.3 | chr9:22785127A>T | | c.1976T>A | p.Val659Glu | Missense variant | 44% |
| CCB010387 | SLC43A2 | ENSCAFT00000030472.2 | chr9:45767181C>A | | c.202G>T | p.Glu68* | Stop-gained variant | 8% |
| CCB010387 | ENSCAFG00000019755 | ENSCAFT00000031414.3 | chr9:49689729T>G | | c.374A>C | p.Tyr125Ser | Missense variant | 27% |
| CCB010387 | ACE2 | ENSCAFT00000019262.3 | chrX:11818516G>T | | c.1034C>A | p.Pro345His | Missense variant | 29% |
| CCB010387 | TNMD | ENSCAFT00000027750.3 | chrX:74474211T>C | | c.622T>C | p.Phe208Leu | Missense variant | 28% |
| CCB050227 | SYNE1 | ENSCAFT00000000760.4 | chr1:42441824C>G | | c.23289G>C | p.Leu7763Phe | Missense variant | 10% |
| CCB050227 | FREM1 | ENSCAFT00000002397.3 | chr11:35220245G>C | | c.4600C>G | p.Leu1534Val | Missense variant | 70% |
| CCB050227 | COL14A1 | ENSCAFT00000001452.3 | chr13:19125873G>A | | c.2302G>A | p.Val768Met | Missense variant | 37% |
| CCB050227 | MPP6 | ENSCAFT00000004508.3 | chr14:38182881A>C | | c.1042A>C | p.Lys348Gln | Missense variant | 46% |
| CCB050227 | ZNF800 | ENSCAFT00000002714.3 | chr14:88807810C>A | | c.158-7C>A | | Splice region variant | 23% |
| CCB050227 | PABPC4 | ENSCAFT00000004949.4 | chr15:32992275C>A | | c.407C>A | p.Ser136Tyr | Missense variant | 39% |
| CCB050227 | GIMAP8 | ENSCAFT00000007370.2 | chr16:14757724G>C | | c.638G>C | p.Ser213Thr | Missense variant | 5% |
| CCB050227 | CSMD1 | ENSCAFT00000013869.4 | chr16:55503451C>A | | c.1307G>T | p.Arg436Ile | Missense variant | 42% |
| CCB050227 | MFSD2B | ENSCAFT00000006341.3 | chr17:18504848G>A | | c.1249G>A | p.Ala417Thr | Missense variant | 35% |
| CCB050227 | PCLO | ENSCAFT00000010157.3 | chr18:22512128C>T | | c.9742G>A | p.Ala3248Thr | Missense variant | 38% |
| CCB050227 | OR4P4 | ENSCAFT00000012973.3 | chr18:40239473C>A | | c.802G>T | p.Val268Leu | Missense variant | 39% |
| CCB050227 | SART1 | ENSCAFT00000020606.3 | chr18:51299864G>A | | c.1741C>T | p.Arg581Trp | Missense variant | 51% |
| CCB050227 | CAPN1 | ENSCAFT00000021965.3 | chr18:52006009T>TA | | c.942_943insT | p.Asn315fs | Frameshift variant | 30% |
| CCB050227 | MBD5 | ENSCAFT00000008917.3 | chr19:50235818G>A | | c.4331G>A | p.Ser1444Asn | Missense variant | 39% |
| CCB050227 | PTAFR | ENSCAFT00000018694.3 | chr2:72255041G>A | | c.673G>A | p.Ala225Thr | Missense variant | 20% |

FIG. 10A

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| CCB050227 | EEFSEC | ENSCAFT00000006626.3 | chr20:2273716C>T | | c.1073C>T | p.Ser358Phe | Missense variant | 66% |
| CCB050227 | FANCD2 | ENSCAFT00000008366.3 | chr20:8253085C>T | | c.3274C>A | p.Glu1092Lys | Missense variant | 76% |
| CCB050227 | ENSCAFG00000005230 | ENSCAFT00000008452.3 | chr21:22004023G>A | | c.1532G>A | p.Arg511Gln | Missense variant | 45% |
| CCB050227 | OR51G2 | ENSCAFT00000019954.3 | chr21:27380444C>T | | c.883G>A | p.Val295Ile | Missense variant | 33% |
| CCB050227 | ENSCAFG00000006321 | ENSCAFT00000010223.3 | chr21:29981291G>T | | c.852G>T | p.Leu284Phe | Missense variant | 8% |
| CCB050227 | MBNL2 | ENSCAFT00000008902.3 | chr22:47695351C>A | | c.844C>A | p.Gln282Lys | Missense variant | 43% |
| CCB050227 | FBXO25 | ENSCAFT00000016193.2 | chr25:37451577C>T | | c.235C>T | p.Gln79* | Stop-gained variant | 69% |
| CCB050227 | ADAMTSL3 | ENSCAFT00000021096.3 | chr3:55577631G>A | | c.1849G>A | p.Glu617Lys | Missense variant | 33% |
| CCB050227 | IRX4 | ENSCAFT00000016578.3 | chr34:10928900G>C | | c.685G>C | p.Glu229Gln | Missense variant | 44% |
| CCB050227 | CNTN2 | ENSCAFT00000037921.2 | chr38:15854820G>A | | c.1081G>A | p.Glu361Lys | Missense variant | 41% |
| CCB050227 | NIPBL | ENSCAFT00000044310.2 | chr4:71598459T>C | | c.6682A>G | p.Ile2228Val | Missense variant | 48% |
| CCB050227 | DNAH2 | ENSCAFT00000026606.3 | chr5:32634372C>A | | c.2918C>A | p.Ser973Tyr | Missense variant | 66% |
| CCB050227 | MYH13 | ENSCAFT00000027662.3 | chr5:34638774G>A | | c.2891C>T | p.Thr964Met | Missense variant | 13% |
| CCB050227 | ZSWIM7 | ENSCAFT00000028717.3 | chr5:39668255G>C | | c.48G>C | p.Glu16Asp | Missense variant | 74% |
| CCB050227 | ENSCAFG00000014044 | ENSCAFT00000022201.3 | chr6:58112223G>C | | c.7728C>G | p.Ser2576Arg | Missense variant | 6% |
| CCB050227 | MYBPH | ENSCAFT00000016341.3 | chr7:41692G>A | | c.1003G>A | p.Gly335Arg | Missense variant | 24% |
| CCB050227 | NLRP3 | ENSCAFT00000017002.3 | chr8:2592283G>T | | c.1687G>T | p.Glu563* | Stop-gained variant | 30% |
| CCB050227 | ERBB2 | ENSCAFT00000025936.3 | chr9:22765127A>T | | c.1976T>A | p.Val659Glu | Missense variant | 54% |
| CCB050227 | CACNA1G | ENSCAFT00000027129.5 | chr9:26518243G>A | | c.3288G>A | p.Ala1090Thr | Missense variant | 7% |
| CCB050227 | ENTPD2 | ENSCAFT00000031028.1 | chr9:48590996G>A | | c.133G>A | p.Asp45Asn | Missense variant | 26% |
| CCB050227 | SLITRK2 | ENSCAFT00000030252.3 | chrX:114531830T>C | | c.761T>C | p.Val254Ala | Missense variant | 38% |
| CCB050227 | CITED1 | ENSCAFT00000027168.3 | chrX:56327283G>T | | c.565C>A | p.Leu189Met | Missense variant | 43% |
| CCB050227 | DIAPH2 | ENSCAFT00000035855.2 | chrX:71042970A>C | | c.3308A>C | p.Lys1103Thr | Missense variant | 8% |
| CCB050354 | ENSCAFG00000026536 | ENSCAFT00000001265.3 | chr1:54190681C>T | | c.539G>A | p.Arg180His | Missense variant | 22% |
| CCB050354 | ENSCAFG00000001339 | ENSCAFT00000022078.3 | chr1:73521101C>A | | c.66+4C>A | | Splice region variant | 18% |
| CCB050354 | MICALL1 | ENSCAFT00000022244.4 | chr10:26728936C>A | | c.926+1G>T | | Splice donor variant | 49% |
| CCB050354 | ENSCAFG00000005307 | ENSCAFT00000029311.3 | chr10:38390829C>A | | c.263C>A | p.Ala88Asp | Missense variant | 12% |
| CCB050354 | ENSCAFG00000001853 | ENSCAFT00000029214.1 | chr12:11905302C>A | | c.1825C>A | p.Pro609Thr | Missense variant | 17% |
| CCB050354 | CSMD3 | ENSCAFT00000012238.4 | chr13:124530336C>A | | c.9200G>T | p.Arg3067Ile | Missense variant | 40% |
| CCB050354 | WDR35 | ENSCAFT00000006134.4 | chr17:15030766C>A | | c.255G>T | p.Lys85Asn | Missense variant | 14% |
| CCB050354 | APOB | ENSCAFT00000006286.2 | chr17:15888008G>A | | c.4987C>T | p.Arg1663Cys | Missense variant | 38% |
| CCB050354 | MAML3 | ENSCAFT00000015950.3 | chr19:28912187T>G | | c.108T>G | p.Phe36Leu | Missense variant | 19% |
| CCB050354 | ATP9A | ENSCAFT00000018585.3 | chr24:37804580A>G | | c.2732T>C | p.Leu911Pro | Missense variant | 20% |
| CCB050354 | SLC6B1 | ENSCAFT00000046446.2 | chr26:10679000C>G | | c.568G>C | p.Ala190Pro | Missense variant | 18% |
| CCB050354 | LCOR | ENSCAFT00000048723.1 | chr28:10333164A>G | | c.1801A>G | p.Thr601Ala | Missense variant | 22% |
| CCB050354 | PGLK | ENSCAFT00000014935.3 | chr3:30811008C>A | | c.1083+1G>T | | Splice donor variant | 24% |
| CCB050354 | PDE6B | ENSCAFT00000026577.3 | chr3:91751745A>C | | c.1786T>G | p.Cys596Gly | Missense variant | 11% |
| CCB050354 | ENSCAFG00000024680 | ENSCAFT00000038074.3 | chr3:91947438C>G | | c.911C>G | p.Ser304Cys | Missense variant | 19% |
| CCB050354 | ZSCAN12 | ENSCAFT00000018931.3 | chr35:25536627C>A | | c.421C>T | p.Val141Phe | Missense variant | 17% |
| CCB050354 | ERBB4 | ENSCAFT00000022535.3 | chr37:19041081C>T | | c.3007-8G>A | | Splice region variant | 13% |
| CCB050354 | ENSCAFG00000016100 | ENSCAFT00000048260.1 | chr4:34757216C>T | | c.1082G>A | p.Gly361Asp | Missense variant | 14% |
| CCB050354 | CALB2 | ENSCAFT00000037364.2 | chr5:77189552C>A | | c.56C>A | p.Ala19Asp | Missense variant | 21% |
| CCB050354 | RNPEP | ENSCAFT00000016772.3 | chr7:970490A>AG | | c.1239dupC | p.Tyr414fs | Frameshift variant | 21% |

FIG. 10B

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| CCB050354 | ERBB2 | ENSCAFT00000025936.3 | chr9:22765077T>C | | c.2026A>G | p.Lys676Glu | Missense variant | 35% |
| CCB050354 | CALCOCO2 | ENSCAFT00000026722.3 | chr9:25058008C>T | | c.154C>T | p.Arg52* | Stop-gained variant | 23% |
| CCB050354 | UNC45B | ENSCAFT00000029046.3 | chr9:38190461C>G | | c.2653G>C | p.Val885Leu | Missense variant | 17% |
| CCB050354 | COL5A1 | ENSCAFT00000031582.4 | chr9:50832901G>C | | c.4007G>C | p.Gly1336Ala | Missense variant | 32% |
| CCB050354 | CERCAM | ENSCAFT00000031918.3 | chr9:55110594G>A | | c.1717C>T | p.Arg573Cys | Missense variant | 19% |
| CCB050354 | AFF2 | ENSCAFT00000030321.3 | chrX:117131825C>T | | c.2065C>T | p.Pro689Ser | Missense variant | 23% |
| CCB050354 | ARSH | ENSCAFT00000017754.3 | chrX:1579713A>G | | c.961A>G | p.Thr321Ala | Missense variant | 23% |
| OSU396622 | GLIPR1L2 | ENSCAFT00000048594.1 | chr10:15924621G>T | | c.109G>T | p.Gly37Trp | Missense variant | 26% |
| OSU396622 | PNPLA1 | ENSCAFT00000002155.3 | chr12:54173910C>T | | c.1448C>T | p.Pro483Leu | Missense variant | 17% |
| OSU396622 | POU3F2 | ENSCAFT00000043152.1 | chr12:57104161A>C | | c.77A>C | p.Gln26Pro | Missense variant | 8% |
| OSU396622 | MDR1 | ENSCAFT00000002896.3 | chr14:13717741G>T | | c.422C>A | p.Ala141Glu | Missense variant | 22% |
| OSU396622 | TLL1 | ENSCAFT00000014157.3 | chr15:61687957G>T | | c.1337G>T | p.Trp446Leu | Missense variant | 7% |
| OSU396622 | CSMD2 | ENSCAFT00000005832.4 | chr15:80061380C>T | | c.1756+8C>T | | Splice region variant | 14% |
| OSU396622 | SGCZ | ENSCAFT00000010944.3 | chr18:37844479A>G | | c.277T>C | p.Tyr93His | Missense variant | 6% |
| OSU396622 | SLC7A2 | ENSCAFT00000011153.3 | chr16:40855325C>T | | c.20C>T | p.Ala7Val | Missense variant | 24% |
| OSU396622 | AIM1L | ENSCAFT00000019665.4 | chr2:736870646G>A | | c.3371G>A | p.Gly1124Glu | Missense variant | 19% |
| OSU396622 | ENSCAFG00000005282 | ENSCAFT00000008518.3 | chr2:360707777G>A | | c.1185G>A | p.Ser395Ser | Splice region variant | 21% |
| OSU396622 | MYO16 | ENSCAFT00000009790.3 | chr22:576554546G>T | | c.3277G>T | p.Val1093Leu | Missense variant | 23% |
| OSU396622 | ENSCAFG00000018047 | ENSCAFT00000028683.4 | chr30:38467600C>T | | c.2318C>T | p.Thr773Met | Missense variant | 27% |
| OSU396622 | NRSN1 | ENSCAFT00000048012.1 | chr35:222359466G>A | | c.298G>A | p.Asp100Asn | Missense variant | 27% |
| OSU396622 | CFLAR | ENSCAFT00000019278.2 | chr37:103048078TG>T | | c.1021delG | p.Asp341fs | Frameshift variant | 28% |
| OSU396622 | CFLAR | ENSCAFT00000019278.2 | chr37:103044880G>T | | c.1021G>T | p.Asp341Tyr | Missense variant | 26% |
| OSU396622 | NBEAL1 | ENSCAFT00000020215.4 | chr37:119896390C>A | | c.4376C>A | p.Ser1459Tyr | Missense variant | 30% |
| OSU396622 | SUSD4 | ENSCAFT00000018068.3 | chr38:23671827G>A | | c.218G>A | p.Arg73His | Missense variant | 20% |
| OSU396622 | PER1 | ENSCAFT00000026908.4 | chr5:32962533C>T | | c.2082G>A | p.Glu688Lys | Missense variant | 24% |
| OSU396622 | FBXL18 | ENSCAFT00000025425.3 | chr6:124487190G>A | | c.1096G>A | p.Glu366Lys | Missense variant | 20% |
| OSU396622 | CACNA1E | ENSCAFT00000020724.5 | chr7:15200535C>T | | c.3218C>T | p.Thr1073Met | Missense variant | 20% |
| OSU396622 | KIF21B | ENSCAFT00000017574.3 | chr7:22060620G>T | | c.1467-4G>T | | Splice region variant | 20% |
| OSU396622 | MBD1 | ENSCAFT00000030047.3 | chr7:78605634G>C | | c.1684G>C | p.Val562Leu | Missense variant | 16% |
| OSU396622 | KCNK10 | ENSCAFT00000043710.2 | chr8:594879700C>T | | c.940G>A | p.Val314Ile | Missense variant | 21% |
| OSU396622 | KIF26A | ENSCAFT00000029108.4 | chr8:71824126G>A | | c.4085G>A | p.Arg1362Gln | Missense variant | 27% |
| OSU396622 | ERBB2 | ENSCAFT00000025936.3 | chr9:22785127A>T | | c.1976T>A | p.Val659Glu | Missense variant | 20% |
| OSU431895 | TSEN34 | ENSCAFT00000004233.3 | chr1:103021904C>A | | c.864G>T | p.Lys288Asn | Missense variant | 34% |
| OSU431895 | ENSCAFG00000002834 | ENSCAFT00000004536.3 | chr1:105568333G>A | | c.473G>A | p.Arg158His | Missense variant | 37% |
| OSU431895 | PPM1N | ENSCAFT00000071128.3 | chr1:110068586G>C | | c.1140-6C>G | | Splice region variant | 30% |
| OSU431895 | CLPTM1 | ENSCAFT00000074230.3 | chr1:110493865AG>A | | c.73-6delC | | Splice region variant | 14% |
| OSU431895 | CCDC97 | ENSCAFT00000008063.4 | chr1:112653365G>T | | c.712C>A | p.Gln238Lys | Missense variant | 27% |
| OSU431895 | PAK4 | ENSCAFT00000099039.4 | chr1:114014367G>A | | c.860C>T | p.Pro287Leu | Missense variant | 36% |
| OSU431895 | ZFP62 | ENSCAFT00000045420.1 | chr1:116038973A>T | | c.332T>A | p.Leu111* | Stop-gained variant | 29% |
| OSU431895 | URI1 | ENSCAFT00000012164.4 | chr1:121611868G>C | | c.28C>G | p.Leu10Val | Missense variant | 27% |
| OSU431895 | BCLAF1 | ENSCAFT00000000383.4 | chr1:28873811T>G | | c.38C>G | p.Ser13* | Stop-gained variant | 5% |
| OSU431895 | SERAC1 | ENSCAFT00000000999.3 | chr1:47609753C>A | | c.1117G>T | p.Glu373* | Stop-gained variant | 23% |
| OSU431895 | LAMA2 | ENSCAFT00000001697.4 | chr1:67645594G>T | | c.141G>T | p.Arg47Ser | Missense variant | 10% |

FIG. 10C

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| OSU431895 | CD274 | ENSCAFT00000003346.3 | chr1:93590856G>C | | c.314G>C | p.Arg105Thr | Missense variant | 24% |
| OSU431895 | ERMP1 | ENSCAFT00000003361.3 | chr1:93880291C>T | | c.628G>A | p.Asp210Asn | Missense variant | 30% |
| OSU431895 | PTPRB | ENSCAFT00000000719.4 | chr10:12302391G>A | | c.4715-7C>T | | Splice region variant | 21% |
| OSU431895 | ZFC3H1 | ENSCAFT00000000728.4 | chr10:13201668C>G | | c.1061G>C | p.Arg354Thr | Missense variant | 23% |
| OSU431895 | TBC1D15 | ENSCAFT00000000735.3 | chr10:13382797C>G | | c.206C>G | p.Ser69Cys | Missense variant | 24% |
| OSU431895 | TTLL12 | ENSCAFT00000001412.3 | chr10:22383057G>C | | c.1699G>C | p.Asp567His | Missense variant | 21% |
| OSU431895 | CHADL | ENSCAFT00000001705.3 | chr10:23998212C>A | | c.2195C>A | p.Ser732Tyr | Missense variant | 27% |
| OSU431895 | SEPT10 | ENSCAFT00000047214.1 | chr10:34297349C>T | | c.991C>T | p.Gln331* | Stop-gained variant | 23% |
| OSU431895 | SLC16A7 | ENSCAFT00000004487.3 | chr10:34911550>C | | c.678G>C | p.Lys226Asn | Missense variant | 22% |
| OSU431895 | EPCAM | ENSCAFT00000004180.3 | chr10:49493762C>G | | c.731C>G | p.Pro244Arg | Missense variant | 21% |
| OSU431895 | FOXN2 | ENSCAFT00000046196.1 | chr10:50260429C>G | | c.476C>G | p.Ser159Cys | Missense variant | 13% |
| OSU431895 | SPTBN1 | ENSCAFT00000004367.4 | chr10:55558060C>T | | c.6301C>T | p.Pro2101Ser | Missense variant | 21% |
| OSU431895 | TEX43 | ENSCAFT00000000911.2 | chr11:15908369G>C | | c.300G>C | p.Leu100Phe | Missense variant | 27% |
| OSU431895 | SPAG8 | ENSCAFT00000044181.2 | chr1:24230730C>T | | c.691G>A | p.Glu231Lys | Missense variant | 26% |
| OSU431895 | DDX39B | ENSCAFT00000035511.2 | chr12:1042882G>A | | c.113C>T | p.Ser38Phe | Missense variant | 23% |
| OSU431895 | TAP1 | ENSCAFT00000001306.3 | chr12:2431980C>A | | c.89G>T | p.Arg30Met | Missense variant | 28% |
| OSU431895 | TAP1 | ENSCAFT00000001306.3 | chr12:2431981T>A | | c.88A>T | p.Arg30Trp | Missense variant | 30% |
| OSU431895 | COL19A1 | ENSCAFT00000004046.4 | chr12:32509880G>C | | c.915G>C | p.Gln305His | Missense variant | 23% |
| OSU431895 | NRM | ENSCAFT00000000694.5 | chr12:482875C>A | | c.2296G>T | p.Asp766Tyr | Missense variant | 13% |
| OSU431895 | NRM | ENSCAFT00000000694.5 | chr12:482885G>C | | c.2286C>G | p.Asp762Glu | Missense variant | 10% |
| OSU431895 | MDN1 | ENSCAFT00000043198.2 | chr12:48983311A>G | | c.1892T>C | p.Val631Ala | Missense variant | 31% |
| OSU431895 | SLC45A4 | ENSCAFT00000019161.3 | chr15:35744576G>A | | c.61C>T | p.Gln21* | Stop-gained variant | 19% |
| OSU431895 | CPSF1 | ENSCAFT00000002514.3 | chr13:37818701C>T | | c.3484G>A | p.Asp1162Asn | Missense variant | 20% |
| OSU431895 | KIT | ENSCAFT00000049830.2 | chr13:47179167G>C | | c.1929G>C | p.Leu643Phe | Missense variant | 15% |
| OSU431895 | ZFPM2 | ENSCAFT00000001049.4 | chr13:64357637T>A | | c.181T>A | p.Cys61Ser | Missense variant | 18% |
| OSU431895 | FAM126A | ENSCAFT00000004353.3 | chr14:36657833C>T | | c.160G>A | p.Glu54Lys | Missense variant | 24% |
| OSU431895 | GPNMB | ENSCAFT00000004389.2 | chr14:36933861G>A | | c.682G>A | p.Val228Met | Missense variant | 18% |
| OSU431895 | ENSCAFG00000002897 | ENSCAFT00000046832.3 | chr14:39514372G>C | | c.187+5G>C | | Splice region variant | 16% |
| OSU431895 | ANLN | ENSCAFT00000005209.3 | chr14:47818863G>T | | c.790G>T | p.Asp264Tyr | Missense variant | 24% |
| OSU431895 | ENSCAFG00000023485 | ENSCAFT00000036128.2 | chr14:58969628G>C | | c.518G>C | p.Arg173Thr | Missense variant | 24% |
| OSU431895 | CPA1 | ENSCAFT00000023133 | chr14:65654780>C | | c.815C>G | p.Ser272* | Stop-gained variant | 7% |
| OSU431895 | ENSCAFG00000028806 | ENSCAFT00000046383.1 | chr15:14094033G>A | | c.662C>T | p.Ser221Phe | Missense variant | 7% |
| OSU431895 | PPIE | ENSCAFT00000046078.1 | chr15:31895583C>G | | c.174+5G>C | | Splice region variant | 18% |
| OSU431895 | MMAA | ENSCAFT00000012297.2 | chr15:44232274G>A | | c.229G>A | p.Glu77Lys | Missense variant | 17% |
| OSU431895 | AGBL3 | ENSCAFT00000005114.3 | chr15:130618550>G | | c.1122G>C | p.Met374Ile | Missense variant | 26% |
| OSU431895 | ENSCAFG00000003149 | ENSCAFT00000005066.3 | chr16:13821050C>T | | c.845C>T | p.Ser282Phe | Missense variant | 20% |
| OSU431895 | KRBA1 | ENSCAFT00000045150.2 | chr16:14495233G>C | | c.121G>C | p.Glu41Gln | Missense variant | 23% |
| OSU431895 | WDR60 | ENSCAFT00000008456.3 | chr16:20823434G>C | | c.826G>C | p.Glu276Gln | Missense variant | 20% |
| OSU431895 | ENSCAFG00000028458 | ENSCAFT00000042754.1 | chr16:37346060>A | | c.602G>A | p.Gly201Glu | Missense variant | 9% |
| OSU431895 | LONRF1 | ENSCAFT00000047804.1 | chr16:36244321C>G | | c.859G>C | p.Asp287His | Missense variant | 19% |
| OSU431895 | ENSCAFG00000006873 | ENSCAFT00000011052.3 | chr16:40524050G>C | | c.333G>C | p.Leu111Phe | Missense variant | 20% |
| OSU431895 | ENSCAFG00000008367 | ENSCAFT00000013291.3 | chr16:51552737G>T | | c.1400G>T | p.Arg467Leu | Missense variant | 22% |
| OSU431895 | APOB | ENSCAFT00000096266.2 | chr17:15886395C>G | | c.6600C>G | p.Ile2200Met | Missense variant | 28% |

FIG. 10D

| Patent ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| OSU431895 | TSSC1 | ENSCAFT00000005219.3 | chr17:1870470C>T | | c.990-1G>A | | Splice acceptor variant | 20% |
| OSU431895 | DPYSL5 | ENSCAFT00000007378.3 | chr17:20895379C>A | | c.246C>A | p.Phe82Leu | Missense variant | 26% |
| OSU431895 | PLB1 | ENSCAFT00000008431.3 | chr17:22547880G>A | | c.3822G>A | p.Gln1274Gln | Splice region variant | 24% |
| OSU431895 | C2orf71 | ENSCAFT00000036452.3 | chr17:22907687C>G | | c.2851G>C | p.Asp951His | Missense variant | 19% |
| OSU431895 | CEBPZ | ENSCAFT00000009851.3 | chr17:29570374C>T | | c.2515G>A | p.Glu839Lys | Missense variant | 23% |
| OSU431895 | NOTCH2 | ENSCAFT00000016889.3 | chr17:56870205C>T | | c.5137G>A | p.Glu1713Lys | Missense variant | 26% |
| OSU431895 | TXNIP | ENSCAFT00000018124.3 | chr17:58777650G>C | | c.811C>G | p.Arg271Gly | Missense variant | 29% |
| OSU431895 | ZNF687 | ENSCAFT00000020030.3 | chr17:60356209G>C | | c.2200G>C | p.Glu734Gln | Missense variant | 21% |
| OSU431895 | DTX4 | ENSCAFT00000012238.3 | chr18:37526136G>A | | c.739C>T | p.Arg247Trp | Missense variant | 32% |
| OSU431895 | ENSCAFG00000025503 | ENSCAFT00000039659.2 | chr18:38128118G>A | | c.787G>A | p.Val263Ile | Missense variant | 31% |
| OSU431895 | ENSCAFG00000031163 | ENSCAFT00000047375.1 | chr18:39799057C>T | | c.361G>A | p.Asp121Asn | Missense variant | 24% |
| OSU431895 | TRPM5 | ENSCAFT00000016218.3 | chr18:46485577C>A | | c.1806G>T | p.Arg602Ser | Missense variant | 32% |
| OSU431895 | ENSCAFG00000032485 | ENSCAFT00000046317.1 | chr18:51424509C>T | | c.614C>T | p.Ser205Leu | Missense variant | 15% |
| OSU431895 | AHNAK | ENSCAFT00000048755.1 | chr18:54101249G>T | | c.2726G>T | p.Gly909Val | Missense variant | 23% |
| OSU431895 | GLI3 | ENSCAFT00000049220.2 | chr18:80546666C>G | | c.1758C>G | p.Phe586Leu | Missense variant | 26% |
| OSU431895 | KIFC3 | ENSCAFT00000035418.2 | chr2:58730920C>T | | c.2314C>T | p.Arg772Cys | Missense variant | 23% |
| OSU431895 | ABCC12 | ENSCAFT00000016220.4 | chr2:66965092G>A | | c.3800G>A | p.Arg1287His | Missense variant | 24% |
| OSU431895 | DNAJC8 | ENSCAFT00000018890.4 | chr2:72193839T>C | rs851990132 | c.2T>C | p.Met1? | Start-lost variant | 6% |
| OSU431895 | EXTL1 | ENSCAFT00000020161.3 | chr2:73934086C>A | | c.1516-1G>T | | Splice acceptor variant | 21% |
| OSU431895 | PGD | ENSCAFT00000026597.3 | chr2:85397951C>G | | c.780G>C | p.Gln260His | Missense variant | 6% |
| OSU431895 | ARHGAP21 | ENSCAFT00000044523.2 | chr2:2864689G>C | | c.3373G>C | p.Asp1125His | Missense variant | 7% |
| OSU431895 | FOXP1 | ENSCAFT00000010478.5 | chr20:21009967G>T | | c.1834G>T | p.Glu612* | Stop-gained variant | 22% |
| OSU431895 | FAM3D | ENSCAFT00000043106.2 | chr20:32037061G>C | | c.417G>C | p.Glu139Asp | Missense variant | 30% |
| OSU431895 | HDAC11 | ENSCAFT00000007075.3 | chr20:38128496>A | | c.481G>A | p.Glu161Lys | Missense variant | 31% |
| OSU431895 | PODNL1 | ENSCAFT00000026169.4 | chr20:48545684C>T | | c.498-3C>T | | Splice region variant | 33% |
| OSU431895 | ZSWIM4 | ENSCAFT00000026294.4 | chr20:48633250G>A | | c.1492C>T | p.Arg498Trp | Missense variant | 28% |
| OSU431895 | PLXND1 | ENSCAFT00000017454.4 | chr20:55873276G>A | | c.2626G>A | p.Asp876Asn | Missense variant | 28% |
| OSU431895 | ENSCAFG00000023709 | ENSCAFT00000036630.3 | chr20:57338199G>C | | c.1740C>G | p.Phe580Leu | Missense variant | 4% |
| OSU431895 | INPPL1 | ENSCAFT00000009283.3 | chr21:25903221C>A | | c.2901G>T | p.Leu967Phe | Missense variant | 32% |
| OSU431895 | TRIM34 | ENSCAFT00000010112.4 | chr21:28642194G>C | | c.1476G>C | p.Glu492Asp | Missense variant | 28% |
| OSU431895 | ENSCAFG00000029611 | ENSCAFT00000010146.2 | chr21:28714549A>C | | c.883A>C | p.Thr295Pro | Missense variant | 25% |
| OSU431895 | WEE1 | ENSCAFT00000011883.4 | chr21:32843558C>T | | c.239C>T | p.Pro80Leu | Missense variant | 33% |
| OSU431895 | DNAJC13 | ENSCAFT00000010177.3 | chr23:29437198C>A | | c.1350-7C>A | | Splice region variant | 21% |
| OSU431895 | C20orf194 | ENSCAFT00000010311.3 | chr24:179581910>C | | c.706C>G | p.Asp81His | Missense variant | 22% |
| OSU431895 | CTSA | ENSCAFT00000015596.4 | hr24:33188262T>TAAGGC, +2_1311+3insA/ | | | | Splice region variant | 16% |
| OSU431895 | NEFM | ENSCAFT00000014336.4 | chr25:32494886C>G | | c.1712G>C | p.Gly571Ala | Missense variant | 42% |
| OSU431895 | CCDC60 | ENSCAFT00000015857.3 | chr26:155946320G>A | | c.959G>A | p.Gly320Glu | Missense variant | 40% |
| OSU431895 | CMKLR1 | ENSCAFT00000018084.3 | chr26:185334844C>G | | c.1006C>G | p.Leu336Val | Missense variant | 6% |
| OSU431895 | SF11 | ENSCAFT00000049951.2 | chr26:245020910>A | | c.3778G>A | p.Glu1260Lys | Missense variant | 14% |
| OSU431895 | PCDH15 | ENSCAFT00000024635.3 | chr26:345665885C>T | | c.4160C>T | p.Pro1387Leu | Missense variant | 15% |
| OSU431895 | PPHLN1 | ENSCAFT00000046129.1 | chr27:115716940>G | | c.241G>C | p.Asp81His | Missense variant | 27% |
| OSU431895 | MAP3K12 | ENSCAFT00000011109.3 | chr27:1731327C>G | | c.997C>G | p.Leu333Val | Missense variant | 6% |
| OSU431895 | CCDC91 | ENSCAFT00000017424.3 | chr27:19461973C>T | | c.461G>A | p.Arg154Lys | Missense variant | 34% |

FIG. 10E

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| OSU431895 | CASC1 | ENSCAFT00000018157.4 | chr27:22364318G>A | | c.838G>A | p.Glu280Lys | Missense variant | 29% |
| OSU431895 | CLEC9A | ENSCAFT00000021464.2 | chr27:35920820G>C | | c.472-4C>G | | Splice region variant | 29% |
| OSU431895 | DDX11 | ENSCAFT00000024894.3 | chr27:42079676G>C | | c.357C>G | p.Gln119His | Missense variant | 19% |
| OSU431895 | B4GALNT3 | ENSCAFT00000025016.4 | chr27:42598333T>TATGG | | c.729_2730insATt | p.Met910fs | Frameshift variant | 32% |
| OSU431895 | SEMA4G | ENSCAFT00000015460.4 | chr28:13667893G>A | | c.813+3G>A | | Splice region variant | 23% |
| OSU431895 | PPRC1 | ENSCAFT00000015971.4 | chr28:14677374G>GC | | c.2798dupC | p.Pro934fs | Frameshift variant | 29% |
| OSU431895 | CHAT | ENSCAFT00000010762.4 | chr28:15286602C>G | | c.2070C>G | p.Phe690Leu | Missense variant | 19% |
| OSU431895 | PCGF6 | ENSCAFT00000044220.2 | chr28:15733030G>A | | c.68C>T | p.Pro23Leu | Missense variant | 21% |
| OSU431895 | ENSCAFG00000068847 | ENSCAFT00000011021.4 | chr28:19166659C>T | | c.2984C>T | p.Ser995Phe | Missense variant | 20% |
| OSU431895 | PNLIPRP1 | ENSCAFT00000018834.2 | chr28:27169312G>C | | c.306G>C | p.Glu102Asp | Missense variant | 28% |
| OSU431895 | PTPRE | ENSCAFT00000021005.3 | chr28:36867151G>A | | c.532G>A | p.Glu178Lys | Missense variant | 7% |
| OSU431895 | ENSCAFG00000013695 | ENSCAFT00000021723.3 | chr28:40788958G>C | | c.676G>C | p.Ala226Pro | Missense variant | 42% |
| OSU431895 | SGK3 | ENSCAFT00000011773.3 | chr29:163449963G>C | | c.69C>G | p.Lys23Asn | Missense variant | 27% |
| OSU431895 | ZFHX4 | ENSCAFT00000013195.4 | chr29:24832205C>T | | c.4735C>T | p.Pro1579Ser | Missense variant | 17% |
| OSU431895 | CPNE3 | ENSCAFT00000014109.2 | chr29:32727523C>G | | c.1580C>G | p.Pro527Arg | Missense variant | 18% |
| OSU431895 | EDIL3 | ENSCAFT00000013454.1 | chr3:237115111A>G | | c.652-2A>G | | Splice acceptor variant | 9% |
| OSU431895 | POLK | ENSCAFT00000014935.3 | chr3:307988334G>C | | c.1731C>G | p.Phe577Leu | Missense variant | 25% |
| OSU431895 | HOMER2 | ENSCAFT00000020916.3 | chr3:54661523C>G | | c.895G>C | p.Glu299Gln | Missense variant | 34% |
| OSU431895 | ARAP2 | ENSCAFT00000025668.3 | chr3:75726700C>G | | c.2723C>G | p.Ser908Cys | Missense variant | 29% |
| OSU431895 | PPIP5K2 | ENSCAFT00000012054.4 | chr3:8082899C>G | | c.17C>C | p.Arg6Thr | Missense variant | 21% |
| OSU431895 | RNF111 | ENSCAFT00000026314.3 | chr30:24024406GAC>G | | c.2786_2787delC | p.Thr929fs | Frameshift variant | 23% |
| OSU431895 | EIF2AK4 | ENSCAFT00000014032.4 | chr30:71693333G>C | | c.1602G>C | p.Leu534Phe | Missense variant | 21% |
| OSU431895 | INO80 | ENSCAFT00000015097.3 | chr30:81189159G>C | | c.3510-6C>G | | Splice region variant | 33% |
| OSU431895 | NRIP1 | ENSCAFT00000012894.3 | chr31:11858097G>A | | c.1301C>T | p.Ser434Phe | Missense variant | 22% |
| OSU431895 | ENSCAFG00000029964 | ENSCAFT00000046703.1 | chr31:37278435G>C | | c.2336G>C | p.Arg779Thr | Missense variant | 22% |
| OSU431895 | PTPN13 | ENSCAFT00000014995.3 | chr32:102603336G>C | | c.2377G>C | p.Gly793Arg | Missense variant | 26% |
| OSU431895 | TRMT10C | ENSCAFT00000048115.1 | chr33:7948899TTAGA>T | | c.1016_1019delGA | p.Arg339fs | Frameshift variant | 27% |
| OSU431895 | IRX4 | ENSCAFT00000016576.3 | chr34:10928929G>C | | c.714C>G | p.Glu238Asp | Missense variant | 22% |
| OSU431895 | CCDC127 | ENSCAFT00000017573.3 | chr34:11975238C>G | | c.533C>G | p.Ser178Cys | Missense variant | 24% |
| OSU431895 | PEX5L | ENSCAFT00000018246.2 | chr34:131995370C>A | | c.994G>T | p.Asp332Tyr | Missense variant | 17% |
| OSU431895 | PEX5L | ENSCAFT00000018248.2 | chr34:132924210C>A | | c.97C>T | p.Glu33* | Stop-gained variant | 25% |
| OSU431895 | SI | ENSCAFT00000022936.3 | chr34:30322770G>A | | c.3631-8C>T | | Splice region variant | 22% |
| OSU431895 | DLX1 | ENSCAFT00000020533.3 | chr36:164877866G>A | | c.648G>A | p.Trp216* | Stop-gained variant | 24% |
| OSU431895 | HOXD10 | ENSCAFT00000021329.3 | chr36:199267916>C | | c.1014G>C | p.Lys338Asn | Missense variant | 15% |
| OSU431895 | METTL21A | ENSCAFT00000042739.1 | chr37:16001841G>T | | c.103C>A | p.Gln35Lys | Missense variant | 23% |
| OSU431895 | USH2A | ENSCAFT00000017072.3 | chr38:114781108C>T | | c.5017G>A | p.Glu1673Lys | Missense variant | 27% |
| OSU431895 | DISP1 | ENSCAFT00000018051.3 | chr38:237183544G>T | | c.2562C>A | p.Phe854Leu | Missense variant | 25% |
| OSU431895 | LRRTM3 | ENSCAFT00000043912.1 | chr4:18322023C>G | | c.83C>G | p.Ser28Cys | Missense variant | 14% |
| OSU431895 | AIFM2 | ENSCAFT00000022236.3 | chr4:21089398G>A | | c.968C>T | p.Pro323Leu | Missense variant | 18% |
| OSU431895 | MCU | ENSCAFT00000023057.4 | chr4:234968986G>A | | c.508G>A | p.Glu170Lys | Missense variant | 15% |
| OSU431895 | LRIT1 | ENSCAFT00000025227.3 | chr4:32476147G>A | | c.560C>T | p.Ala187Val | Missense variant | 46% |
| OSU431895 | SYNPO | ENSCAFT00000028748.2 | chr4:58504820G>T | | c.1297C>A | p.Leu433Met | Missense variant | 18% |
| OSU431895 | PPARGC1B | ENSCAFT00000029039.4 | chr4:59184211C>G | | c.2102G>C | p.Gly701Ala | Missense variant | 21% |

FIG. 10F

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| OSU431895 | CDH10 | ENSCAFT00000030188.3 | chr4:81100231G>T | | c.1984G>T | p.Gly662Cys | Missense variant | 50% |
| OSU431895 | ACTA1 | ENSCAFT00000013094.3 | chr4:98139995G>A | | c.802G>A | p.Asp268Asn | Missense variant | 55% |
| OSU431895 | TP53 | ENSCAFT00000026465.3 | chr5:32564571C>T | | c.338G>A | p.Trp113* | Stop-gained variant | 36% |
| OSU431895 | TEKT3 | ENSCAFT00000028445.3 | chr5:38884781G>C | | c.884C>G | p.Ser295* | Stop-gained variant | 21% |
| OSU431895 | LRRC75A | ENSCAFT00000028610.3 | chr5:39486746G>A | | c.661G>A | p.Glu221Lys | Missense variant | 28% |
| OSU431895 | C1orf168 | ENSCAFT00000043811.2 | chr5:52680875G>T | | c.4G>T | p.Glu2* | Stop-gained variant | 7% |
| OSU431895 | TTC22 | ENSCAFT00000043914.2 | chr5:54379139C>G | | c.1226C>G | p.Thr409Arg | Missense variant | 31% |
| OSU431895 | ARHGAP32 | ENSCAFT00000016281.3 | chr5:56562680C>G | | c.1238C>G | p.Ser413Cys | Missense variant | 32% |
| OSU431895 | MYLPF | ENSCAFT00000026205.3 | chr6:17721053G>C | | c.79C>G | p.Gln27Glu | Missense variant | 28% |
| OSU431895 | USP31 | ENSCAFT00000028068.3 | chr6:22652611C>A | | c.677C>A | p.Ser226Tyr | Missense variant | 23% |
| OSU431895 | USP31 | ENSCAFT00000028068.3 | chr6:22662881C>G | | c.1120C>G | p.Leu374Val | Missense variant | 4% |
| OSU431895 | DNASE1 | ENSCAFT00000030587.3 | chr6:37599193C>G | | c.111G>C | p.Lys37Asn | Missense variant | 22% |
| OSU431895 | NAA60 | ENSCAFT00000030602.3 | chr6:37768888C>G | | c.64G>C | p.Asp22His | Missense variant | 12% |
| OSU431895 | CLCA4 | ENSCAFT00000032245.3 | chr6:61560679C>G | | c.2152G>C | p.Glu718Gln | Missense variant | 32% |
| OSU431895 | PROX1 | ENSCAFT00000019756.3 | chr7:12043975G>C | | c.2214G>C | p.Ter738Tyr | Stop-lost variant | 15% |
| OSU431895 | HMCN1 | ENSCAFT00000021686.3 | chr7:19225514T>G | | c.15040T>G | p.Tyr5014Asp | Missense variant | 25% |
| OSU431895 | ENSCAFG00000015015 | ENSCAFT00000023838.3 | chr7:28268707C>G | | c.1059C>G | p.Phe353Leu | Missense variant | 25% |
| OSU431895 | ADCY10 | ENSCAFT00000024423.3 | chr7:30619392G>C | | c.2301G>C | p.Lys767Asn | Missense variant | 20% |
| OSU431895 | POGK | ENSCAFT00000024738.3 | chr7:31535670C>T | | c.1421G>A | p.Arg474His | Missense variant | 27% |
| OSU431895 | ARHGEF11 | ENSCAFT00000026393.3 | chr7:41096724G>T | | c.4490G>T | p.Arg1497Ile | Missense variant | 14% |
| OSU431895 | ENSCAFG00000016616 | ENSCAFT00000026393.3 | chr7:41397488C>A | | c.981+3C>A | | Splice region variant | 27% |
| OSU431895 | DSG3 | ENSCAFT00000026690.2 | chr7:58064476G>C | | c.565C>G | p.Leu189Val | Missense variant | 5% |
| OSU431895 | ENSCAFG00000014787 | ENSCAFT00000023469.4 | chr7:59636317A>G | rs852402061 | c.269T>C | p.Cys97Arg | Missense variant | 38% |
| OSU431895 | OSBPL1A | ENSCAFT00000022395.3 | chr7:64217266G>C | | c.2611G>C | p.Asp871His | Missense variant | 5% |
| OSU431895 | CLUL1 | ENSCAFT00000029136.4 | chr7:67477272G>A | | c.931G>A | p.Glu311Lys | Missense variant | 23% |
| OSU431895 | MIS18BP1 | ENSCAFT00000022361.4 | chr8:22653837G>A | | c.1346C>T | p.Ser449Phe | Missense variant | 19% |
| OSU431895 | ZBTB1 | ENSCAFT00000043977.1 | chr8:38950418G>T | | c.149G>T | p.Arg50Ile | Missense variant | 24% |
| OSU431895 | ELMSAN1 | ENSCAFT00000026701.4 | chr8:46997477G>A | | c.1016C>T | p.Ser339Phe | Missense variant | 22% |
| OSU431895 | NRXN3 | ENSCAFT00000043139.1 | chr8:51608485C>G | | c.2094C>G | p.Phe698Leu | Missense variant | 20% |
| OSU431895 | SERPINA6 | ENSCAFT00000027978.3 | chr8:63335846C>T | | c.76G>A | p.Asp26Asn | Missense variant | 19% |
| OSU431895 | SYNE3 | ENSCAFT00000028095.3 | chr8:64304289C>T | | c.1278G>A | p.Met426Ile | Missense variant | 4% |
| OSU431895 | ATP6V0A1 | ENSCAFT00000023874.3 | chr9:20460130C>G | | c.457G>C | p.Asp153His | Missense variant | 20% |
| OSU431895 | MYCBPAP | ENSCAFT00000027070.4 | chr9:26473031G>C | | c.1902G>C | p.Trp634Cys | Missense variant | 17% |
| OSU431895 | COX11 | ENSCAFT00000027487.2 | chr9:30079609C>G | | c.225G>C | p.Glu75Asp | Missense variant | 27% |
| OSU431895 | MED13 | ENSCAFT00000028033.3 | chr9:34722633C>G | | c.3663C>G | p.Ser1288Cys | Missense variant | 17% |
| OSU431895 | SEPT9 | ENSCAFT00000006383.4 | chr9:35048560C>G | | c.1159G>C | p.Glu387Gln | Missense variant | 21% |
| OSU431895 | HEATR6 | ENSCAFT00000028841.3 | chr9:37581109C>A | | c.2851G>T | p.Glu951* | Stop-gained variant | 22% |
| OSU431895 | MYO1D | ENSCAFT00000029185.3 | chr9:40171560T>A | | c.74T>A | p.Phe25Tyr | Missense variant | 13% |
| OSU431895 | SMG6 | ENSCAFT00000028083.3 | chr9:46402831G>C | | c.385C>G | p.Leu129Val | Missense variant | 23% |
| OSU431895 | LRRC26 | ENSCAFT00000031014.3 | chr9:48491434C>T | | c.440C>T | p.Ser147Phe | Missense variant | 20% |
| OSU431895 | NPDC1 | ENSCAFT00000031030.3 | chr9:48599176G>C | | c.125G>C | p.Cys42Ser | Missense variant | 20% |
| OSU431895 | HMCN2 | ENSCAFT00000031743.4 | chr9:53491794G>C | | c.14144-4C>G | | Splice region variant | 24% |
| OSU431895 | PBX3 | ENSCAFT00000032127.3 | chr9:57200010C>T | | c.1042G>A | p.Glu348Lys | Missense variant | 21% |

FIG. 10G

| Patient ID | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|
| OSU431895 | FAM120C | ENSCAFT00000047380.2 | chrX:45984653T>A | | c.2524-2A>T | | Splice acceptor variant | 56% |
| OSU431895 | GNL3L | ENSCAFT00000026083.3 | chrX:46294904A>G | | c.1736A>G | p.Asn579Ser | Missense variant | 51% |
| OSU431895 | ENSCAFG00000017103 | ENSCAFT00000043925.2 | chrX:55730703G>C | | c.4635+1G>C | | Splice donor variant | 48% |

FIG. 10H

Supplementary Table 5. Somatic copy number variants identified by exome sequencing in primary canine lung cancers.

| Patient ID | Region | Mutation type | Log2 ratio | Number of genes | Gene symbols |
|---|---|---|---|---|---|
| CCB010387 | chr6:16860700-16899200 | Deletion | -1.6779 | 2 | ENSCAFG00000014312,ITGAX |
| CCB010387 | chr11:41162150-41570250 | Deletion | -1.8457 | 5 | ENSCAFG00000001671,CDKN2A,CDKN2B,CDKN2B-AS,DMRTA1 |
| CCB050227 | chr1:101586650-101590100 | Deletion | -1.0814 | 1 | ZNF583 |
| CCB050227 | chr1:114616500-114618000 | Deletion | -1.0175 | 1 | GGN |
| CCB050227 | chr1:115950650-115971150 | Deletion | -1.1607 | 1 | ZNF568 |
| CCB050227 | chr1:126225C-1351300 | Deletion | -1.0325 | 1 | ATP9B |
| CCB050227 | chr1:13653250-13568550 | Deletion | -1.0799 | 1 | VPS4B |
| CCB050227 | chr1:145879CC-14652700 | Deletion | -1.1356 | 1 | KIAA1468 |
| CCB050227 | chr1:244702S0-24495400 | Deletion | -1.052 | 1 | ENSCAFG00000000172 |
| CCB050227 | chr1:68139500-68149900 | Deletion | -1.1038 | 1 | TJP2 |
| CCB050227 | chr5:166236C0-16656850 | Deletion | -1.0154 | 1 | SIK3 |
| CCB050227 | chr5:50042500-50060250 | Deletion | -1.1865 | 1 | HOOK1 |
| CCB050227 | chr5:60028150-60046500 | Deletion | -1.1114 | 1 | NFAT5 |
| CCB050227 | chr5:80637850-80668100 | Deletion | -1.1047 | 1 | TANGO6 |
| CCB050227 | chr5:82027000-82066250 | Deletion | -1.0096 | 1 | LRRC36 |
| CCB050227 | chr11:134007C0-134453950 | Deletion | -1.1525 | 1 | CSNK1G3 |
| CCB050227 | chr11:34502800-34603350 | Deletion | -1.0815 | 1 | NFIB |
| CCB050227 | chr11:53633600-53683150 | Deletion | -1.0852 | 1 | ZCCHC7 |
| CCB050227 | chr20:16807200-16813950 | Deletion | -1.0215 | 1 | CHL1 |
| CCB050227 | chr20:54977850-55215750 | Deletion | -1.0239 | 1 | TMCC1 |
| CCB050227 | chr20:60533750-60711150 | Deletion | -1.0576 | 1 | TSEN2 |
| CCB050227 | chr25:14121350-14153400 | Deletion | -1.1147 | 1 | NUPL1 |
| CCB050227 | chr25:23987000-24141250 | Deletion | -1.1921 | 1 | SCRG1 |
| CCB050227 | chr25:53773S0-54155S0 | Deletion | -1.2073 | 1 | NBEA |
| CCB050227 | chr26:166366S0-16760250 | Deletion | -1.0642 | 1 | SPPL3 |
| CCB050227 | chr26:23276850-23287100 | Deletion | -1.0595 | 1 | HORMAD2 |
| CCB050227 | chr28:129494C0-12961350 | Deletion | -1.1368 | 1 | ERLIN1 |
| CCB050227 | chr28:16317950-16344200 | Deletion | -1.1552 | 1 | SLK |
| CCB050227 | chr28:16528300-16554600 | Deletion | -1.0746 | 1 | WDR96 |
| CCB050227 | chr28:25605300-25628800 | Deletion | -1.0107 | 1 | FAM160B1 |
| CCB050227 | chr28:63447CO-63521100 | Deletion | -1.1796 | 1 | TNKS2 |
| CCB050227 | chr28:99386900-9970060C | Deletion | -1.1972 | 1 | TM9SF3 |
| CCB050227 | chr1:104802000-104871300 | Deletion | -1.0366 | 2 | ZNF677,ENSCAFG00000030568 |
| CCB050227 | chr1:115014800-115040300 | Deletion | -1.0106 | 2 | WDR87,ENSCAFG00000005986 |
| CCB050227 | chr1:117852000-117918100 | Deletion | -1.0193 | 2 | WTIP,UBA2 |
| CCB050227 | chr1:118064500-118424400 | Deletion | -1.0721 | 2 | LSM14A,KCTD15 |
| CCB050227 | chr1:57669100-57755450 | Deletion | -1.243 | 2 | ROS1,DCBLD1 |
| CCB050227 | chr1:60692600-60847950 | Deletion | -1.117 | 2 | TBC1D32,U4 |
| CCB050227 | chr1:93409500-93472450 | Deletion | -1.1313 | 2 | JAK2,INSL6 |
| CCB050227 | chr5:12766050-12861800 | Deletion | -1.0626 | 2 | SC5D,TECTA |
| CCB050227 | chr5:13533650-13675900 | Deletion | -1.0241 | 2 | ARHGEF12,TMEM136 |
| CCB050227 | chr5:22311300-22332900 | Deletion | -1.0314 | 2 | ARHGAP20,ENSCAFG00000014234 |

FIG. 11A

| Patient ID | Region | Mutation type | Log2 ratio | Number of genes | Gene symbols |
|---|---|---|---|---|---|
| CCB050227 | chr5:22572050-22826450 | Deletion | -1.177 | 2 | RDX,ENSCAFG00000030803 |
| CCB050227 | chr5:39611050-39791800 | Deletion | -1.0144 | 2 | PIGL,NCOR1 |
| CCB050227 | chr5:75323800-75466400 | Deletion | -1.0383 | 2 | BCAR1,P97 |
| CCB050227 | chr5:76498150-76518750 | Deletion | -1.0017 | 2 | SF3B3,SNORD111 |
| CCB050227 | chr6:15222200-15245050 | Amplification | 0.5121 | 2 | PAX9,SLC25A21 |
| CCB050227 | chr8:24675500-25005850 | Amplification | 0.607 | 2 | ENSCAFG00000030425,ENSCAFG00000014169 |
| CCB050227 | chr8:30604100-30734800 | Deletion | 0.555 | 2 | SAMD4A,GCH1 |
| CCB050227 | chr8:43099450-43211550 | Amplification | 0.6235 | 2 | GALNT16,ERH |
| CCB050227 | chr8:50628500-50964200 | Amplification | 0.7957 | 2 | ADCK1,ENSCAFG00000017256 |
| CCB050227 | chr8:59710850-59726350 | Deletion | 0.5688 | 2 | SPATA7,PTPN21 |
| CCB050227 | chr9:40851600-40727650 | Amplification | 0.5736 | 2 | RHBDL3,RHOT1 |
| CCB050227 | chr9:49620900-49635200 | Amplification | 0.6816 | 2 | ENSCAFG00000019749,LCN9 |
| CCB050227 | chr11:37273900-37759000 | Deletion | -1.0549 | 2 | CNTLN,SH3GL2 |
| CCB050227 | chr11:45666650-45998200 | Deletion | -1.1213 | 2 | C9orf72,U6 |
| CCB050227 | chr11:50641550-50681000 | Deletion | -1.1092 | 2 | UBE2R2,UBAP2 |
| CCB050227 | chr11:51683900-51838300 | Deletion | -1.0625 | 2 | FAM214B,UNC13B |
| CCB050227 | chr11:59243050-59630000 | Deletion | -1.1042 | 2 | CYLC2,ENSCAFG00000030806 |
| CCB050227 | chr11:66259850-66356900 | Deletion | -1.0879 | 2 | DNAJC25,C9orf84 |
| CCB050227 | chr11:19122650-19193700 | Deletion | -1.1216 | 2 | PPP4R2,GXYLT2 |
| CCB050227 | chr20:87836000-9056800 | Deletion | -1.0515 | 2 | THUMPD3,SRGAP3 |
| CCB050227 | chr20:91833300-9359800 | Deletion | -1.0094 | 2 | RAD18,OXTR |
| CCB050227 | chr25:31211750-31478850 | Deletion | -1.2779 | 2 | PPP2R2A,EBF2 |
| CCB050227 | chr25:34763150-34859650 | Deletion | -1.1124 | 2 | PPP3CC,SLC39A14 |
| CCB050227 | chr26:14606350-14716700 | Deletion | -1.073 | 2 | TAOK3,SUDS3 |
| CCB050227 | chr26:31044900-31132600 | Deletion | -1.0995 | 2 | MAPK1,ENSCAFG00000015433 |
| CCB050227 | chr26:91211150-9226900 | Deletion | -1.2128 | 2 | ATXN2,BRAP |
| CCB050227 | chr28:2385200-2443800 | Deletion | -1.0395 | 2 | ENSCAFG00000025080,ZNF22 |
| CCB050227 | chr28:29967400-30011800 | Deletion | -1.125 | 2 | C10ORF119,SEC23IP |
| CCB050227 | chr1:100189600-100251600 | Deletion | -1.0589 | 3 | ENSCAFG00000029340,ENSCAFG00000002408,ENSCAFG00000028494 |
| CCB050227 | chr1:108762600-108875300 | Deletion | -1.0459 | 3 | ZC3H4,SAE1,U6 |
| CCB050227 | chr1:31181550-31363550 | Deletion | -1.1872 | 3 | ENSCAFG00000000279,ABRACL,HECA |
| CCB050227 | chr8:39141750-39307050 | Amplification | 0.6613 | 3 | PLEKHG3,SPTB,CHURC1 |
| CCB050227 | chr8:50039400-50117050 | Amplification | 0.6604 | 3 | TMEM63C,NGB,POMT2 |
| CCB050227 | chr8:50142700-50162850 | Amplification | 0.5886 | 3 | GSTZ1,TMED8,SAMD15 |
| CCB050227 | chr9:26660200-26737000 | Amplification | 0.625 | 3 | ENSCAFG00000028954,WFIKKN2,TOB1 |
| CCB050227 | chr11:26772200-26905000 | Deletion | -1.1166 | 3 | MATR3,5_8S_rRNA,MLANA |
| CCB050227 | chr11:52696650-53066800 | Deletion | -1.0224 | 3 | GNE,RNF38,MELK |
| CCB050227 | chr11:124870500-12643600 | Deletion | -1.1602 | 3 | ARL6B,U6,BHLHE40 |
| CCB050227 | chr20:25130300-25315200 | Deletion | -1.2147 | 3 | SLC25A26,SNORA64,ENSCAFG00000030398 |
| CCB050227 | chr20:48455100-48457500 | Deletion | -1.0294 | 3 | C19orf57,PALM3,IL27RA |
| CCB050227 | chr25:11442900-11617250 | Deletion | -1.0477 | 3 | PAN3,U2,FLT3 |
| CCB050227 | chr25:26545700-26716350 | Deletion | -1.0077 | 3 | ENSCAFG00000008016,MTMR9,ENSCAFG00000030648 |
| CCB050227 | chr28:136093300-13667850 | Deletion | -1.0149 | 3 | FAM178A,U2,SEMA4G |

FIG. 11B

| Patient ID | Region | Mutation type | Log2 ratio | Number of genes | Gene symbols |
|---|---|---|---|---|---|
| CCB050227 | chr28:26978900-27145400 | Deletion | -1.068 | 3 | CCDC172,5S_rRNA,PNLIP |
| CCB050227 | chr28:8624500-8738150 | Deletion | -1.1155 | 3 | TBC1D12,HELLS,CYP2C21 |
| CCB050227 | chr1:106859600-106876300 | Deletion | -1.0013 | 4 | PRMT1,U4,BCL2L12,IRF3 |
| CCB050227 | chr1:48848500-49011800 | Deletion | -1.0667 | 4 | SOD2,ENSCAFG00000023207,U6atac,ACAT2 |
| CCB050227 | chr5:39245200-39386800 | Deletion | -1.0097 | 4 | ENSCAFG00000031764,5S_rRNA,ZNF624,ZNF287 |
| CCB050227 | chr5:55863850-55996900 | Deletion | -1.0411 | 4 | PODN,SCP2,HES4,ZYG11A |
| CCB050227 | chr9:35169500-35405000 | Amplification | 0.5976 | 4 | TBX4,ENSCAFG00000017742,TBX2,BCAS3 |
| CCB050227 | chr1:66765850-66883100 | Deletion | -1.1198 | 4 | PTBP3,ENSCAFG00000032333,ENSCAFG00000003019,HSDL2 |
| CCB050227 | chr1:70052650-70308350 | Deletion | -1.0307 | 5 | ZNF782,ZNF510,AAED1,ENSCAFG00000030594,CDC14B |
| CCB050227 | chr8:49368700-49674550 | Amplification | 0.7291 | 5 | ESRRB,7SK,ENSCAFG00000004150,VASH1,ANGEL1 |
| CCB050227 | chr9:43672450-43745900 | Amplification | 0.5282 | 5 | TP53I13,GIT1,ANKRD13B,CORO6,SSH2 |
| CCB050227 | chr9:41103200-41486150 | Amplification | 0.5367 | 6 | COPRS,U6,cfa-mir-365-2,cfa-mir-193a,RAB11FIP4,NF1 |
| CCB050227 | chr9:60349750-61040500 | Amplification | 0.5766 | 6 | LHX6,MORN5,NDUFA8,TTLL11,DAB2IP,GGTA1 |
| CCB050227 | chr26:6793950-7092600 | Deletion | -1.0275 | 6 | KNTC1,RSRC2,ZCCHC8,SNORA9,CLIP1,ENSCAFG00000007919 |
| CCB050227 | chr9:46063700-46384700 | Amplification | 0.5435 | 7 | RTN4RL1,DPH1,cfa-mir-132,cfa-mir-212,HIC1,U6,SMG6 |
| CCB050227 | chr11:45083850-45278650 | Deletion | -1.0307 | 7 | CAAP1,PLAA,IFT74,LRRC19,cfa-mir-872,U6,TEK |
| CCB050227 | chr9:30742000-40052500 | Amplification | 0.565 | 9 | TNRC6C,ENSCAFG00000031705,ENSCAFG00000030116,SEPT9,SEC14L1,ENSCAFG00000031523,SC ARNA16,MGAT5B,MFSD11 |
| CCB050227 | chr9:54720850-54897300 | Amplification | 0.5341 | 10 | CRAT,PHYHD1,LRRC8A,CCBL1,C9orf114,ENDOG,TBC1D13,ZER1,ZDHHC12,PKN3 |
| CCB050227 | chr9:58444650-58930100 | Amplification | 0.5732 | 10 | NR6A1,U6,SF1,GPR144,PSMB7,NEK6,ENSCAFG00000031433,LHX2,DENND1A,ENSCAFG00000003064 2 |
| CCB050227 | chr9:42927400-43374900 | Amplification | 0.5401 | 13 | TLCD1,NEK8,TRAF4,FAM222B,cfa-mir-451,cfa-mir-451,cfa-mir-144,FLOT2,PHF12,SEZ6,PIPOX,MYO18A,CRYBA3 |
| CCB050227 | chr11:40300200-41570200 | Deletion | -2.6435 | 14 | FOCAD,cfa-mir-491,U6,SNORA30,PTPLAD2,IFNB1,ENSCAFG00000023674,IFNE,cfa-mir-31,TRAF3,AMN,CDC42BPB,ENSCAFG00000018184,ENSCAFG00000032097,ENSCAFG00000003273 |
| CCB050227 | chr9:53936050-54686900 | Amplification | 0.5133 | 21 | FNBP1,U6,USP20,ENSCAFG00000019979,TOR1A,ENSCAFG00000032504,TOR1B,ENSCAFG00000030 536,PTGES,PRRX2,Y_RNA,ASB6,NTMT1,ENSCAFG00000019987,IER5L,PPP2R4,CRAT,DOLPP1,FAM7 3B,SH3GLB2,ENSCAFG00000020013 |
| CCB050227 | chr8:70013700-71225650 | Amplification | 0.535 | 24 | DYNC1H1,ENSCAFG00000001671,CDKN2A,CDKN2B,CDKN2B-AS,DMRTA1 2,TNFAIP2,ENSCAFG00000018194,EIF5,SNORA28,MARK3,U2,U4 COR1,TRAF3,AMN,CDC42BPB,ENSCAFG00000018184,ENSCAFG00000028938,ITGA3,SAMD14,PDK2,PPP1R9B,S NTNG2,MED27,SNORA63,RAPGEF1,PRRC2B,UCK1,POMT1,SNORD62,SNORD62,PPAPDC3,FAM78A, NUP214,U6,AIF1L,ENSCAFG00000028859,LAMC3,FIBCD1,QRFP,ABL1,EXOSC2,PRDM12,FUBP3,LAM |
| CCB050227 | chr9:51995100-53770350 | Amplification | 0.5779 | 27 | TOR5,ASS1,HMCN2,NCS1,GPR107 SLC35B1,FAM117A,KAT7,TAC4,DLX4,DLX3,ENSCAFG00000028938,ITGA3,SAMD14,PDK2,PPP1R9B,S GCA,ENSCAFG00000017016,COL1A1,snoU2_19,snoU2-30,TMEM92,ENSCAFG00000017025,XYLT2,MRPL27,EME1,LRRC59,ACSF2,CHAD,MYCBPAP,EPN3,CA |
| CCB050227 | chr9:25772300-26604200 | Amplification | 0.5339 | 29 | CNA1G,ABCC3,ANKRD40 |
| CCB050227 | chr9:4029500-4879850 | Amplification | 0.5243 | 42 | ENSCAFG00000005147,METTL23,JMJD6,ST6GALNAC1,ST6GALNAC2,snoR38,ENSCAFG00000 0030147,PRCD,CYGB,RHBDF2,AANAT,UBE2O,SPHK1,ENSCAFG00000028615,ENSCAFG00000033156 6,PRPSAP1,RNaseP_nuc,QRICH2,RNF157,FOXJ1,EXOC7,ZACN,GALR2,SRP68,ENSCAFG00000000502 1,CDK3,TEN1,ACOX1,FBF1,MRPL38,TRIM65,TRIM47,WBP2,UNC13D,UNK,U4,H3F3B,GALK1,ENSCAF G00000029346,ENSCAFG00000004905,SAP30BP |

FIG. 11C

| Patient ID | Region | Mutation type | Log2 ratio | Number of genes | Gene symbols |
|---|---|---|---|---|---|
| CCB050227 | chr9:49635400-51859600 | Amplification | 0.6491 | 55 | LCN9,GLT6D1,ENSCAFG00000019754,ENSCAFG00000019755,LCN1,ABO,SURF6,MED22,REXO4,ADAMTS13,CACFD1,SLC2A6,TMEM8C,ADAMTSL2,ENSCAFG00000017680,SNORD24,SNORD36,SNORD36,SURF1,SURF2,SURF4,C9orf96,REXO4,ADAMTS13,CACFD1,SLC2A6,TMEM8C,ADAMTSL2,ENSCAFG00000031627,DBH,SARDH,VAV2,U6,BRD3,U6,WDR5,RXRALPHA,ENSCAFG00000026559,COL5A1,ENSCAFG00000030630,OLFM1,PPP1R26,ENSCAFG00000032136,MRPS2,ENSCAFG00000031966,ENSCAFG00000019863,GBGT1,RALGDS,CEL,GTF3C5,GFI1B,MDH2,TSC1,C9ORF9,AK8,GTF3C4,BARHL1,C9orf171,TTF1 |
| CCB050227 | chr8:71438200-74292900 | Amplification | 0.6229 | 61 | ENSCAFG00000018285,XRCC3,ZFYVE21,PPP1R13B,U6,RD3L,TDRD9,ASPG,cfa-mir-203,KIF26A,ENSCAFG00000030362,U1,ENSCAFG00000029088,C14orf180,TMEM179,ENSCAFG00000029862,ENSCAFG00000031878,INF2,ENSCAFG00000026959,ADSSL1,AKT1,ZBTB42,CEP170B,PLD4,ENSCAFG00000030682,ENSCAFG00000030662,C14orf79,CDCA4,GPR132,JAG2,NUDT14,BRF1,BTBD6,PACS2,TEX22,MTA1,CRIP2,ENSCAFG00000018440,ENSCAFG00000031417,C14orf80,TMEM121,ENSCAFG00000032358,ENSCAFG00000029687,IGHE,ENSCAFG00000030258,RPS24,ENSCAFG00000030099,3,ENSCAFG00000023944,ENSCAFG00000023480,ENSCAFG00000018468,ENSCAFG00000031078,ENSCAFG00000028509,ENSCAFG00000030284,ENSCAFG00000029996,ENSCAFG00000030894,ENSCAFG00000030001,ENSCAFG00000030900,ENSCAFG00000024111,ENSCAFG00000029299,ENSCAFG00000018499 |
| CCB050227 | chr8:49073000-9308800 | Amplification | 0.525 | 68 | SAP30BP,RECQL5,MYO15B,LLGL2,TSEN54,ENSCAFG00000030695,CASKIN2,KIAA0195,GRB2,SLC25A19,ENSCAFG00000004756,MRPS7,GGA3,NUP85,SUMO2,HN1,NT5C,ARMC7,SLC16A5,ENSCAFG00000004715,ENSCAFG00000032582,KCTD2,ENSCAFG00000004703,ICT1,CDR2L,HID1,OTOP3,USH1G,FADS6,FDXR,GRIN2C,TMEM104,NAT9,SLC9A3R1,RAB37,ENSCAFG00000004595,CD300E,ENSCAFG00000028809,ENSCAFG00000024944,ENSCAFG00000024942,ENSCAFG00000028912,ENSCAFG00000024792,CD300LB,ENSCAFG00000032631,GPRC5C,GPR142,BTBD17,ENSCAFG00000032340,KIF19,DNAI2,TTYH2,SDK2,CDC42EP4,C17orf80,FAM104A,COG1,SSTR2,SLC39A11,U6,ENSCAFG00000003158,3,ENSCAFG00000004401,SOX9,ENSCAFG00000031779,ENSCAFG00000015160,EFCAB13,GPIHA,MYL4,CDC27 |
| CCB050227 | chr8:3546450-9927850 | Amplification | 0.5262 | 77 | HOMEZ,PPP1R3E,BCL2L2,PABPN1,SLC22A17,EFS,IL25,CMTM5,cfa-mir-208a,MYH7,cfa-mir-208b,NGDN,ZFHX2,AP1G2,THTPA,DHRS2,ENSCAFG00000025298,DHRS4,LRRC16B,CPNE6,NRL,PCK2,DCAF11,FITM1,PSME1,EMC9,PSME2,ENSCAFG00000011993,IRF9,REC8,IPO4,ENSCAFG00000090120,71,TSSK4,NEDD8,GMPR2,TINF2,TGM1,RABGGTA,DHRS1,C14ORF21,CIDEB,LTB4R,ADCY4,RIPK3,U6,NFATC4,NYNRIN,CBLN3,KHNYN,7SK,SDR39U1,U6,CMA1,ENSCAFG00000025404,CTSG,GZMB,U6,STXBP6,ENSCAFG00000019805,RNaseP_nuc,U6,NOVA1,ENSCAFG00000012507,ENSCAFG00000000125,16,U6,ENSCAFG00000012522,ENSCAFG00000012527,FOXG1,U6,PRKD1,U6,ENSCAFG00000012573,G2E3 |
| CCB050227 | chr9:96600-3044550 | Amplification | 0.6024 | 91 | 0029701,U6,ENSCAFG00000028819,U6,PRKD1,U6,ENSCAFG00000012573,G2E3,CSNK1D,SLC16A3,RFNG,SNORA62,CCDC57,FASN,DUS1L,GPS1,DCXR,RAC3,LRRC45,STRA13,ASPSCR1,TSPAN10,NOTUM,MYADML2,PYCR1,MAFG,SIRT7,PCYT2,NPB,ANAPC11,ALYREF,ARHGDIA,P4HB,PPP1R27,FAM195B,GCGR,ENSCAFG00000095812,HGS,ARL16,CCDC137,OXLD1,PDE6G,NPLOC4,ENSCAFG00000030278,C17orf70,FSCN2,ACTG1,ENSCAFG00000032216,ENSCAFG00000005732,SLC38A10,C17orf89,ENTHD2,AZI1,AATK,cfa-mir-338,BAIAP2,CHMP6,RPTOR,U4,NPTX1,RNF213,ENDOV,SLC26A11,SGSH,CARD14,EIF4A3,ENSCAFG00000005596,GAA,CCDC40,TBC1D16,CBX4,CBX8,CBX2,ENPP7,Y_RNA,RBFOX3,ENGASE,C1QTNF1,CANT1,LGALS3BP,ENSCAFG00000030094,ENSCAFG00000005532,TIMP2,USP36,CYTH1,U6,DNAH17,PGS1,SOCS3,ENSCAFG00000014766,TMEM235,BIRC5,AFMID,TK1,SYNGR2,C17orf99,TMC8,TMC6,TNRC6C |

FIG. 11D

| Patient ID | Region | Mutation type | Log2 ratio | Number of genes | Gene symbols |
|---|---|---|---|---|---|
| | | | | | CLUH,ENSCAFG00000023030,RAP1GAP2,ENSCAFG00000019307,ENSCAFG00000019310,OR1A2,OR1P2,OR3A1,ENSCAFG00000032680,GNG10,ENSCAFG00000019324,ENSCAFG00000019325,DTMT,SPATA22,ASPA,TRPV3,TRPV1,SHPK,CTNS,TAX1BP3,EMC6,P2X5,ITGAE,GSG2,C17orf85,U6,CAMKK1,P2RX1,ATP2A3,CACNA1B,EHMT1,ARRDC1,ZMYND19,DPH7,MRPL41,PNPLA7,ENSCAFG00000019431,ENSCAFG00000029381,ENTPD8,NOXA1,EXD3,NRARP,TOR4A,NELFB,C9orf173,TUBB4B,FAM166A,RNF208,SLC34A3,RNF224,NDOR1,TMEM203,TPRN,TMEM210,SSNA1,LRRC26,GRIN1,ENSCAFG00000019510,ENSCAFG00000019517,DPP7,ENSCAFG00000019511,ENSCAFG00000031537,C9ORF140,ENTPD2,NPDC1,FUT7,ABCA2,CLIC3,C9orf142,LCNL1,PTGDS,LCN12,C8G,FBXW5,TRAF2,ENSCAFG00000028864,EDF1,MAMDC4,PHPT1,C9orf172,RABL6,ENSCAFG00000019559,LCN15,TMEM141,LCN8,ENSCAFG00000019563,LCN10,SNORA17,SNORA17,FAM69B,ENSCAFG00000032329,AGPAT2,NOTCH1,EGFL7,cfa-mir-126,GPSM1,SEC16A,INPP5E,PMPCA,SDCCAG3,SNAPC4,CARD9,DNL Z,ENSCAFG00000019701,QSOX2,LHX3,C9orf69,NACC2,UBAC1,CAMSAP1,KCNT1,SOHLH1,ENSCAFG00000019747,ENSCAFG000000019749 |
| CCB050227 | chr9:46737800-49619100 | Amplification | 0.5887 | 114 | TDP1,KCNK13,PSMC1,NRDE2,ENSCAFG00000032360,CALM1,TTC7B,ENSCAFG00000031748,SNORA11,RPS6KA5,GPR68,CCDC88C,SMEK1,5S_rRNA,U6,TMEM251,C14orf142,ENSCAFG00000017591,BTBD7,U6,7SK,UNC79,U6,PRIMA1,FAM181A,ASB2,ENSCAFG00000017617,OTUB2,DDX24,ENSCAFG00000017632,PPP4R4,SERPINA5,SERPINA1,SERPINA11,ENSCAFG00000017659,SERPINA12,SERPINA4,SERPINA5,SERPINA3,GSC,U6,DICER1,CLMN,SYNE3,5S_rRNA,SCARNA13,GLRX5,U6,TCL1A,ENSCAFG00000017720,ENSCAFG00000031190,BDKRB2,BDKRB1,ATG2B,GSKIP,AK7,PAPOLA,VRK1,ENSCAFG00000017806,ENSCAFG00000026793,U6,BCL11B,SETD3,CCNK,CCDC85C,HHIPL1,CYP46A1,EML1,EVL,ENSCAFG00000031475,cfa-mir-342,DEGS2,YY1,SLC25A29,cfa-mir-345,SLC25A47,WARS,MDR25,7SK,BEGAIN,DLK1,Mico1,MEG3_1,MEG3_2,SNORD112,cfa-mir-493,cfa-mir-665,cfa-mir-432,ENSCAFG00000022762,cfa-mir-433,cfa-mir-432,cfa-mir-127,cfa-mir-432,cfa-mir-136,SNORD112,cfa-mir-370,SNORD112,SNORD113,SNORD112,SNORD113,SNORD112,SNORD113,SNORD113,SNORD113,SNORD113,SNORD113,SNORD112,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,SNORD113,cfa-mir-379,cfa-mir-411,cfa-mir-299,cfa-mir-380,ENSCAFG00000030904,ENSCAFG00000026742,cfa-mir-323,cfa-mir-758,cfa-mir-329b,cfa-mir-329a,cfa-mir-494,ENSCAFG00000026797,cfa-mir-543,cfa-mir-495,ENSCAFG00000029193,cfa-mir-376,cfa-mir-376a-3,cfa-mir-376c,cfa-mir-376a-2,cfa-mir-376b,cfa-mir-376a-1,cfa-mir-300,ENSCAFG00000026682,cfa-mir-381,cfa-mir-487b,cfa-mir-539,ENSCAFG00000026524,cfa-mir-544,ENSCAFG00000025682,ENSCAFG00000031373,cfa-mir-487a,cfa-mir-382,cfa-mir-134,ENSCAFG00000030136,cfa-mir-485,ENSCAFG00000025626,cfa-mir-496,cfa-mir-377,ENSCAFG00000026548,cfa-mir-409,cfa-mir-369,cfa-mir-410,ENSCAFG00000025659,ENSCAFG00000022814,DIO3,PPP2R5C |
| CCB050354 | chr8:61037750-69966650 | Amplification | 0.5091 | 200 | PITRM1 |
| CCB050354 | chr2:32213400-32215750 | Amplification | 0.6454 | 1 | ARHGEF10L |
| CCB050354 | chr2:80725700-80748350 | Amplification | 0.6007 | 1 | LYST |
| CCB050354 | chr4:42249000-42271750 | Amplification | 0.5497 | 1 | |
| CCB050354 | chr4:57766000-57768300 | Amplification | 0.8186 | 1 | FAT2 |

FIG. 11E

| Patient ID | Region | Mutation type | Log2 ratio | Number of genes | Gene symbols |
|---|---|---|---|---|---|
| CCB050354 | chr17:2239850-2307200 | Amplification | 0.5278 | 1 | DCDC2C |
| CCB050354 | chr23:8561950-8604600 | Amplification | 0.6679 | 1 | SCN11A |
| CCB050354 | chr33:13703900-13719600 | Amplification | 0.6961 | 1 | MYH15 |
| CCB050354 | chr4:10980600-11387500 | Amplification | 0.866 | 2 | BICC1,ENSCAFG00000012382 |
| CCB050354 | chr33:31341000-31360250 | Amplification | 0.573 | 2 | LRRC15,CPN2 |
| CCB050354 | chr4:59459200-59580900 | Amplification | 0.513 | 4 | ENSCAFG00000018286,cfa-mir-145,cfa-mir-143,IL17B |
| CCB050354 | chr2:1320800-1772700 | Amplification | 0.5012 | 5 | FZD8,ENSCAFG00000023176,CCNY,7SK,CREM |
| CCB050354 | chr2:55236650-55920250 | Amplification | 0.5192 | 8 | MAP1B,MRPS27,PTCD2,5S_rRNA,ZNF366,ENSCAFG00000031745,TNPO1,FCHO2 |
| CCB050354 | chr4:74862650-75322050 | Amplification | 0.5435 | 8 | NPR3,5S_rRNA,ENSCAFG00000018679,ENSCAFG00000018881,ZFR,ENSCAFG00000027374,MTMR12,GOLPH3 |
| CCB050354 | chr4:71943650-74862350 | Amplification | 0.7323 | 28 | GLAST,ENSCAFG00000029561,RANBP3L,ENSCAFG00000031830,SKP2,LMBRD2,ENSCAFG00000023144,ENSCAFG00000032039,CAPSL,IL7R,SPEF2,U6,PRLR,AGXT2,DNAJC21,BRIX1,RAD1,TTC23L,U6,RAI14,U6,ENSCAFG00000018825,AMACR,SLC45A2,RXFP3,ADAMTS12,TARS,NPR3 |
| CCB050354 | chr4:75351000-88273150 | Amplification | 0.7176 | 29 | PDZD2,C5orf22,ENSCAFG00000031829,ENSCAFG00000018939,CDH6,ENSCAFG00000018956,U6,CDH9,ENSCAFG00000018980,7SK,CDH10,ENSCAFG00000017424,ENSCAFG00000019017,ENSCAFG00000019023,CDH12,ENSCAFG00000031957,CDH18,SNORA62,U2,7SK,RNF167,BASP1,FAM134B,MYO10,ZNF622,MARCH11,FBXL7,ENSCAFG00000019108,ANKH |
| CCB050354 | chr4:69500-4248700 | Amplification | 0.6936 | 35 | IFIT2,IFIT3,U4,IFIT1,IFIT5,ZNF248,ZNF25,ENSCAFG00000028519,ENSCAFG00000029103,ENSCAFG00000024143,U6,ZNF37A,CHRM3,ENSCAFG00000099885,ENSCAFG00000009991,ENSCAFG00000010041,MTR,U6,AC098,ZP4,RYR2,7SK,ENSCAFG00000008063,SNORA25,U6,SNORA2,ENSCAFG00000010041,MTR,U6,AC,TN2,HEATR1,LGALS8,EDARADD,ERO1LB,GPR137B,ENSCAFG00000030894,NID1,LYST |
| CCB050354 | chr23:41411650-85811200 | Amplification | 0.5057 | 40 | PDCD6IP,ENSCAFG00000030719,5S_rRNA,U6,ENSCAFG00000004734,U6,U4,ENSCAFG00000010012,ARPP21,cfa-mir-128-2,ENSCAFG00000004758,ENSCAFG00000026672,STAC,ENSCAFG00000026737,DCLK3,TRANK1,EPM2AIP1,MLH1,LRRFIP2,ENSCAFG00000029998,GOLGA4,ITGA9,cfa-mir-26a-1,VILL,PLCD1,DLEC1,ACAA1,MYD88,OXSR1,ENSCAFG00000031028,ENSCAFG00000032364,SLC22A13,SLC22A14,XYLB,ACVR2B,EXOG,RPS2,SCN5A,SCN10A,SCN11A |
| CCB050354 | chr4:57766650-59456950 | Amplification | 0.6725 | 41 | FAT2,SLC36A1,SLC36A2,SLC36A3,GM2A,ENSCAFG00000026627,CCDC69,U6,ANXA6,TNIP1,GPX3,ENSCAFG00000017961,ENSCAFG00000023257,ZNF300,U6,SMIM3,7SK,DCTN4,RBM22,MYOZ3,SYNPO,NDST1,RPS14,CD74,TCOF1,ARSI,CAMK2A,SLC6A7,CDX1,PDGFRB,CSF1R,HMGXB3,ENSCAFG00000032400,TIGD6,SLC26A2,PDE6A,PPARGC1B,cfa-mir-378,U6,ARHGEF37,ENSCAFG00000016286 |
| CCB050354 | chr4:11446750-19604000 | Amplification | 0.6615 | 45 | PHYHIPL,FAM13C,SLC16A9,CCDC6,U6,ENSCAFG00000012458,ANK3,U6,CDK1,RHOBTB1,U2,GAPDH,ENSCAFG00000012971,TMEM26,5S_rRNA,C10orf107,ARID5B,RTKN2,ZNF365,ADO,EGR2,NRBF2,JMJD1C,ENSCAFG00000026634,7SK,REEP3,CTNNA3,ENSCAFG00000013264,LRRTM3,ENSCAFG00000024412,ENSCAFG00000013277,ENSCAFG00000006036,DNAJC12,ENSCAFG00000028966,HNRNPA1L2,SIRT1,ENSCAFG00000013319,HERC4,U6,5S_rRNA,MYPN,ATOH7,PBLD,HNRNPH3,RUFY2 |
| CCB050354 | chr33:13726650-18240200 | Amplification | 0.5037 | 46 | MYH15,KIAA1524,DZIP3,7SK,TRAT1,GUCA1C,MORC1,ENSCAFG00000010327,ENSCAFG00000001033,1,ENSCAFG00000010335,PVRL3,CD96,ZBED2,PLCXD2,PHLDB2,ABHD10,TAGLN3,TMPRSS7,C3orf52,GCSAM,SLC9C1,ENSCAFG00000010493,SLC35A5,CCDC80,ENSCAFG00000010546,ENSCAFG00000025131,GTPBP8,C3orf17,ENSCAFG00000028163,BOC,WDR52,SPICE1,SIDT1,KIAA2018,NAA50,ATP6V1A,GRAMD1C,S,NORD16,ENSCAFG00000003955,ZDHHC23,KIAA1407 |

FIG. 11F

| Patient ID | Region | Mutation type | Log2 ratio | Number of genes | Gene symbols |
|---|---|---|---|---|---|
| CCB050354 | chr4:4275550-10980450 | Amplification | 0.6742 | 66 | LYST,ENSCAFG00000031911,GNG4,B3GALNT2,TBCE,GGPS1,ARID4B,RBM34,TOMM20,SNORA14,U6,ENSCAFG00000032166,IRF2BP2,TARBP1,COA6,SLC35F3,7SK,KCNK1,ENSCAFG00000011566,PCNXL2,NTPCR,5S_rRNA,ENSCAFG00000011616,SIPA1L2,DISC1,SNORA25,ENSCAFG00000030982,EGLN1,SNORD35,SPRTN,EXOC8,GNPAT,C1orf131,TRIM67,FAM89A,ARV1,TTC13,CAPN9,C1orf198,AGT,cfa-mir-1841,cfa-mir-1841,U6,PGBD5,GALNT2,ENSCAFG00000024420,URB2,TAF5L,ABCB10,NUP133,ACTA1,CCSAP,RAB4A,U6,RHOU,ENSCAFG00000012252,U6,5S_rRNA,5S_rRNA,UBE2D1,TFAM,BICC1,5S_rRNA,ENSCAFG00000027921,ENSCAFG00000032217 |
| CCB050354 | chr4:59581200-71687800 | Amplification | 0.665 | 99 | IL17B,PCYOX1L,GRPEL2,AFAP1L1,ABLIM3,U6,SH3TC2,ADRB2,HTR4,FBXO38,SPINK7,GZMK,ESM1,ENSCAFG00000008488,ENSCAFG00000018385,ENSCAFG00000031454,SNX18,HSPB3,ENSCAFG00000002726,LITAF,ARL15,FST,ENSCAFG00000018410,ENSCAFG00000026642,ENSCAFG00000001-8414,ENSCAFG00000031509,MOCS2,ITGA2,ENSCAFG00000018434,ITGA1,U2,U6,ISL1,U6,PARP8,U6,EMB,HCN1,U6,ENSCAFG00000018512,MRPS30,FGF10,SNORA54,U6,NNT,SNORA33,PAIP1,ENSCAFG00000031903,C5orf34,5S_rRNA,C5orf28,CCL28,ENSCAFG00000018572,ENSCAFG00000030435,NIM1K,ZNF131,SEPP1,CCDC152,GHR,ENSCAFG00000023056,FBXO4,C5orf51,EEF1A1,OXCT1,PLCXD3,C6,MROH2B,C7,CARD6,SNORD72,PRKAA1,TTC33,PTGER4,ENSCAFG00000018671,U6,GDNF,WDR70,ENCTOR,OSMR,ENSCAFG00000018652,LIFR,U2,EGFLAM,ENSCAFG00000018671,U6,GDNF,WDR70,ENSCAFG00000018679,SNORA67,SNORD22,NUP155,U6,SNORA30,7SK,U6,C5orf42,NIPBL |

FIG. 11G

| Patient ID | Region | Mutation type | Log2 ratio | Number of genes | Gene symbols |
|---|---|---|---|---|---|
| CCB050354 | chr4:19724800-57765800 | Amplification | 0.6697 | 336 | SLC25A16,TET1,U6,5S_rRNA,CCAR1,U6,STOX1,DDX50,DDX21,KIAA1279,U4,SRGN,VPS26A,SUPV3L1,HKDC1,HK1,TACR2,TSPAN15,NEUROG3,C10orf35,COL13A1,5S_rRNA,H2AFY2,AIFM2,TYSND1,PPA1,ENSCAFG00000014038,LRRC20,EIF4EBP2,NODAL,PALD1,PRF1,ENSCAFG00000014078,ADAMTS14,TBATA,SGPL1,PCBD1,UNC5B,SLC29A3,ENSCAFG00000014229,U2,C10orf105,C10orf54,PSAP,U6,CHST3,SPOCK2,ASCC1,ANAPC16,DDIT4,DNAJB12,MICU1,U6,ENSCAFG00000014500,MCU,OIT3,PLA2G12B,U6,ENSCAFG00000014550,P4HA1,NUDT13,ECD,FAM149B1,DNAJC9,ENSCAFG00000031286,TTC18,ANXA7,U6,MSS51,PPP3CB,USP54,MYOZ1,SYNPO2L,SEC24C,FUT11,CHCHD1,ZSWIM8,ENSCAFG00000015050,CAMK2G,PLAU,ENSCAFG00000031053,VCL,AP3M1,ADK,U6,SNORD2,snoU2-30,U6,KAT6B,ENSCAFG00000022859,ENSCAFG00000031398,SAMD8,VDAC2,COMTD1,ZNF503,C10orf11,U6,ENSCAFG00000030490,KCNMA1,U6,DLG5,POLR3A,RPS24,U6,U6,ENSCAFG00000030222,ZMIZ1,PPIF,ZCCHC24,ANXA11,TMEM254,7SK,ENSCAFG00000023232,SFTPD,ENSCAFG00000015886,7SK,1A,DYDC1,DYDC2,FAM213A,TSPAN14,SH2D4B,5S_rRNA,DNAJB6,NRG3,ENSCAFG00000015754,MAT1A,GHITM,CDHR1,LRIT2,LRIT1,ENSCAFG00000015927,RGR,ENSCAFG00000032581,CCSER2,U6,GRID1,ENSCAFG00000031941,cfa-mir-346,WAPAL,OPN4,LDB3,BMPR1A,MMRN2,ENSCAFG00000024229,SNCG,ENSCAFG00000016093,ENSCAFG00000016095,ENSCAFG00000032460,FAM35A,SYT15,GPRIN2,NPY4R,ENSCAFG00000016149,ANTXRL,ZNF488,RBP3,GDF2,GDF10,ENSCAFG00000023521,DCP2,U6,MCC,FAM193B,GRK6,DDX41,DOK3,ENSCAFG00000016333,DBN1,PRR7,F12,PFN3,SLC34A1,RGS14,LMAN2,MXD3,PRELID1,RAB24,NSD1,FGFR4,ZNF346,ENSCAFG00000016545,ENSCAFG00000026478,UIMC1,7SK,U4,HK3,UNC5A,TSPAN17,EIF4E1B,SNCB,GPRIN1,CDHR2,RNF44,FAF2,CLTB,NOP16,ARL10,cfa-mir-1271,U6,KIAA1191,SIMC1,SUB1,THOC3,CPLX2,HRH2,U6,7SK,SFXN1,DRD1,MSX2,ENSCAFG000000030421,C5orf47,CPEB4,U6,ENSCAFG00000016775,BOD1,STC2,NKX2_5,ENSCAFG00000016785,BNIP1,CREBRF,ATP6V0E1,ERGIC1,DUSP1,NEURL1B,SH3PXD2B,U6,SNORD22,UBTD2,U6,EFCAB9,STK10,5S_rRNA,FBXW11,SMIM23,FGF18,NPM1,U6,TLX3,RANBP17,U6,GABRP,KCNIP1,KCNMB1,LCP2,FOXI1,DOCK2,FAM196B,SPDL1,ENSCAFG00000017000,U6,SLIT3,cfa-mir-218-2,PANK3,RARS,WWC1,U6,TENM2,ENSCAFG00000017171,ENSCAFG00000017176,ENSCAFG000000017180,snoZ5,U6,U6,MAT2B,HMMR,NUDCD2,CCNG1,ENSCAFG00000017239,GABRA6,GABRB2,ATP10B,cfa-mir-146a,ENSCAFG00000017236,GABRA1,SLU7,C5orf54,U6,C1QTNF2,ENSCAFG00000029942,IL12B,UBLCP1,RNF145,EBF1,U6,CLINT,0000017689,U4,PWWP2A,TTC1,ADRA1B,ENSCAFG00000017274,FABP6,ENSCAFG00000017689 |
| OSU431895 | chr13:10017050-10023050 | Amplification | 0.5342 | 1 | PKHD1L1 |
| OSU431895 | chr7:12365100-12371250 | Amplification | 0.5386 | 1 | PTPN14 |
| OSU431895 | chr13:58435300-58440950 | Amplification | 0.5417 | 1 | TMPRSS11A |
| OSU431895 | chr16:6344700-6351450 | Amplification | 0.5454 | 1 | CLCN1 |
| OSU431895 | chr34:11295750-11300350 | Amplification | 0.5474 | 1 | TERT |
| OSU431895 | chr8:27340800-27357600 | Amplification | 0.5493 | 1 | TRIM9 |
| OSU431895 | chr10:45370600-45374900 | Amplification | 0.5575 | 1 | HAAO |
| OSU431895 | chr15:8168500-8183050 | Amplification | 0.5726 | 1 | CSMD2 |
| OSU431895 | chr37:14353200-14361200 | Amplification | 0.5807 | 1 | NRP2 |
| OSU431895 | chr36:10308100-10318750 | Amplification | 0.7701 | 1 | SCN3A |
| OSU431895 | chr13:37467200-37469050 | Amplification | 0.9492 | 1 | PLEC |
| OSU431895 | chr22:48571700-48587350 | Amplification | 0.5304 | 2 | FARP1,STK24 |
| OSU431895 | chr16:16489650-16522550 | Amplification | 0.537 | 2 | ACTR3B,U6 |
| OSU431895 | chr7:6101100-6162800 | Amplification | 0.548 | 2 | FCAMR,C1orf116 |
| OSU431895 | chr10:26004900-26034450 | Amplification | 0.5519 | 2 | NPTXR,DNAL4 |
| OSU431895 | chr22:60977950-60981700 | Amplification | 0.5581 | 2 | TMEM255B,GAS6 |

FIG. 11H

| Patient ID | Region | Mutation type | Log2 ratio | Number of genes | Gene symbols |
|---|---|---|---|---|---|
| OSU431895 | chr9:26459350-26469900 | Amplification | 0.5604 | 2 | MYCBPAP,EPN3 |
| OSU431895 | chr34:18785700-18840750 | Amplification | 0.5732 | 2 | ETV5,DGKG |
| OSU431895 | chr7:43173400-43180600 | Amplification | 0.5938 | 2 | SLC39A1,CRTC2 |
| OSU431895 | chr10:38061150-38082800 | Amplification | 0.6231 | 2 | FHL2,C2orf49 |
| OSU431895 | chr4:62227650-62303450 | Amplification | 0.5052 | 3 | ITGA2,ENSCAFG00000018434,ITGA1 |
| OSU431895 | chr7:57557250-57585800 | Amplification | 0.5268 | 3 | ENSCAFG00000031963,U6,RNF125 |
| OSU431895 | chr8:43338250-43458900 | Amplification | 0.5862 | 3 | ENSCAFG00000016579,U6,KIAA0247 |
| OSU431895 | chr14:32475550-32498600 | Amplification | 0.8189 | 3 | LRIT1,ENSCAFG00000015927,RGR |
| OSU431895 | chr7:70491100-8257550 | Amplification | 0.5814 | 8 | PLXNA2,ENSCAFG00000026785,ENSCAFG00000010678,U6,ENSCAFG00000011883,cfa-mir-205,CAMK1G |
| OSU431895 | chr36:10329750-11130100 | Amplification | 0.6132 | 8 | SCN3A,SCN2A,U6,CSRNP3,GALNT3,U6,TTC21B,SCN1A |
| OSU431895 | chr26:35699700-38917000 | Deletion | -1.3683 | 29 | DRKT,PRKGT,CSTF2T,ENSCAFG00000023425,A1CF,ENSCAFG00000015602,U6,SGMS1,7SK,MINPP1,PAPSS2,ATAD1,ENSCAFG00000029370,ENSCAFG00000031699,PTEN,RNLS,ENSCAFG00000032091,LIPJ,LIPF,LIPK,LIPM,ANKRD22,ENSCAFG00000029090,ENSCAFG00000030844,STAMBPL1,ACTC,FAS,CH25H,LIPA |
| OSU431895 | chr36:111157950-15533500 | Amplification | 0.6229 | 37 | SCN1A,SCN9A,SCN7A,ENSCAFG00000011673,XIRP2,ENSCAFG00000011707,B3GALT1,STK39,CERS6,NOSTRIN,SPC25,G6PC2,ABCB11,DHRS9,ENSCAFG00000031746,LRP2,ENSCAFG00000012275,KLHL41,U6,FASTKD1,PPIG,CCDC173,PHOSPHO2,KLHL23,ENSCAFG00000029231,SSB,METTL5,UBR3,MYO3B,ENSCAFG00000012501,SP5,ERICH2,GAD1,ENSCAFG00000032252,U6,GORASP2,TLK1 |
| OSU431895 | chr4:623037000-68608100 | Amplification | 0.6557 | 43 | ITGA1,U6,ISL1,U6,PARP8,U6,EMB,HCN1,U6,ENSCAFG00000018512,MRPS30,FGF10,SNORA54,U6,NNT,SNORA33,PAIP1,ENSCAFG00000031903,C5orf34,5S_rRNA,C5orf28,CCL28,ENSCAFG00000018572,ENSCAFG00000030435,NIM1K,ZNF131,SEPP1,CCDC152,GHR,ENSCAFG00000023056,FBXO4,C5orf51,EEF1A1,OXCT1,PLCXD3,C6,MROH2B,C7,CARD6,SNORD72,PRKAA1 |
| OSU431895 | chr36:212319000-30677250 | Amplification | 0.6431 | 53 | AGPS,ENSCAFG00000013536,ENSCAFG00000013539,PDE11A,RBM45,U6,SNORD112,ENSCAFG00000028429,OSBPL6,DFNB59,PRKRA,FKBP7,PLEKHA3,TTN,ENSCAFG00000028776,CCDC141,SESTD1,ZNF385B,CWC22,U6,UBE2E3,ITGA4,CERKL,ENSCAFG00000014194,SSFA2,PPP1R1C,PDE1A,SNORD22,ENSCAFG00000030296,Y_RNA,DNAJC10,FRZB,NCKAP1,U6,DUSP19,TIGD1,NUP35,STK19,ZNF804A,U6,FSIP2,ZC3H15,ITGAV,FAM171B,ZSWM2,CALCRL,TFPI,7SK,GULP1,U6,COL3A1,COL5A2 |
| OSU431895 | chr36:155429500-21175300 | Amplification | 0.6498 | 55 | TLK1,ENSCAFG00000026775,U6,METTL8,DCAF17,CYBRD1,DYNC1I2,SLC25A12,HAT1,ENSCAFG00000012800,METAP1D,U6,DLX1,DLX2,SCARNA17,SCARNA18,ITGA6,ENSCAFG00000013060,RAPGEF4,ENSCAFG00000013140,ENSCAFG00000013158,7SK,SP3,OLA1,SP9,GPR155,SCRN3,U6,WIPF1,CHRNA1,ATF2,ENSCAFG00000001366,U6,ENSCAFG00000013374,U1,ENSCAFG00000030714,KIAA1715,ENSCAFG00000013399,EVX2,HOXD12,HOXD11,HOXD4,HOXD3,HOXD1,MTX2,TUG1_1,ENSCAFG00000030884,ENSCAFG00000032718,HNRNPA3,NFE2L2,AGPS |
| OSU431895 | chr36:698800-103072250 | Amplification | 0.6344 | 56 | GALNT13,HSPD1,5S_rRNA,KCNJ3,ENSCAFG00000009188,U6,ENSCAFG00000029956,NR4A2,GPD2,ENSCAFG00000009244,ENSCAFG00000009250,ENSCAFG00000009376,UGT2B31,UGT2A3,ENSCAFG00000024836,ENSCAFG00000002857,SULT1B1,ENSCAFG00000002673,ENSCAFG00000002875,SULT1E1,CSN1S1,CSN2,C4orf40,ODAM,CSN3,ENSCAFG00000028973,ENSCAFG00000002890,CABS1,ENSCAFG00000029608,AMTN,AMBN,ENAM,IGJ,UTP3,RUFY3,GRSF1,SNORA62,MOB1B,DCK,ENSCAFG00000002934,SLC4A4,GC,NPFFR2,ENSCAFG00000002856,ENSCAFG00000002859,COX18,ANKRD17,ALB,AFP,AFM,RASSF6,IL8,U6,ENSCAFG00000025016,PPBP,ENSCAFG00000003071,EREG,ENSCAFG00000003075 |
| OSU431895 | chr13:58449050-62934400 | Amplification | 0.7204 | 60 | 1,FAP,IFIH1,GCA,KCNH7,ENSCAFG00000031461,SLC38A11,SCN3A |
| | | | | | TMPRSS11A,ENSCAFG00000032430,TMPRSS11F,TMPRSS11E,U6,YTHDC1,ENSCAFG00000003036 |
| | | | | | 1464,MTHFD2L,ENSCAFG00000003069,EPGN,ENSCAFG00000003071,EREG,ENSCAFG00000003075 |

FIG. 11

| Patient ID | Region | Mutation type | Log2 ratio | Number of genes | Gene symbols |
|---|---|---|---|---|---|
| OSU431895 | chr13:92500-10016800 | Amplification | 0.726 | 76 | LAPTM4B,MATN2,ENSCAFG00000031952,SNORA72,C8orf47,ENSCAFG00000302250,POP1,NIPAL2,ENSCAFG00000018561,KCNS2,STK3,U6,OSR2,VPS13B,U6,cfa-mir-599,cfa-mir-875,RGS22,ENSCAFG00000000532,FBXO43,ENSCAFG00000031861,SPAG1,RNF19A,5S_rRNA,ANKRD46,SNX31,PABPC1,YWHAZ,Y_RNA,ZNF706,Y_RNA,GRHL2,ENSCAFG00000030800,NCALD,ENSCAFG00000025578,ENSCAFG00000000596,RRM2B,UBR5,ENSCAFG00000000632,ENSCAFG00000030010,SNRPD2,ODF1,KLF10,AZIN1,ENSCAFG00000000646,ATP6V1C1,BAALC,ENSCAFG00000000853,FZD6,CTHRC1,SLC25A32,DCAF13,RIMS2,ENSCAFG00000028565,ENSCAFG00000000683,ENSCAFG00000000872,DCSTAMP,DPYS,LRP12,ENSCAFG00000028333,ZFPM2,OXR1,SNORA62,ABRA,ENSCAFG00000000683,ENSCAFG00000000884,ENSCAFG00000000687,ANGPT1,U6,RSPO2,EIF3E,ENSCAFG00000028583,ENSCAFG00000000713,TMEM74,TRHR,NUDCD1,PKHD1L1 |
| OSU431895 | chr4:68648500-88273150 | Amplification | 0.6472 | 90 | TTC33,PTGER4,ENSCAFG00000001877,DAB2,C9,FYB,RICTOR,OSMR,ENSCAFG00000018652,LIFR,IL2,EGFLAM,ENSCAFG00000018671,U6,GDNF,WDR70,ENSCAFG00000018679,SNORA67,SNORD22,NUP155,U6,SNORA30,7SK,U6,C5orf42,NIPBL,GLAST,ENSCAFG00000029561,RANBP3L,ENSCAFG00000031830,SKP2,LMBRD2,ENSCAFG00000023144,ENSCAFG00000032039,CAPSL,IL7R,SPEF2,U6,PRLR,AGXT2,DNAJC21,BRIX1,RAD1,TTC23L,U6,RAI14,U6,ENSCAFG00000018825,AMACR,SLC45A2,RXFP3,ADAMTS12,TARS,NPR3,5S_rRNA,ENSCAFG00000018879,ENSCAFG00000018881,ZFR,ENSCAFG00000027374,MTMR12,GOLPH3,PDZD2,C5orf22,ENSCAFG00000003186,ENSCAFG00000018939,CDH6,ENSCAFG00000018956,U6,CDH9,ENSCAFG00000018980,7SK,CDH10,ENSCAFG00000017424,ENSCAFG00000019017,ENSCAFG00000019023,CDH12,ENSCAFG00000031957,CDH18,SNORA62,U2,7SK,RNF167,BASP1,FAM134B,MYO10,ZNF622,MARCH11,FBXL7,ENSCAFG00000019108,ANKH |
| OSU431895 | chr3:32584700-47752750 | Amplification | 0.6863 | 133 | CCSER2,U6,GRID1,ENSCAFG00000031941,cfa-mir-346,WAPAL,CPN4,LDB3,BMPR1A,MMRN2,ENSCAFG00000024229,SNCG,ENSCAFG00000016093,ENSCAFG00000016095,ENSCAFG00000032460,FAM35A,SYT15,GPRIN2,NPY4R,ENSCAFG00000016149,ANTXRL,ZNF488,RBP3,GDF2,GDF10,ENSCAFG00000023521,DCP2,U6,MCC,FAM193B,GRK6,DDX41,DOK3,ENSCAFG00000016333,DBN1,PRR7,F12,PFN3,SLC34A1,RGS14,LMAN2,MXD3,PRELID1,RAB24,NSD1,FGFR4,ZNF346,NSD1,FGFR4,ENSCAFG00000016545,ENSCAFG00000026478,UIMC1,7SK,U4,HK3,UNC5A,TSPAN17,EIF4E1B,SNCB,GPRIN1,CDHR2,RNF44,FAF2,CLTB,NOP16,ARL10,cfa-mir-1271,U6,KIAA1191,SIMC1,SUB1,THOC3,CPLX2,HRH2,U6,7SK,SFXN1,DRD1,MSX2,ENSCAFG00000030421,C5orf47,CPEB4,U6,ENSCAFG00000016775,BOD1,STC2,NKX2.5,ENSCAFG00000016785,BNIP1,CREBRF,ATP6V0E1,ERGIC1,DUSP1,NEURL1B,SH3PXD2B,U6,SNORD22,UBTD2,U6,EFCAB9,STK10,5S_rRNA,FBXW11,SMIM23,FGF18,NPM1,U6,TLX3,RANBP17,U6,GABRP,KCNIP1,KCNMB1,LCP2,FOXI1,DOCK2,FAM196B,SPDL1,ENSCAFG00000017000,U6,SLIT3,cfa-mir-218-2,PANK3,RARS,WWC1,U6,TENM2,ENSCAFG00000017171,ENSCAFG00000017180,snoZ25,U6,U6,MAT2B,HMMR |
| OSU431895 | chr4:47781300-62225000 | Amplification | 0.6927 | 142 | HMMR,NUDCD2,CCNG1,ENSCAFG00000017212,5S_rRNA,U6,GABRG2,ENSCAFG00000017236,GABRA1,ENSCAFG00000017239,GABRA6,GABRB2,ATP10B,cfa-mir-148a,ENSCAFG00000017264,SLU7,C5orf54,U6,C1QTNF2,ENSCAFG00000017274,FABP6,ENSCAFG00000017689,U4,PWWP2A,TTC1,ADRA1B,ENSCAFG00000029942,IL12B,UBLCP1,RNF145,EBF1,U6,CLINT1,U6,THG1L,SOX30,ADAM19,NIPAL4,CYFIP2,FNDC9,U6,ITK,FAM71B,MED7,HAVCR1,TIMD4,SGCD,ENSCAFG00000030235,MRPL22,ENSCAFG00000032419,MFAP3,FAM114A2,GRIA1,NMUR2,GLRA1,G3BP1,ATOX1,ENSCAFG00000030561,SPARC,FAT2,SLC36A1,SLC36A2,SLC36A3,GM2A,ENSCAFG00000026927,CCDC69,U6,ANXA6,TNIP1,GPX3,ENSCAFG00000017861,ENSCAFG00000023257,ZNF300,U6,SMIM3,7SK,DCTN4,RBM22,MYOZ3,SYNPO,NDST1,RPS14,CD74,TCOF1,ARSI,CAMK2A,SLC6A7,CDX1,PDGFRB,CSF1R,HMGXB3,ENSCAFG00000032400,TIGD6,SLC26A2,PDE6A,PPARGC1B,cfa-mir-378,U6,ARHGEF37,ENSCAFG00000018286,cfa-mir-145,cfa-mir-143,IL17B,PCYOX1L,GRPEL2,AFAP1L1,ABLIM3,U6,SH3TC2,ADRB2,HTR4,FBXO38,SPINK9,SPINK7,GZMK,ESM1,ENSCAFG00000008488,ENSCAFG00000018385,ENSCAFG00000031454,SNX16,HSPB3,ENSCAFG00000002726,ITAF,ARL15,FST,ENSCAFG00000018410,ENSCAFG00000026642,ENSCAFG00000018414,ENSCAFG00000031509,MOCS2,ITGA2 |

FIG. 11J

| Patient ID | Region | Mutation type | Log2 ratio | Number of genes | Gene symbols |
|---|---|---|---|---|---|
| OSU431895 | chr13:37469800-58435050 | Amplification | 0.7574 | 173 | PLEC,ENSCAFG00000030933,ENSCAFG00000030148,GRINA,SPATC1,ENSCAFG00000032288,OPLAH,EXOSC4, GPAA1,SHARPIN,CYC1,ENSCAFG00000029569,ENSCAFG00000001540,ENSCAFG00000032656,ENSCAFG00000 001541,ENSCAFG00000001542,MROH1,ENSCAFG00000025328,VPS28,ENSCAFG00000001554,ENSCAFG00000 001559,HSF1,DGAT1,TMEM249,ENSCAFG00000001588,FBXL6,ADCK5,CPSF1,SLC39A4,TONSL,CYHR1,KIFC2,F OXH1,PPP1R16A,GPT,MFSD3,RECQL4,LRRC24,LRRC14,C8orf82,ARHGAP39,COMMD5,ZNF7,ZNF517,RPL8,ZNF 34,ZNF250,ENSCAFG00000001685,ZNF252,C8orf33,ENSCAFG00000030006,CHRNB4,CHRNA3,CHRNA5,HYKK,IR EB2,WFS1,LIMCH1,PHOX2B,TMEM33,SLC30A9,BEND4,U6,SHISA3,ATP6A1,U4,GRXCR1,ENSCAFG00000024933, KCTD8,ENSCAFG00000001830,YIPF7,GUF1,GNPDA2,U6,U6,U2,GABRG1,GABRA2,GABRA4,GABRB1,COMMD8,A TP10D,CORIN,NFXL1,CNGA1,ENSCAFG00000029469,NIPAL1,TXK,ENSCAFG00000028493,TEC,ENSCAFG00000 026538,SLAIN2,SLC10A4,ZAR1,FRYL,U6,OCIAD1,OCIAD2,CWH43,DCUN1D4,LRRC66,SGCB,SPATA18,U4,USP46 ,SNORA26,SNORA26,RASL11B,SCFD2,5S_rRNA,FIP1L1,LNX1,CHIC2,GSX2,PDGFRA,KIT,ENSCAFG00000002088 ,U6,KDR,SRD5A3,TMEM165,CLOCK,PDCL2,NMU,ENSCAFG00000031519,EXOC1,CEP135,ENSCAFG00000002220 0,U2,KIAA1211,AASDH,PPAT,ENSCAFG00000002228,PAICS,SRP72,ARL9,THEGL,HOPX,SPINK2,U5,REST,NOA1, POLR2B,IGFBP7,ENSCAFG00000002332,U6,ENSCAFG00000002333,ENSCAFG00000002335,ENSCAFG00000002 336,ENSCAFG00000002337,U6,SNORA62,U6,ENSCAFG00000032523,LPHN3,U6,5S_rRNA,ENSCAFG00003007 0,TECRL,ENSCAFG00000032555,ENSCAFG00000002388,EPHA5,U6,U6,U6,CENPC,STAP1,UBA6,GNRHR,ENSCA FG00000025497,ENSCAFG00000025398,TMPRSS11D,TMPRSS11A |
| OSU431895 | chr13:100023450-374670000 | Amplification | 0.7649 | 182 | PKHD1L1,EBAG9,SYBU,SNORD112,ENSCAFG00000020173,KCNV1,U6,ENSCAFG00000020173,ENSCAFG0000000 00747,ENSCAFG00000000749,ENSCAFG00000028980,CSMD3,ENSCAFG00000028131,U6,ENSCAFG00000000256 0,MGST3,ENSCAFG00000030964,U6,ENSCAFG00000000805,U6,TRPS1,ENSCAFG00000028713,ENSCAFG0000000 027644,EIF3H,UTP23,RAD21,ENSCAFG00000029199,AARD,SLC30A8,MED30,EXT1,SAMD12,U6,TNFRSF11B,EN SCAFG00000000835,COLEC10,MAL2,NOV,ENPP2,TAF2,DSCC1,ENSCAFG00000000883,DEPTOR,COL14A1,MRP L13,MTBP,SNTB1,ENSCAFG00000000961,5S_rRNA,HAS2,U6,U6,U1,U6,ZHX2,DERL1,TBC1D31,ENSCAFG0000000 31914,FAM83A,ENSCAFG00000001000,ZHX1,ATAD2,WDYHV1,FBXO32,ENSCAFG00000001011,KLHL36,ANXA13, FAM91A1,FER1L6,ENSCAFG00000008774,TMEM65,TRMT12,RNF139,TATDN1,NDUFB9,MTSS1,ZNF572,SQLE,KI AAO196,TRIB1,ENSCAFG00000001338,ENSCAFG00000030361,ENSCAFG00000001080,U6,U4,7SK,FAM84B, U6,MYC,5S_rRNA,GSDMC,FAM49B,SNORA73,ASAP1,ENSCAFG00000031137,ADCY8,U6,LDHB,7SK,EFR3A,U4,E NSCAFG00000011G2,HHLA1,KCNQ3,LRRC6,7SK,TMEM71,PHF20L1,TG,SLA,WISP1,NDRG1,ST3GAL1,ENSCAF G00000029450,ZFAT,SNORA48,cfa-mir-30b,cfa-mir- 30d,ENSCAFG00000031399,KHDRBS3,U6,SNORA32,SNORD74,ENSCAFG00000001168,5S_rRNA,ENSCAFG0000 0029044,U6,U6,FAM135B,COL22A1,KCNK9,TRAPPC9,CHRAC1,AGO2,PTK2,cfa-mir- 151,DENND3,SLC45A4,ENSCAFG00000029505,GPR20,PTP4A3,ENSCAFG00000001250,ENSCAFG00000028787, ENSCAFG00000031926,TSNARE1,BAI1,ENSCAFG00000001272,PSCA,THEM6,SLURP1,LYPD2,LYNX1,ENSCAFG 00000001265,ENSCAFG00000031437,LY6E,ENSCAFG00000031517,LY6H,GPIHBP1,ENSCAFG00000032427,ENS CAFG00000029869,GLI4,ENSCAFG00000032607,ZNF696,RHPN1,MAFA,ZC3H3,GSDMD,NAPRT1,EEF1D,TIGD5,P YCRL,TSTA3,ZNF623,ENSCAFG00000031942,MAPK15,FAM83H,SCRIB,PUF60,NRBP2,PLEC,ENSCAFG00000029 172 |

FIG. 11K

| Patient ID | Region | Mutation type | Log2 ratio | Number of genes | Gene symbols |
|---|---|---|---|---|---|
| OSU431895 | chr4:69700-324721501 | Amplification | 0.6663 | 278 | IFIT2,IFIT3,U4,IFIT1,IFIT5,ZNF248,ZNF25,ENSCAFG00000028519,ENSCAFG00000029103,ENSCAFG00000024143,U6,ZNF37A,CHRM3,ENSCAFG00000009885,ENSCAFG00000009991,ENSCAFG00000008988,ZP4,RYR2,7SK,ENSCAFG00000008063,SNORA25,U6,SNORA2,ENSCAFG00000010041,MTR,U6,ACTN2,HEATR1,LGALS8,EDARADD,ERO1LB,GPR137B,ENSCAFG00000030994,NID1,LYST,ENSCAFG00000031911,GNG4,B3GALNT2,TBCE,GGPS1,ARID4B,RBM34,TOMM20,SNORA14,U6,ENSCAFG00000032166,IRF2BP2,TARBP1,COA6,SLC35F3,7SK,KCNK1,ENSCAFG00000011566,PCNXL2,NTPCR,5S_rRNA,ENSCAFG00000011616,SIPA1L2,DISC1,SNORA25,ENSCAFG00000030982,EGLN1,SNORD35,SPRTN,EXOC8,GNPAT,C1orf131,TRIM67,FAM89A,ARV1,TTC13,CAPN9,C1orf198,AGT,cfa-mir-1841,cfa-mir-1841,U6,PGBD5,GALNT2,ENSCAFG00000024420,URB2,TAF5L,ABCB10,NUP133,ACTA1,CCSAP,RAB4A,U6,RHOU,ENSCAFG00000012252,U6,5S_rRNA,5S_rRNA,UBE2D1,TFAM,BICC1,5S_rRNA,ENSCAFG00000002792,1,ENSCAFG00000032217,ENSCAFG00000012382,PHYHIPL,FAM13C,SLC16A9,CCDC6,U6,ENSCAFG00000001245,8,ANK3,U6,CDK1,RHOBTB1,U2,GAPDH,ENSCAFG00000012971,TMEM26,5S_rRNA,C10orf107,ARID5B,RTKN2,ZNF365,ADO,EGR2,NRBF2,JMJD1C,ENSCAFG00000026634,7SK,REEP3,CTNNA3,ENSCAFG00000013264,LRRTM3,ENSCAFG00000024412,ENSCAFG00000013277,ENSCAFG00000006036,DNAJC12,ENSCAFG00000028988,HNRNPA1L2,SIRT1,ENSCAFG00000013319,HERC4,U6,5S_rRNA,MYPN,ATOH7,P8LD,HNRNPH3,RUFY2,DNA2,SLC25A16,SCARNA18,SCARNA17,TET1,U6,5S_rRNA,CCAR1,U6,STOX1,DDX50,DDX21,KIAA1279,U4,SRGN,VPS26A,SUPV3L1,HKDC1,HK1,TACR2,TSPAN15,NEUROG3,C10orf35,COL13A1,5S_rRNA,H2AFY2,AIFM2,TYSND1,PPA1,ENSCAFG00000014038,LRRC20,EIF4EBP2,NODAL,PALD1,PRF1,ENSCAFG00000014078,ADAMTS14,TBATA,SGPL1,PCBD1,UNC5B,SLC29A3,ENSCAFG00000014229,U2,C10orf54,PSAP,U6,CHST3,SPOCK2,ASCC1,ANAPC16,DDIT4,DNAJB12,MICU1,U6,ENSCAFG00000014500,MCU,OIT3,PLA2G12B,U6,ENSCAFG00000014550,P4HA1,NUDT13,ECD,FAM149B1,DNAJC9,ENSCAFG00000031286,TTC18,ANXA7,U6,MSS51,PPP3CB,USP54,MYOZ1,SYNPO2L,SEC24C,FUT11,CHCHD1,ZSWIM8,ENSCAFG00000015050,CAMK2G,PLAU,ENSCAFG00000031053,VCL,AP3M1,ADK,U6,SNORD2,snoU2-30,U6,KAT6B,ENSCAFG00000022859,ENSCAFG00000031398,SAMD8,VDAC2,COMTD1,ZNF503,C10orf11,U6,ENSCAFG00000030490,KCNMA1,U6,DLG5,POLR3A,RPS24,U6,U6,ENSCAFG00000030222,ZMIZ1,PPIF,ZCCHC24,ANXA11,TMEM254,7SK,ENSCAFG00000023232,SFTPD,ENSCAFG00000015754,MAT1A,DYDC1,DYDC2,FAM213A,TSPAN14,SH2D4B,5S_rRNA,DNAJB6,NRG3,ENSCAFG00000015896,7SK,GHITM,CDHR1,LRIT2 |

FIG. 11L

Supplementary Table 6. Somatic coding structural variants identified by exome sequencing of primary canine lung cancers.

| Patient ID | Genomic coordinates region 1 | Genomic coordinates region 2 | Rearrangement type | Gene(s) affected |
|---|---|---|---|---|
| CCB010387 | chr23:44360546 | chr17:63950184 | Translocation | WWTR1-ATP5F1 |
| CCB050354 | chrX:103308454 | chr15:59537883 | Translocation | MBNL3- |
| OSU431895 | chr9:12124378 | chr9:12531743 | Inversion | TEX2-PECAM1 |

FIG. 12

Supplementary Table 7. Canine genomic regions covered by custom amplicon panel.

| Gene symbol | Chromosomal region |
|---|---|
| ABL1 | chr9:53132787-53132980 |
| ABL1 | chr9:53131795-53131993 |
| ABL1 | chr9:53131719-53131931 |
| ABL1 | chr9:53129710-53129941 |
| ABL1 | chr9:53141626-53141773 |
| ABL1 | chr9:53141666-53141807 |
| AKT1 | chr8:72322531-72322699 |
| AKT1 | chr8:72326350-72326560 |
| ALK | chr17:23025511-23025720 |
| ALK | chr17:23035562-23035750 |
| APC | chr3:258857-259033 |
| APC | chr3:258218-258432 |
| APC | chr3:257603-257802 |
| APC | chr3:257493-257662 |
| APC | chr3:257377-257575 |
| APC | chr3:257323-257484 |
| APC | chr3:257192-257389 |
| APC | chr3:257095-257294 |
| APC | chr3:257006-257177 |
| APC | chr3:256898-257090 |
| APC | chr3:256847-257042 |
| ATM | chr5:24271300-24271494 |
| ATM | chr5:24267485-24267645 |
| ATM | chr5:24227983-24228182 |
| ATM | chr5:24226702-24226901 |
| ATM | chr5:24225744-24225929 |
| ATM | chr5:24219490-24219708 |
| ATM | chr5:24272535-24272754 |
| ATM | chr5:24205249-24205465 |
| ATM | chr5:24205240-24205437 |
| ATM | chr5:24201430-24201627 |
| ATM | chr5:24199499-24199678 |
| ATM | chr5:24198654-24198849 |
| ATM | chr5:24191423-24191602 |
| ATM | chr5:24187574-24187742 |
| ATM | chr5:24182536-24182771 |
| ATM | chr5:24182478-24182675 |
| ATM | chr5:24262108-24262315 |
| ATM | chr5:24248285-24248459 |
| BRAF | chr16:8296161-8296342 |

FIG. 13A

| Gene symbol | Chromosomal region |
|---|---|
| BRAF | chr16:8274236-8274435 |
| BCL2 | chr1:13734560-13734773 |
| BCL6 | chr34:20115524-20115716 |
| PTPRJ | chr18:41635247-41635349 |
| PTPRJ | chr18:41610376-41610575 |
| PTPRJ | chr18:41608739-41608930 |
| PTPRJ | chr18:41608842-41609026 |
| PTPRJ | chr18:41608498-41608684 |
| PTPRJ | chr18:41607194-41607362 |
| PTPRJ | chr18:41605254-41605452 |
| PTPRJ | chr18:41604588-41604785 |
| PTPRJ | chr18:41602799-41602982 |
| PTPRJ | chr18:41599896-41600094 |
| PTPRJ | chr18:41599639-41599857 |
| PTPRJ | chr18:41596160-41596359 |
| PTPRJ | chr18:41592490-41592700 |
| PTPRJ | chr18:41591115-41591314 |
| PTPRJ | chr18:41587706-41587924 |
| PTPRJ | chr18:41632742-41632920 |
| PTPRJ | chr18:41632835-41633029 |
| PTPRJ | chr18:41629887-41630079 |
| PTPRJ | chr18:41630032-41630209 |
| PTPRJ | chr18:41628351-41628541 |
| PTPRJ | chr18:41628459-41628646 |
| PTPRJ | chr18:41624925-41625123 |
| PTPRJ | chr18:41625081-41625280 |
| PTPRJ | chr18:41622247-41622435 |
| PTPRJ | chr18:41622397-41622596 |
| PTPRJ | chr18:41617533-41617716 |
| PTPRJ | chr18:41617662-41617861 |
| PTPRJ | chr18:41616514-41616733 |
| PTPRJ | chr18:41616636-41616885 |
| PTPRJ | chr18:41614210-41614408 |
| PTPRJ | chr18:41614356-41614555 |
| CDH1 | chr5:80784506-80784734 |
| CDH1 | chr5:80776432-80776601 |
| CDH1 | chr5:80774217-80774415 |
| CDKN2A | chr11:41225734-41225940 |
| CDKN2A | chr11:41225847-41226091 |
| CDKN2A | chr11:41225923-41226135 |
| CSF1R | chr4:59009763-59009961 |

FIG. 13B

| Gene symbol | Chromosomal region |
|---|---|
| CSF1R | chr4:58991781-58991961 |
| CTNNB1 | chr23:10560210-10560409 |
| DDR2 | chr38:20031670-20031800 |
| DDR2 | chr38:20018886-20019053 |
| DDR2 | chr38:20011852-20012021 |
| DDR2 | chr38:20015205-20015318 |
| DDR2 | chr38:20037000-20037174 |
| EGFR | chr18:5984689-5984867 |
| EGFR | chr18:6009937-6010119 |
| EGFR | chr18:6015506-6015703 |
| EGFR | chr18:6016237-6016419 |
| EGFR | chr18:6022048-6022235 |
| EGFR | chr18:6022102-6022321 |
| EGFR | chr18:6031188-6031372 |
| EGFR | chr18:6015468-6015615 |
| EGFR | chr18:6032170-6032301 |
| EGFR | chr18:6036127-6036259 |
| ERBB2 | chr9:22764275-22764455 |
| ERBB2 | chr9:22763963-22764154 |
| ERBB2 | chr9:22763598-22763819 |
| ERBB2 | chr9:22773787-22773946 |
| ERBB2 | chr9:22763320-22763513 |
| ERBB2 | chr9:22765031-22765155 |
| ERBB4 | chr37:19076188-19076407 |
| ERBB4 | chr37:19283169-19283364 |
| ERBB4 | chr37:19323504-19323674 |
| ERBB4 | chr37:19325350-19325532 |
| ERBB4 | chr37:19329168-19329367 |
| ERBB4 | chr37:19332359-19332524 |
| ERBB4 | chr37:19397751-19397948 |
| ERBB4 | chr37:19542733-19542967 |
| ERBB4 | chr37:19313045-19313157 |
| ERBB4 | chr37:19289223-19289313 |
| ERBB4 | chr37:19289294-19289464 |
| EZH2 | chr16:1987314-1987557 |
| FBXW7 | chr15:50190724-50190883 |
| FBXW7 | chr15:50192437-50192618 |
| FBXW7 | chr15:50194544-50194703 |
| FBXW7 | chr15:50194506-50194656 |
| FBXW7 | chr15:50195961-50196180 |
| FBXW7 | chr15:50204776-50204983 |

FIG. 13C

| Gene symbol | Chromosomal region |
|---|---|
| FGFR1 | chr16:27068305-27068524 |
| FGFR1 | chr16:27064078-27064262 |
| FGFR2 | chr28:31322761-31322958 |
| FGFR2 | chr28:31338175-31338374 |
| FGFR2 | chr28:31342907-31343177 |
| FGFR2 | chr28:31343056-31343224 |
| FGFR2 | chr28:31313535-31313691 |
| FGFR2 | chr28:31341774-31341866 |
| FGFR3 | chr3:62316073-62316318 |
| FGFR3 | chr3:62313411-62313598 |
| FGFR3 | chr3:62311495-62311744 |
| FGFR3 | chr3:62311181-62311389 |
| FGFR3 | chr3:62310633-62310841 |
| FLT3 | chr25:11658010-11658206 |
| FLT3 | chr25:11650244-11650417 |
| FLT3 | chr25:11645983-11646179 |
| FLT3 | chr25:11644347-11644540 |
| FLT3 | chr25:11651048-11651257 |
| FLT3 | chr25:11650091-11650285 |
| FRK | chr12:71663010-71663169 |
| GNAQ | chr1:80927708-80927894 |
| GNAQ | chr1:80927595-80927788 |
| GNAQ | chr1:80914802-80914992 |
| GNAQ | chr1:80914684-80914869 |
| GNAQ | chr1:80853899-80854117 |
| GNAQ | chr1:80853784-80853992 |
| GNAQ | chr1:80851113-80851319 |
| GNAQ | chr1:80851055-80851212 |
| GNAS | chr24:43656666-43656897 |
| GNAS | chr24:43656737-43656956 |
| HNF1A | chr26:16818019-16818204 |
| HNF1A | chr26:16818585-16818780 |
| HRAS | chr18:25644183-25644366 |
| HRAS | chr18:25644512-25644711 |
| IDH1 | chr37:16524257-16524455 |
| IDH2 | chr3:53075018-53075197 |
| ITK | chr4:52913310-52913489 |
| JAK2 | chr1:93416438-93416687 |
| JAK3 | chr20:45061934-45062125 |
| JAK4 | chr20:45060022-45060184 |
| JAK5 | chr20:45054387-45054604 |

FIG. 13D

| Gene symbol | Chromosomal region |
|---|---|
| KDR | chr13:47442807-47443005 |
| KDR | chr13:47442922-47443121 |
| KDR | chr13:47450231-47450424 |
| KDR | chr13:47451501-47451693 |
| KDR | chr13:47456971-47457187 |
| KDR | chr13:47458307-47458469 |
| KDR | chr13:47468134-47468322 |
| KDR | chr13:47472965-47473163 |
| KDR | chr13:47473656-47473869 |
| KIT | chr13:47144443-47144632 |
| KIT | chr13:47178311-47178450 |
| KIT | chr13:47178426-47178639 |
| KIT | chr13:47178530-47178716 |
| KIT | chr13:47176964-47177163 |
| KIT | chr13:47179068-47179254 |
| KIT | chr13:47180332-47180521 |
| KIT | chr13:47182346-47182529 |
| KIT | chr13:47184222-47184406 |
| KIT | chr13:47187866-47188075 |
| KIT | chr13:47187759-47187888 |
| KRAS | chr27:22279727-22279909 |
| KRAS | chr27:22277814-22278013 |
| KRAS | chr27:22261748-22261919 |
| MET | chr14:55626818-55627017 |
| MET | chr14:55627435-55627650 |
| MET | chr14:55677379-55677569 |
| MET | chr14:55685409-55685605 |
| MET | chr14:55691158-55691383 |
| MET | chr14:55699134-55699333 |
| MLH1 | chr23:6914204-6914398 |
| MTOR | chr2:84924877-84924999 |
| MTOR | chr2:84932668-84932872 |
| MTOR | chr2:84927931-84928072 |
| MTOR | chr2:84935761-84935930 |
| MTOR | chr2:84927484-84927631 |
| NOTCH1 | chr9:49016900-49017088 |
| NOTCH1 | chr9:49010843-49011051 |
| NOTCH1 | chr9:49010128-49010283 |
| NPM1 | chr4:40756680-40756873 |
| NRAS | chr17:52413400-52413574 |
| NRAS | chr17:52415785-52415961 |

FIG. 13E

| Gene symbol | Chromosomal region |
| --- | --- |
| NRAS | chr17:52418025-52418207 |
| PDGFRA | chr13:46755130-46755319 |
| PDGFRA | chr13:46758112-46758261 |
| PDGFRA | chr13:46758431-46758605 |
| PDGFRA | chr13:46762522-46762720 |
| PIK3CA | chr34:12647939-12648113 |
| PIK3CA | chr34:12648039-12648254 |
| PIK3CA | chr34:12651012-12651167 |
| PIK3CA | chr34:12659946-12660166 |
| PIK3CA | chr34:12660627-12660824 |
| PIK3CA | chr34:12660735-12660974 |
| PIK3CA | chr34:12662924-12663096 |
| PIK3CA | chr34:12666251-12666443 |
| PIK3CA | chr34:12674167-12674366 |
| PIK3CA | chr34:12675544-12675768 |
| PIK3CA | chr34:12675591-12675825 |
| PTEN | chr26:37878229-37878397 |
| PTEN | chr26:37885976-37886175 |
| PTEN | chr26:37900453-37900622 |
| PTEN | chr26:37906248-37906447 |
| PTEN | chr26:37906397-37906589 |
| PTEN | chr26:37906499-37906671 |
| PTEN | chr26:37909934-37910153 |
| PTEN | chr26:37909981-37910174 |
| PTEN | chr26:37910002-37910174 |
| PTPN11 | chr26:10014538-10014695 |
| PTPN11 | chr26:10052693-10052873 |
| RB1 | chr22:3173653-3173838 |
| RB1 | chr22:3163154-3163332 |
| RB1 | chr22:3150317-3150489 |
| RB1 | chr22:3139920-3140083 |
| RB1 | chr22:3086935-3087134 |
| RB1 | chr22:3074403-3074621 |
| RB1 | chr22:3073714-3073938 |
| RB1 | chr22:3151283-3151502 |
| RB1 | chr22:3141437-3141649 |
| RB1 | chr22:3080014-3080184 |
| RET | chr28:3963179-3963336 |
| RET | chr28:3962219-3962405 |
| RET | chr28:3957290-3957458 |
| RET | chr28:3955803-3956014 |

FIG. 13F

| Gene symbol | Chromosomal region |
| --- | --- |
| RET | chr28:3953762-3953961 |
| SMAD4 | chr1:23912698-23912906 |
| SMAD4 | chr1:23912117-23912330 |
| SMAD4 | chr1:23907338-23907536 |
| SMAD4 | chr1:23903927-23904114 |
| SMAD4 | chr1:23902156-23902353 |
| SMAD4 | chr1:23894364-23894550 |
| SMAD4 | chr1:23893105-23893301 |
| SMAD4 | chr1:23884149-23884355 |
| SMAD4 | chr1:23882497-23882684 |
| SMARCB1 | chr26:28724265-28724461 |
| SMARCB1 | chr26:28718341-28718526 |
| SMARCB1 | chr26:28716112-28716322 |
| SMARCB1 | chr26:28692815-28693023 |
| SMO | chr14:7525791-7525990 |
| SMO | chr14:7524837-7525024 |
| SMO | chr14:7524444-7524653 |
| SMO | chr14:7521708-7521886 |
| SMO | chr14:7520567-7520757 |
| SRC | chr24:26017664-26017849 |
| STK11 | chr20:57578759-57578958 |
| STK11 | chr20:57566739-57566975 |
| STK11 | chr20:57566801-57567028 |
| STK11 | chr20:57565779-57565960 |
| STK11 | chr20:57563316-57563508 |
| TP53 | chr5:32562056-32562255 |
| TP53 | chr5:32562928-32563119 |
| TP53 | chr5:32563278-32563472 |
| TP53 | chr5:32563619-32563858 |
| TP53 | chr5:32563769-32563968 |
| TP53 | chr5:32563888-32564137 |
| TP53 | chr5:32564559-32564757 |
| TP53 | chr5:32565057-32565252 |
| VHL | chr20:8210831-8211067 |
| VHL | chr20:8209613-8209812 |
| VHL | chr20:8206929-8207144 |

FIG. 13G

Supplementary Table 9. Somatic coding SNVs identified by panel sequencing of primary canine lung cancers.

| Patient ID | Tumor Type | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|---|
| BACA | cPAC | CDKN2A | ENSCAFT00000002623.3 | chr11:41225906C>T | | c.148G>A | p.Gly50Arg | Missense variant | 92.5% |
| CCB010120 | cPAC | ERBB2 | ENSCAFT00000025936.3 | chr9:22765127A>T | | c.1976T>A | p.Val659Glu | Missense variant | 33.8% |
| CCB010387 | cPAC | ERBB2 | ENSCAFT00000025936.3 | chr9:22765127A>T | | c.1976T>A | p.Val659Glu | Missense variant | 46.7% |
| CCB010387 | cPAC | KDR | ENSCAFT00000003500.3 | chr13:47440084C>T | | c.3846-1G>A | | Splice acceptor variant | 43.2% |
| CCB020051 | cPAC | ATM | ENSCAFT00000023032.4 | chr5:24205342T>C | | c.7414A>G | p.Lys2472Glu | Missense variant | 34.1% |
| CCB020051 | cPAC | ERBB2 | ENSCAFT00000025936.3 | chr9:22765127A>T | | c.1976T>A | p.Val659Glu | Missense variant | 44.0% |
| CCB020198 | cPAC | ERBB2 | ENSCAFT00000025936.3 | chr9:22765127A>T | | c.1976T>A | p.Val659Glu | Missense variant | 34.1% |
| CCB020198 | cPAC | PTEN | ENSCAFT00000024821.3 | chr26:37906437G>T | | c.688G>T | p.Asp230Tyr | Missense variant | 27.9% |
| CCB020245 | cPAC | HNF1A | ENSCAFT00000016677.2 | chr26:16818740C>T | | c.814C>T | p.Arg272Cys | Missense variant | 22.4% |
| CCB020251 | cPAC | PTEN | ENSCAFT00000024821.3 | chr26:37906431T>C | | c.682T>C | p.Cys228Arg | Missense variant | 21.2% |
| CCB020251 | cPAC | SMAD4 | ENSCAFT00000000266.3 | chr1:238944191T>C | | c.1052A>G | p.Asp351Gly | Missense variant | 12.5% |
| CCB040005 | cPAC | AKT1 | ENSCAFT00000029177.3 | chr8:723263731T>C | | c.157A>G | p.Asn53Asp | Missense variant | 24.6% |
| CCB040005 | cPAC | ERBB2 | ENSCAFT00000025936.3 | chr9:22765127A>T | | c.1976T>A | p.Val659Glu | Missense variant | 34.8% |
| CCB040068 | cPAC | ERBB2 | ENSCAFT00000025936.3 | chr9:22765127A>T | | c.1976T>A | p.Val659Glu | Missense variant | 34.0% |
| CCB040149 | cPAC | ERBB2 | ENSCAFT00000025936.3 | chr9:22765127A>T | | c.1976T>A | p.Val659Glu | Missense variant | 22.3% |
| CCB040149 | cPAC | TP53 | ENSCAFT00000026465.3 | chr5:32564629C>T | | c.260G>A | p.Gly94Ser | Missense variant | 39.6% |
| CCB040231 | cPAC | ERBB2 | ENSCAFT00000025936.3 | chr9:22765127A>T | | c.1976T>A | p.Val659Glu | Missense variant | 20.3% |
| CCB050243 | cPAC | KRAS | ENSCAFT00000010525.3 | chr27:22261798G>T | | c.35G>T | p.Gly12Val | Missense variant | 29.8% |
| CCB050243 | cPAC | ERBB2 | ENSCAFT00000025936.3 | chr9:22765077T>C | | c.2026A>G | p.Lys676Glu | Missense variant | 36.9% |
| CCB050260 | cPAC | TP53 | ENSCAFT00000026465.3 | chr5:32563074G>A | | c.769C>T | p.Arg257Cys | Missense variant | 11.3% |
| CCB050342 | cPAC | ERBB2 | ENSCAFT00000025936.3 | chr9:22765127A>T | | c.1976T>A | p.Val659Glu | Missense variant | 10.0% |
| CCB050345 | cPAC | TP53 | ENSCAFT00000026465.3 | chr5:32564027G>A | | c.380C>T | p.Ala127Val | Missense variant | 12.3% |
| CCB050350 | cPAC | ERBB2 | ENSCAFT00000025936.3 | chr9:22765127A>T | | c.1976T>A | p.Val659Glu | Missense variant | 30.5% |
| CCB050354 | cPAC | KRAS | ENSCAFT00000010525.3 | chr27:22261798G>T | | c.35G>T | p.Gly12Val | Missense variant | 29.8% |
| CCB050356 | cPAC | ERBB2 | ENSCAFT00000025936.3 | chr9:22765077T>C | | c.2026A>G | p.Lys676Glu | Missense variant | 36.9% |
| CCB050362 | cPAC | TP53 | ENSCAFT00000026465.3 | chr5:32563074G>A | | c.769C>T | p.Arg257Cys | Missense variant | 48.8% |
| CCB050362 | cPAC | ERBB2 | ENSCAFT00000025936.3 | chr9:22765127A>T | | c.1976T>A | p.Val659Glu | Missense variant | 10.6% |
| CCB050363 | cPAC | APC | ENSCAFT00000011749.3 | chr3:256988T>A | | c.2915A>T | p.Glu972Val | Missense variant | 33.4% |
| CCB050363 | cPAC | FGFR1 | ENSCAFT00000009709.3 | chr16:27068444G>A | | c.749G>A | p.Arg250Gln | Missense variant | 24.7% |
| CCB050363 | cPAC | FGFR2 | ENSCAFT00000009748.4 | chr28:31343109T>C | | c.862A>G | p.Thr288Ala | Missense variant | 25.8% |
| CCB060040 | cPAC | PIK3CA | ENSCAFT00000017863.3 | chr34:12675674A>T | | c.3140A>T | p.His1047Leu | Missense variant | 20.5% |
| CCB060143 | cPAC | TP53 | ENSCAFT00000026465.3 | chr5:32563916C>T | rs851387419 | c.491G>A | p.Arg164His | Missense variant | 55.4% |
| CCB060156 | cPAC | ERBB2 | ENSCAFT00000025936.3 | chr9:22765127A>T | | c.1976T>A | p.Val659Glu | Missense variant | 15.6% |
| CCB060156 | cPAC | TP53 | ENSCAFT00000026465.3 | chr5:32563971C>A | | c.436G>T | p.Val146Phe | Missense variant | 34.4% |
| CCB070114 | cPAC | ERBB2 | ENSCAFT00000025936.3 | chr9:22765127A>T | | c.1976T>A | p.Val659Glu | Missense variant | 18.5% |
| CCB070201 | cPAC | VHL | ENSCAFT00000046552.2 | chr20:8210949A>G | | c.334T>C | p.Tyr112His | Missense variant | 26.5% |
| CCB070294 | cPAC | ERBB2 | ENSCAFT00000025936.3 | chr9:22765127A>T | | c.1976T>A | p.Val659Glu | Missense variant | 9.42% |
| CCB070294 | cPAC | SMAD4 | ENSCAFT00000000266.3 | chr1:238825750>A | | c.1572G>T | p.Trp524Cys | Missense variant | 19.3% |
| CCB070295 | cPAC | ERBB2 | ENSCAFT00000025936.3 | chr9:22765127A>T | | c.1976T>A | p.Val659Glu | Missense variant | 40.8% |
| CCB070295 | cPAC | TP53 | ENSCAFT00000026465.3 | chr5:32563388C>T | rs851620436 | c.716G>A | p.Arg239Gln | Missense variant | 57.6% |
| CLAC | cPAC | ERBB2 | ENSCAFT00000025936.3 | chr5:32563028C>T | rs852440243 | c.815G>A | p.Arg272His | Missense variant | 99.5% |
| OSU361939 | cPAC | ERBB2 | ENSCAFT00000025936.3 | chr9:22765127A>T | | c.1976T>A | p.Val659Glu | Missense variant | 38.8% |
| OSU361645 | cPAC | KRAS | ENSCAFT00000010525.3 | chr27:22261798G>T | | c.35G>T | p.Gly12Val | Missense variant | 56.8% |
| OSU388285 | cPAC | ERBB2 | ENSCAFT00000025936.3 | chr9:22765127A>T | | c.1976T>A | p.Val659Glu | Missense variant | 17.0% |
| OSU389339 | cPAC | ERBB2 | ENSCAFT00000025936.3 | chr9:22765127A>T | | c.1976T>A | p.Val659Glu | Missense variant | 47.7% |
| OSU389339 | cPAC | PTEN | ENSCAFT00000024821.3 | chr26:37906323C>T | | c.574C>T | p.Gln192* | Stop-gained variant | 23.2% |
| OSU415281 | cPAC | HRAS | ENSCAFT00000048281.1 | chr18:25644252A>G | | c.233T>C | p.Phe78Ser | Missense variant | 20.9% |
| OSU419040 | cPAC | CSF1R | ENSCAFT00000028942.3 | chr4:58991931A>G | | c.953A>G | p.Lys318Arg | Missense variant | 24.6% |
| OSU419040 | cPAC | ERBB2 | ENSCAFT00000025936.3 | chr9:22765113C>T | | c.1990G>A | p.Ala664Thr | Missense variant | 17.9% |

FIG. 14A

| Patient ID | Tumor Type | Gene symbol | Transcript accession | Nucleotide (genomic) | rs ID (dbSNP151) | Nucleotide (cDNA) | Amino acid (protein) | Mutation type | % mutant reads |
|---|---|---|---|---|---|---|---|---|---|
| OSU419040 | cPAC | ERBB2 | ENSCAFT00000025936.3 | chr9:22765127A>T | | c.1976T>A | p.Val659Glu | Missense variant | 6.39% |
| OSU419040 | cPAC | VHL | ENSCAFT00000046552.2 | chr20:8210966C>T | | c.317G>A | p.Gly106Asp | Missense variant | 28.6% |
| OSU424354 | cPAC | ERBB2 | ENSCAFT00000025936.3 | chr9:22765127A>T | | c.1976T>A | p.Val659Glu | Missense variant | 8.52% |
| OSU426073 | cPAC | ERBB2 | ENSCAFT00000025936.3 | chr9:22765127A>T | | c.1976T>A | p.Val659Glu | Missense variant | 17.8% |
| OSU429271 | cPAC | TP53 | ENSCAFT00000026465.3 | chr5:32563389G>C | | c.715C>G | p.Arg239Gly | Missense variant | 63.4% |
| iSUK9PADSnicke | cPAC | KRAS | ENSCAFT00000010525.3 | chr27:22261798G>A | rs852661628 | c.35G>A | p.Gly12Asp | Missense variant | 73.4% |
| iSUK9PADSnicke | cPAC | SMARCB1 | ENSCAFT00000022399.3 | chr26:28716263C>T | | c.628G>A | p.Glu210Lys | Missense variant | 30.5% |
| iSUK9PADSnicke | cPAC | TP53 | ENSCAFT00000026465.3 | chr5:32563077C>A | | c.766G>T | p.Gly256* | Stop-gained variant | 98.4% |
| SUK9PAPADOsc | cPAC | ERBB2 | ENSCAFT00000025936.3 | chr9:22765127A>T | | c.1976T>A | p.Val659Glu | Missense variant | 15.0% |
| SUK9PAPADOsc | cPAC | SMAD4 | ENSCAFT00000000266.3 | chr1:238944220C>A | | c.1051G>T | p.Asp351Tyr | Missense variant | 29.7% |
| DSUK9PAPADRe | cPAC | ERBB2 | ENSCAFT00000025936.3 | chr9:22765127A>T | | c.1976T>A | p.Val659Glu | Missense variant | 51.9% |
| DSUK9PAPADRe | cPAC | SMAD4 | ENSCAFT00000000266.3 | chr1:238944220C>A | | c.1051G>T | p.Asp351Tyr | Missense variant | 99.3% |
| CCB010105 | cPASC | KRAS | ENSCAFT00000010525.3 | chr27:22277969C>A | | c.181C>A | p.Gln61Lys | Missense variant | 29.4% |
| CCB010105 | cPASC | TP53 | ENSCAFT00000026465.3 | chr5:32563968G>A | | c.439C>T | p.Arg147Cys | Missense variant | 22.0% |
| CCB040011 | cPASC | EGFR | ENSCAFT00000055575.3 | chr18:60163656G>A | | c.2176G>A | p.Ala726Thr | Missense variant | 23.4% |
| CCB040011 | cPASC | MET | ENSCAFT00000049462.2 | chr14:55699187A>G | | c.3805A>G | p.Met1269Val | Missense variant | 34.5% |
| CCB040011 | cPASC | PTPRJ | ENSCAFT00000013154.3 | chr18:41608559T>C | | c.2527A>G | p.Ser843Gly | Missense variant | 26.9% |
| CCB040385 | cPASC | PTEN | ENSCAFT00000024821.3 | chr26:37910052T>G | | c.893T>G | p.Leu298* | Stop-gained variant | 59.5% |
| OSU422557 | cPASC | HRAS | ENSCAFT00000048281.1 | chr18:25644303T>A | | c.182A>T | p.Gln61Leu | Missense variant | 11.3% |
| OSU422557 | cPASC | KIT | ENSCAFT00000049830.2 | chr13:47187859A>G | | c.2482-4A>G | | Splice region variant | 23.3% |
| OSUK9PADSQ | cPASC | PTEN | ENSCAFT00000024821.3 | chr26:37886124C>T | | c.322C>T | p.Arg108* | Stop-gained variant | 100.0% |
| OSUK9PADSQ | cPASC | VHL | ENSCAFT00000046552.2 | chr20:8210993G>A | | c.290C>T | p.Pro97Leu | Missense variant | 24.9% |
| CCB010131 | cPSCC | PTPN11 | ENSCAFT00000014133.3 | chr26:10052797G>T | | c.1508G>T | p.Gly503Val | Missense variant | 50.8% |
| OSULSCC1 | cPSCC | BRAF | ENSCAFT00000003305.4 | chr16:8296284T>A | | c.1763T>A | p.Val588Glu | Missense variant | 50.5% |

FIG. 14B

Supplementary Table 10. Germline SNPs in COSMIC Tier 1 cancer genes identified by exome and panel sequencing in primary canine lung cancers.

| Patient ID | Gene symbol | Transcript accession | Nucleotide (genomic) | rsID (dbSNP151) | DogSD AF | Nucleotide (cDNA) | Amino acid (protein) | Variant type | Variant germline zygosity | Variant tumor zygosity |
|---|---|---|---|---|---|---|---|---|---|---|
| CCB010387 | CHRNA3 | ENSCAFT00000002688 | chr13:38339387G>GC | . | . | c.1237dupC | p.Arg413fs | Frameshift variant | Heterozygous | Heterozygous |
| CCB010387 | CHRNA3 | ENSCAFT00000002688 | chr13:38339420C>A | . | 4% | c.1268C>A | p.Ala423Glu | Missense variant | Heterozygous | Heterozygous |
| CCB050354 | CHRNA3 | ENSCAFT00000002689 | chr13:38339420C>A | . | 4% | c.1268C>A | p.Ala423Glu | Missense variant | Heterozygous | Heterozygous |
| CCB050354 | CYP1B1 | ENSCAFT00000009970 | chr17:30277509C>G | . | 3% | c.278G>C | p.Arg93Pro | Missense variant | Homozygous | Homozygous |
| OSU431895 | DNAH11 | ENSCAFT00000004311 | chr14:35518795G>A | . | 8% | c.2851G>A | p.Val951Ile | Missense variant | Heterozygous | Heterozygous |
| OSU431895 | DNAH11 | ENSCAFT00000004311 | chr14:35533763C>T | . | . | c.4378C>T | p.Arg1460Trp | Missense variant | Heterozygous | Heterozygous |
| OSU396622 | HER2 | ENSCAFT00000025936 | chr9:22761249C>T | . | 4% | c.3565G>A | p.Val1189Ile | Missense variant | Heterozygous | Heterozygous |
| OSU431895 | HER2 | ENSCAFT00000025936 | chr9:22761249C>T | . | 4% | c.3565G>A | p.Val1189Ile | Missense variant | Heterozygous | Heterozygous |

FIG. 15

Supplementary Table 11. Multi-platform validation of HER2 mutations.

| Patient ID | Tumor or Cell Line | Gene symbol | Transcript accession | Mutation (genomic nucleotide) | Nucleotide (cDNA) | Amino acid (protein) | Mutation type | Exome |
|---|---|---|---|---|---|---|---|---|
| BACA | Cell Line | HER2 | ENSCAFT00000025936.3 | WT | n/a | n/a | WT | |
| CLAC | Cell Line | HER2 | ENSCAFT00000025936.3 | WT | n/a | n/a | WT | |
| OSUK9PADBa | Cell Line | HER2 | ENSCAFT00000025936.3 | WT | n/a | n/a | WT | |
| OSUK9PADi | Cell Line | HER2 | ENSCAFT00000025936.3 | WT | n/a | n/a | WT | |
| OSUK9PADSn | Cell Line | HER2 | ENSCAFT00000025936.3 | WT | n/a | n/a | WT | |
| OSUK9PADSQ | Cell Line | HER2 | ENSCAFT00000025936.3 | WT | n/a | n/a | WT | |
| OSUK9PAPADO Passage 15 | Cell Line | HER2 | ENSCAFT00000025936.3 | chr9:22765127A>T | c.1976T>A | p.Val659Glu | Missense variant | |
| OSUK9PAPADO Passage 4 | Cell Line | HER2 | ENSCAFT00000025936.3 | chr9:22765127A>T | c.1976T>A | p.Val659Glu | Missense variant | 44% |
| OSUK9PAPADRe | Cell Line | HER2 | ENSCAFT00000025936.4 | chr9:22765127A>T | c.1976T>A | p.Val659Glu | Missense variant | |
| OSUK9PAPADRi | Cell Line | HER2 | ENSCAFT00000025936.3 | WT | n/a | n/a | WT | |
| OSULSCC1 | Cell Line | HER2 | ENSCAFT00000025936.3 | WT | n/a | n/a | WT | |
| OSUPaPADSh | Cell Line | HER2 | ENSCAFT00000025936.3 | chr9:22765127A>T | c.1976T>A | p.Val659Glu | Missense variant | |
| CCB010120 | Tumor | HER2 | ENSCAFT00000025936.3 | chr9:22765127A>T | c.1976T>A | p.Val659Glu | Missense variant | 54% |
| CCB010387 | Tumor | HER2 | ENSCAFT00000025936.3 | chr9:22765127A>T | c.1976T>A | p.Val659Glu | Missense variant | |
| CCB020051 | Tumor | HER2 | ENSCAFT00000025936.3 | chr9:22765127A>T | c.1976T>A | p.Val659Glu | Missense variant | |
| CCB020198 | Tumor | HER2 | ENSCAFT00000025936.3 | chr9:22765127A>T | c.1978T>A | p.Val659Glu | Missense variant | |
| CCB040005 | Tumor | HER2 | ENSCAFT00000025936.3 | chr9:22765127A>T | c.1976T>A | p.Val659Glu | Missense variant | |
| CCB040068 | Tumor | HER2 | ENSCAFT00000025936.3 | chr9:22765127A>T | c.1976T>A | p.Val659Glu | Missense variant | |
| CCB040149 | Tumor | HER2 | ENSCAFT00000025936.3 | chr9:22765127A>T | c.1976T>A | p.Val659Glu | Missense variant | |
| CCB040231 | Tumor | HER2 | ENSCAFT00000025936.3 | chr9:22765127A>T | c.1976T>A | p.Val659Glu | Missense variant | 35% |
| CCB050227 | Tumor | HER2 | ENSCAFT00000025936.3 | chr9:22765127A>T | c.1976T>A | p.Val659Glu | Missense variant | |
| CCB050243 | Tumor | HER2 | ENSCAFT00000025936.3 | chr9:22765077T>C | c.2026A>G | p.Lys676Glu | Missense variant | |
| CCB050260 | Tumor | HER2 | ENSCAFT00000025936.3 | chr9:22765127A>T | c.1976T>A | p.Val659Glu | Missense variant | |
| CCB050345 | Tumor | HER2 | ENSCAFT00000025936.3 | chr9:22765127A>T | c.1976T>A | p.Val659Glu | Missense variant | |
| CCB050354 | Tumor | HER2 | ENSCAFT00000025936.3 | chr9:22765127A>T | c.1976T>A | p.Val659Glu | Missense variant | |
| CCB050362 | Tumor | HER2 | ENSCAFT00000025936.3 | chr9:22765127A>T | c.1976T>A | p.Val659Glu | Missense variant | |
| CCB060156 | Tumor | HER2 | ENSCAFT00000025936.3 | chr9:22765127A>T | c.1978T>A | p.Val659Glu | Missense variant | |
| CCB070114 | Tumor | HER2 | ENSCAFT00000025936.3 | chr9:22765127A>T | c.1976T>A | p.Val659Glu | Missense variant | |
| CCB070294 | Tumor | HER2 | ENSCAFT00000025936.3 | chr9:22765127A>T | c.1976T>A | p.Val659Glu | Missense variant | |
| CCB070295 | Tumor | HER2 | ENSCAFT00000025936.3 | chr9:22765127A>T | c.1976T>A | p.Val659Glu | Missense variant | |
| OSU361939 | Tumor | HER2 | ENSCAFT00000025936.3 | chr9:22765127A>T | c.1976T>A | p.Val659Glu | Missense variant | |
| OSU382285 | Tumor | HER2 | ENSCAFT00000025936.3 | chr9:22765127A>T | c.1976T>A | p.Val659Glu | Missense variant | |
| OSU389339 | Tumor | HER2 | ENSCAFT00000025936.3 | chr9:22765127A>T | c.1976T>A | p.Val659Glu | Missense variant | |
| OSU396622 | Tumor | HER2 | ENSCAFT00000025936.3 | chr9:22765113C>T | c.1990G>A | p.Ala664Thr | Missense variant | 20% |
| OSU419040 | Tumor | HER2 | ENSCAFT00000025936.3 | chr9:22765127A>T | c.1976T>A | p.Val659Glu | Missense variant | |
| OSU419040 | Tumor | HER2 | ENSCAFT00000025936.3 | chr9:22765127A>T | c.1976T>A | p.Val659Glu | Missense variant | |
| OSU424354 | Tumor | HER2 | ENSCAFT00000025936.3 | chr9:22765127A>T | c.1976T>A | p.Val659Glu | Missense variant | |
| OSU428073 | Tumor | HER2 | ENSCAFT00000025936.3 | chr9:22765127A>T | c.1976T>A | p.Val659Glu | Missense variant | |

FIG. 16A

| Patient ID | Targeted panel | HER2 Mutant reads (%) or Profiling Result |  |  | aCGH from Clemente-Vicario et al[21] |
|---|---|---|---|---|---|
| | | HER2 659 locus Sanger sequencing | HER2 all coding regions Sanger sequencing | Digital droplet PCR | |
| BACA | 0.0% | WT | WT | 0.0% | No HER2 Amp |
| CLAC | 0.0% | WT | WT | 0.0% | No HER2 Amp |
| OSUK9PADBa | 0.0% | | WT | 0.0% | |
| OSUK9PADl | 0.0% | WT | | | |
| OSUK9PADSn | 0.0% | WT | WT | 0.0% | |
| OSUK9PADSQ | 0.0% | WT | WT | 0.0% | |
| OSUK9PAPADO Passage 15 | | | | 0.0% | |
| OSUK9PAPADO Passage 4 | 15.0% | | | 16.0% | |
| OSUK9PAPADRe | 51.9% | | | 50.5% | |
| OSUK9PAPADRi | | Mut | | | |
| OSULSCC1 | 0.0% | WT | WT | 0.0% | |
| OSUPaPADSh | 0.0% | Mut | | | |
| CCB010120 | 33.8% | Mut | | | |
| CCB010387 | 46.7% | | | 39.0% | |
| CCB020051 | 44.0% | Mut | | | |
| CCB020198 | 34.1% | Mut | | | |
| CCB040005 | 34.8% | Mut | | | |
| CCB040068 | 34.0% | | | | |
| CCB040149 | 22.3% | | | | |
| CCB040231 | 20.3% | | | | |
| CCB050227 | | | | 59.2% | |
| CCB050243 | 11.3% | WT | | 33.0% | |
| CCB050260 | 10.0% | WT | | 10.5% | |
| CCB050345 | 30.5% | | | | |
| CCB050354 | 36.9% | | | | |
| CCB050362 | 10.6% | Mut | | | |
| CCB060156 | 15.6% | Mut | | | |
| CCB070114 | 18.5% | Mut | | | |

FIG. 16B

| Patient ID | Targeted panel | HER2 659 locus Sanger sequencing | HER2 all coding regions Sanger sequencing | Digital droplet PCR | aCGH from Clemente-Vicario et al[21] |
|---|---|---|---|---|---|
| CCB070294 | 9.42% | . | . | 10.4% | . |
| CCB070295 | 40.8% | . | . | 36.5% | . |
| OSU361939 | 38.8% | Mut | . | . | . |
| OSU388285 | 17.0% | Mut | . | . | . |
| OSU389339 | 47.7% | Mut | . | . | . |
| OSU396622 | . | . | . | 27.0% | . |
| OSU419040 | 17.9% | . | . | 11.6% | . |
| OSU419040 | 8.39% | . | . | 11.6% | . |
| OSU424354 | 8.52% | Mut | . | . | . |
| OSU428073 | 17.8% | Mut | . | . | . |

FIG. 16C

Supplementary Table 12. Non-invasive detection of *HER2* V659E in the plasma of primary canine lung cancer patients.

| Sample ID | Sample type | $HER2^{V659E}$ allele frequency in tumor | Total droplets assayed | Poisson corrected mutant droplet count ($HER2^{V659E}$) | Poisson corrected wild type droplet count ($HER2^{V659E}$) | $HER2^{V659E}$ allele frequency by ddPCR |
|---|---|---|---|---|---|---|
| Bioreclamation IVT | Canine plasma (negative control) | na | 10000000 | 0 | 207 | 0.0% |
| Bioreclamation IVT | Canine plasma (negative control) | na | 10000000 | 0 | 313 | 0.0% |
| Bioreclamation IVT | Canine plasma (negative control) | na | 10000000 | 0 | 237 | 0.0% |
| Bioreclamation IVT | Canine plasma (negative control) | na | 10000000 | 0 | 202 | 0.0% |
| Bioreclamation IVT | Canine plasma (negative control) | na | 10000000 | 1 | 241 | 0.5% |
| Bioreclamation IVT | Canine plasma (negative control) | na | 10000000 | 0 | 186 | 0.0% |
| CCB020245 | Canine plasma | 0.0% | 10000000 | 0 | 97 | 0.0% |
| OSU389339 | Canine plasma | 47.7% | 10000000 | 1 | 232 | 0.6% |
| CCB020203 | Canine plasma | 0.0% | 10000000 | 0 | 510 | 0.0% |
| OSU429271 | Canine plasma | 0.0% | 10000000 | 0 | 221 | 0.0% |
| CCB020051 | Canine plasma | 44% | 10000000 | 11 | 493 | 2.3% |
| OSU361939 | Canine plasma | 38.8% | 10000000 | 0 | 517 | 0.0% |
| OSU428073 | Canine plasma | 17.8% | 10000000 | 58 | 3022 | 1.9% |
| CCB020293 | Canine plasma | 0.0% | 10000000 | 0 | 1936 | 0.0% |
| OSU431895 | Canine plasma | 0.0% | 10000000 | 0 | 846 | 0.0% |
| CCB020198 | Canine plasma | 34.1% | 10000000 | 0 | 420 | 0.0% |
| OSU388285 | Canine plasma | 17.0% | 10000000 | 0 | 454 | 0.0% |
| NTC | Water (negative control) | na | 10000000 | 0 | 0 | 0.00% |
| NTC | Water (negative control) | na | 10000000 | 0 | 0 | 0.00% |
| NTC | Water (negative control) | na | 10000000 | 0 | 0 | 0.00% |
| NTC | Water (negative control) | na | 10000000 | 0 | 0 | 0.00% |
| NTC | Water (negative control) | na | 10000000 | 0 | 1 | 0.00% |
| NTC | Water (negative control) | na | 10000000 | 0 | 0 | 0.00% |
| CCB030383 | Tumor (negative control) | 0.0% | 10000000 | 0 | 14584 | 0.0% |
| OSU415281 | Tumor (negative control) | 0.0% | 10000000 | 1 | 16164 | 0.0% |
| OSU396622 | Tumor (positive control) | 19.5% | 10000000 | 2696 | 7254 | 27.1% |
| CCB050227 | Tumor (positive control) | 54.16% | 10000000 | 14889 | 10248 | 59.2% |
| CCB010387 | Tumor (positive control) | 43.9% | 10000000 | 6486 | 10122 | 39.1% |
| CCB050260 | Tumor (positive control) | 10.0% | 10000000 | 1970 | 17222 | 10.3% |
| CCB050260 | Tumor (positive control) | 10.0% | 10000000 | 1963 | 17194 | 10.2% |
| CCB050260 | Tumor (positive control) | 10.0% | 10000000 | 2123 | 18109 | 10.5% |

NTC = Non-template control
na = not applicable

FIG. 17

Supplementary Table 13: HER2 protein expression and quantification by immunohistochemistry.

| Patient ID | HER2 Mutation Status | Slide ID | Normal Lung Ratio | Normal Lung % | Necrosis Area (um²) | Her2 Connectivity | Her2 Score | Specimen Total Area (um²) | Tumor Area (um²) | Tumor Area Ratio | Tumor Area % |
|---|---|---|---|---|---|---|---|---|---|---|---|
| OSU381645 | WT | 31 07-2924-1 HER2 Cell Sig #4290 RA W | 0.340721011 | 34.07210159 | 13714500 | 0.514878988 | 2 | 2737406902 | 166064000 | 0.608834029 | 60.88340896 |
| OSU421496 | WT | 31 12-369-7 HER2 Cell Sig #4290 RA W | 0.008962645 | 0.862644982 | 45009500 | 0.256612986 | 1 | 4425000000 | 393710016 | 0.889741004 | 88.97409821 |
| CCB020293 | WT | 31 12-524-2 HER2 Cell Sig #4290 RA W | 0.053174101 | 5.317409992 | 0 | 0.366397993 | 1 | 2858160000 | 364611008 | 0.945527971 | 94.55280304 |
| OSU454408 | WT | 31 16-447-1 HER2 Cell Sig #4290 RA WL | 0.0152054 | 1.520539999 | 13918100 | 0.209976003 | 1 | 2028340000 | 185584992 | 0.915636003 | 91.56359863 |
| OSU424354 | V659E | 31 12-1203-3 HER2 Cell Sig #4290 RA W | 0.125456005 | 12.54559994 | 7454920 | 0.127762005 | 1 | 4632070080 | 396947808 | 0.856953879 | 85.69539642 |
| OSU388285 | V659E | 21 07-3241-3 HER2 Cell Sig #4290 RA W | 0.009866458 | 0.986656029 | 13320800 | 0.161900997 | 1 | 269351008 | 253427008 | 0.940877974 | 94.08779907 |
| OSU389339 | V659E | 7-2755-3 HER2 Cell Sig #4290 RA W (2) | 0.0108913 | 1.089130044 | 10340400 | 0.239398003 | 1 | 358744992 | 344496992 | 0.960285008 | 96.02850342 |
| OSU418040 | A664T | 31 11-2041-3 HER2 Cell Sig #4290 RA W | 0.0464551 | 4.645510197 | 2537650 | 0.184890002 | 1 | 247571008 | 233212992 | 0.942003012 | 94.20030212 |

| Patient ID | Normal Lung Area (um²) | | | Necrosis Ratio | Necrosis % | | Tumor Positive Stain Area (um²) | Tumor Positive Stain Area Ratio | Tumor Positive Stain % |
|---|---|---|---|---|---|---|---|---|---|
| OSU381645 | 92928400 | | | 0.050283098 | 5.028393944 | | 99146800 | 0.597075665 | 59.70756501 |
| OSU421496 | 2932200 | | | 0.101715997 | 10.17160034 | | 121066000 | 0.307500432 | 30.75004321 |
| CCB020293 | 20604800 | | | 0 | 0 | | 147372992 | 0.404192382 | 40.41923828 |
| OSU454408 | 3081890 | | | 0.068668798 | 6.866687984 | | 107836000 | 0.581059917 | 58.10599167 |
| OSU424354 | 58112200 | | | 0.0160942 | 1.609419942 | | 188723008 | 0.475436278 | 47.54362779 |
| OSU388285 | 2603700 | | | 0.049454998 | 4.945498897 | | 109380000 | 0.431603565 | 43.16035645 |
| OSU389339 | 3907220 | | | 0.0283238 | 2.832380029 | | 123259200 | 0.357794126 | 35.77794125 |
| OSU418040 | 11508000 | | | 0.0102502 | 1.025020003 | | 59010800 | 0.253033393 | 25.30339305 |

FIG. 18A

| Patient ID | Tumor Negative Stain Area (μm²) | Tumor Negative Stain Ratio | Tumor Negative Stain % | Tumor Mean Stain Intensity [Optical Density (OD)] | Tumor Mean Stain Intensity Ratio | Tumor Mean Stain Intensity % |
|---|---|---|---|---|---|---|
| OSU381645 | 66323772 | 0.399410866 | 39.94108663 | 188.3328926 | 0.738560021 | 73.85600281 |
| OSU421496 | 269952000 | 0.685662008 | 68.56620076 | 207.6439972 | 0.814291 | 81.42910004 |
| CCB020293 | 212390000 | 0.582511212 | 58.25112115 | 199.7879944 | 0.783483992 | 78.3483983 |
| OSU454408 | 80216896 | 0.432238055 | 43.22380551 | 183.6880035 | 0.720346987 | 72.03469849 |
| OSU424354 | 210760992 | 0.530954983 | 53.09549833 | 203.7700043 | 0.790097002 | 79.00969849 |
| OSU388285 | 146023008 | 0.576193552 | 57.61935523 | 200.0599976 | 0.784546971 | 78.45469666 |
| OSU389339 | 224224000 | 0.650873608 | 65.08736076 | 203.2279968 | 0.796971977 | 79.69719696 |
| OSU419040 | 174642000 | 0.748851934 | 74.88519336 | 205.3119965 | 0.805144012 | 80.51439667 |

| Patient ID | Tumor Maximum Stain Intensity (OD) | Tumor Maximum Stain Intensity Ratio | Tumor Maximum Stain Intensity % | Tumor Minimum Stain Intensity (OD) | Tumor Minimum Stain Intensity Ratio | Tumor Minimum Stain Intensity % |
|---|---|---|---|---|---|---|
| OSU381645 | 247.3170013 | 0.969869018 | 96.98690033 | 129.5850067 | 0.508177996 | 50.81779861 |
| OSU421496 | 248.1320038 | 0.973085972 | 97.30860248 | 120.7210007 | 0.473471014 | 47.34170151 |
| CCB020293 | 248.4869995 | 0.974458992 | 97.44589996 | 150.6159973 | 0.590651989 | 59.06520081 |
| OSU454408 | 245.0140076 | 0.96083802 | 96.0838127 | 118.0469971 | 0.46292901 | 46.29290009 |
| OSU424354 | 245.8159943 | 0.963982399 | 96.39823999 | 161.6629944 | 0.633973002 | 63.39730072 |
| OSU388285 | 246.3119965 | 0.965930998 | 96.5931015 | 148.2330017 | 0.581306994 | 58.13069916 |
| OSU389339 | 246.3410034 | 0.966041982 | 96.60420227 | 149.1239929 | 0.584798992 | 58.47990036 |
| OSU419040 | 241.3739929 | 0.946584019 | 94.65840259 | 102.4860001 | 0.401905 | 40.19049835 |

FIG. 18B

IDENTIFICATION OF HER2 MUTATIONS IN LUNG CANCER AND METHODS OF TREATMENT

CROSS-REFERENCE TO RELATED APPLICATIONS

The present application is the U.S. National Stage of International Application No. PCT/US2019/065715, filed on Dec. 11, 2019, which claims the benefit of U.S. Provisional Patent Application No. 62/778,282, filed on Dec. 11, 2018, the contents of each of which are incorporated herein by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "279PCT_Sequence_Listing_ST25" created on Dec. 11, 2019, and having a size of 1.51 kilobytes, and is filed concurrently with the specification. The sequence listing contained in this ASCII-formatted document is part of the specification and is herein incorporated by reference in its entirety.

FIELD

The present invention relates to methods for assessing and treating cancer, and in particular, canine lung cancers, and most particularly, canine pulmonary adenocarcinomas, adenosquamous and squamous cell carcinomas.

BACKGROUND

Naturally occurring primary canine lung cancer is clinically challenging (1), with a disease course and underlying biology that resemble human lung cancer in never-smokers. Human never-smoker lung cancer accounts for 10% to 25% of lung cancers, causes approximately 26,000 deaths annually, and has a high incidence of erb-B family gene mutations such as those affecting epidermal growth factor receptor (EGFR). Although the incidence of smoking-related lung cancer is decreasing, lung cancer incidence in never-smokers is increasing (2). Never-smoker lung cancer is primarily non-small cell lung cancer (NSCLC), arising from lung tissue, as opposed to small cell lung cancer arising in bronchi of smokers. NSCLC histologies include adenocarcinoma (AC) and squamous cell carcinoma (SCC). The etiology of never-smoker lung cancer is also distinct from that of smokers. It is associated with factors including environmental exposures (secondhand smoke, radon, asbestos, arsenic, silica, and pollution) as well as age, sex, family history, and genetic loci (3). Unique genomic characteristics of human never-smoker lung cancer include low somatic mutation burden, enrichment for C:G>T:A transitions, and somatic activating point mutations or fusions affecting EGFR (45%), ALK (5%-11%), ROS (1.5%-6%), HER2 (3%-5%), and RET (2%) (4). The five-year overall survival is estimated at 23%, but outcomes are dependent on molecular subtype and treatment regimen. For example, EGFR inhibitors can improve outcomes in EGFR-mutant lung cancers; however, 85% of never-smoker lung AC and SCC cases are EGFR wild-type (WT) in the United States. Clinical trials of immune-checkpoint inhibitors have recently shown improved outcomes for human lung cancers, but analysis of large phase II immunotherapy trials suggests that benefits are limited in low-mutation-burden (≤10 mutations/Mb) cases such as those found in never-smokers (5).

Lung cancer in pet dogs has limited standard of care beyond surgery, and little is known of canine lung cancer molecular underpinnings (1). Primary lung tumors typically arise in older dogs (≥11 years) and resemble human NSCLC histotypes including canine pulmonary adenocarcinoma (cPAC), canine adenosquamous carcinoma (cPASC), and canine pulmonary squamous cell carcinoma (cPSCC). These subtypes collectively represent 13% to 15% of primary lung tumors (6,7). Patients are often diagnosed late with lesions incidentally discovered during routine geriatric evaluation or due to nonspecific symptoms including dyspnea (6% to 24%) and cough (52% to 93%) that do not manifest until the tumor is more than 3 centimeters (cm). The detection of canine lung cancers has significantly increased over the past 20 years not only because of improved animal healthcare and diagnostics, but also possibly due to increased companion animal exposures to pollutants. These tumors can be diagnostically challenging. Rates at which ultrasound or CT-guided fine-needle aspirates of the pulmonary mass provide cytologic diagnosis range from 38% to 90% of cases, varying broadly based on tumor accessibility and aspirate quality. At diagnosis, 71% of malignant canine lung tumors show signs of invasion and 23% show distant metastasis. Partial or complete lung lobectomy is standard of care, dependent on the extent of disease spread. Median survival is 345 days for localized disease without nodal involvement where surgical remission can be achieved, but only 60 days when nodes are involved. Responses to cytotoxic chemotherapy (cisplatin, vindesine, doxorubicin, and mitoxantrone) in the setting of disseminated disease are limited.

Targeted small molecules and immune-checkpoint inhibitors have not been extensively studied in part because the molecular underpinnings of canine lung cancer remain largely unknown. In naturally occurring canine NSCLC, although comprehensive genomic profiling has been limited, KRAS hotspot mutation prevalence estimates from targeted studies have varied from 0% to 25% (7-9). We have previously shown that EGFR mutation, overexpression, or phosphorylation is rare in cPAC compared with matched nonaffected chemotherapy-naïve lung tissue whereas significant overexpression and/or phosphorylation of PDGFRα, ALK, and HER2 are present (10).

SUMMARY

A need exists for improved biological understanding and development of new models to fuel translational research in never-smoker lung cancer. Further, a need exists for methods determining a sensitivity of a subject to a HER2 inhibitor and identification of one or more markers that indicate sensitivity of the subject to the HER2 inhibitor. Methods are provided herein for assessing, characterizing, diagnosing and treating lung cancer and for comparative oncology techniques.

In some embodiments, methods for treating lung cancer in a subject are disclosed. A biological sample from the subject is analyzed for a mutation in HER2. If a HER2 V659E mutation is present, the patient is treated with an inhibitor of HER2. The HER2 inhibitor may be selected from the group comprising trastuzumab, neratinib, lapatinib, erlotinib, and pertuzumab. In various embodiments, the subject is canine, and the lung cancer is pulmonary adenocarcinoma. The biological sample may be a tumor sample or a plasma sample. The step of analyzing the biological sample may comprise subjecting the sample to amplification and exome sequencing.

In various embodiments, the methods include receiving a biological sample from the subject, adding to a mixture comprising the sample a first primer consisting of SEQ ID NO: 1 and a second primer consisting of SEQ ID NO: 2, subjecting the mixture to conditions that allow nucleic acid amplification, detecting the presence of one or more markers selected from the group consisting of HER2 V659E, HER2 A664T, and HER2 K676E by detecting the nucleic acid amplification, and treating the subject with an inhibitor of HER2 if one or more of the markers is present. The detecting step may comprise sequencing a product of the nucleic acid amplification. The HER2 inhibitor may be selected from the group comprising trastuzumab, neratinib, lapatinib, erlotinib, and pertuzumab. The method may further include adding to the mixture a probe consisting of SEQ ID NO: 3, for example, prior to detecting the nucleic acid amplification.

In various embodiments, the methods of treating lung cancer in a subject include receiving a biological sample from the subject, analyzing the biological sample for one or more mutations selected from the group consisting of HER2 V659E, HER2 A664T, HER2 K676E, KRAS G12D/V, SMAD4 D351Y/G, and TP53 R239Q/G, and administering, if one or more of the mutations is present, a therapeutically effective amount of a pharmaceutical composition selected from the group consisting of trastuzumab, neratinib, lapatinib, erlotinib, and pertuzumab. The step of analyzing the biological sample may comprise subjecting the biological sample to amplification and exome sequencing. In various embodiments, the subject is canine, and the lung cancer is pulmonary adenocarcinoma. The biological sample may be a tumor sample or a plasma sample.

Methods of characterizing lung cancer in a canine subject are disclosed. The methods may include the steps of receiving a biological sample from the subject, adding to a mixture comprising the biological sample a first primer consisting of SEQ ID NO: 1 and a second primer consisting of SEQ ID NO: 2, subjecting the mixture to conditions that allow nucleic acid amplification, detecting the presence of one or more markers selected from the group consisting of HER2 V659E, HER2 A664T, and HER2 K676E by detecting the nucleic acid amplification, and determining a sensitivity of the canine subject to a HER2 inhibitor if the if one or more of the markers is present.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals may denote like elements.

FIG. 1A illustrates recurrent likely pathogenic somatic mutations in cancer genes identified in primary canine lung cancers through multi-platform sequencing; single nucleotide variants (SNVs) were determined from combined tumor/normal exome and/or amplicon sequencing across 88 total tumors and cell lines; FIG. 1B illustrates copy number variations (CVs) determined from tumor/normal exome data in five cPAC cases; FIG. 1C illustrates Somatic mutation burden (SNVs, CNVs, and SVs) identified by exome sequencing of five tumor/normal cPAC cases; FIG. 1D illustrates a distribution of somatic HER2 mutations within the HER2 protein identified in primary canine lung cancers; the length of the lollipops is proportional to the number of mutations found; FIG. 1E illustrates the detection of HER2 hotspot mutations in plasma from 11 canine primary lung cancer cases;

FIG. 2A illustrates downstream HER2 signaling in canine lung cancer cell lines; levels of phospho-Akt and Akt were assessed by Western blot under serum starvation in the presence and absence of EGFR activation by hNRG in HER2 V659E and HER2 WT cPAC cell lines; FIG. 2B illustrates canine lung cancer cell line sensitivity to neratinib; neratinib drug-dose-response studies in primary lung cancer cell lines; five canine cell lines (three HER2 WT and two HER2 V659E) and two human lung cancer positive controls with known HER2 activating mutations (BT474-HER2-amplified, and H1781-HER2 G776V) and HER2 inhibitor responses were treated with 14 neratinib doses ranging from 100 µM to $5.5 \times 10^{-2}$ nM for 72 hours with CellTiterGlo viability endpoints; survival is shown relative to DMSO vehicle control; FIG. 2C illustrates dose effect of the HER2 inhibitor neratinib on downstream AKT activation; phospho-AKT and AKT levels were assessed in two canine lung cancer cell lines—OSUK9PAPADO (HER2 WT) and OSUK9PAPADRi (HER2 V659E)—and compared to a well-characterized human lung cancer cell line (BT474, HER2-amplified) by Western blot under serum starvation in the presence of 5 doses (20-2000 nmol/L) of neratinib;

FIG. 3A shows affected breeds distribution; FIG. 3B shows age at diagnosis (Yr=years); FIG. 3C shows primary tumor location distribution; FIG. 3D shows sex distribution; FIG. 3E shows adenocarcinoma subtype distribution; FIG. 3F shows treatment of the canine lung cancer patients;

FIG. 4A illustrates the distribution of somatic single nucleotide mutation types in their trinucleotide context from tumor/normal exome sequencing of five cPAC cases; FIG. 4B illustrates the most common mutation signatures based on trinucleotide context and frequency of somatic single nucleotide mutations from tumor/normal exome sequencing of the five cPAC cases;

FIG. 5A illustrates canine papillary adenocarcinoma with intense, complete, circumferential membrane (white arrow) and lateral cytoplasmic membrane (black arrow) anti-HER2 antibody positive staining (brown) in a patient with wild-type HER2; FIG. 5B illustrates canine papillary adenocarcinoma with moderate cytoplasmic (black arrow) anti-HER2 antibody positive staining (light brown) in a patient with wild-type HER2, ×40; bar 50 µm; FIG. 5C illustrates anti-HER2 immunohistochemistry of a Grade 1 canine papillary adenocarcinoma wild type for HER2, ×20; FIG. 5D illustrates segmentation mark-up of the tumor from adjacent normal lung; tumor is identified by green, whereas red is area inside of tumor that contains no tissue, yellow represents areas of non-tumor such as necrosis or tumor stroma, ×20;

FIGS. 7A-7C illustrate a table of informatic tools utilized in primary canine lung cancer genomic analyses;

FIGS. 8A-8J illustrate a table of extended clinical and multiplatform annotation of primary canine lung cancer patients;

FIGS. 10A-10H illustrate a table of somatic coding single nucleotide variants (SNVs) identified by exome sequencing of primary canine lung cancers;

FIGS. 11A-11L illustrate a table of somatic coding copy number variations (CNVs) identified by exome sequencing of primary canine lung cancers;

FIG. 12 illustrates a table of somatic coding structural variants (SVs) identified by exome sequencing of primary canine lung cancers;

FIGS. 13A-13G illustrates a table of canine genomic regions covered by custom amplicon panel;

FIGS. 14A-14B illustrate a table of somatic coding SNVs identified by panel sequencing of primary canine lung cancers;

FIG. 15 illustrates a table of germline SNPs in COSMIC Tier 1 cancer genes identified by exome and panel sequencing in primary canine lung cancers;

FIGS. 16A-16C illustrate a table of results of multi-platform validation of HER2 mutations;

FIG. 17 illustrates a table of non-invasive detection of HER2 V659E mutations in the plasma of primary canine lung cancer patients;

FIGS. 18A-18B illustrate a set of tables showing HER2 protein expression and quantification by immunohistochemistry;

FIG. 20A illustrates normal lung tissue versus tumor tissue; FIG. 20B illustrates normal lung tissue versus HER2-wild-type tumor tissue versus HER2-mutant tumor tissue;

DETAILED DESCRIPTION

Figure 1A:
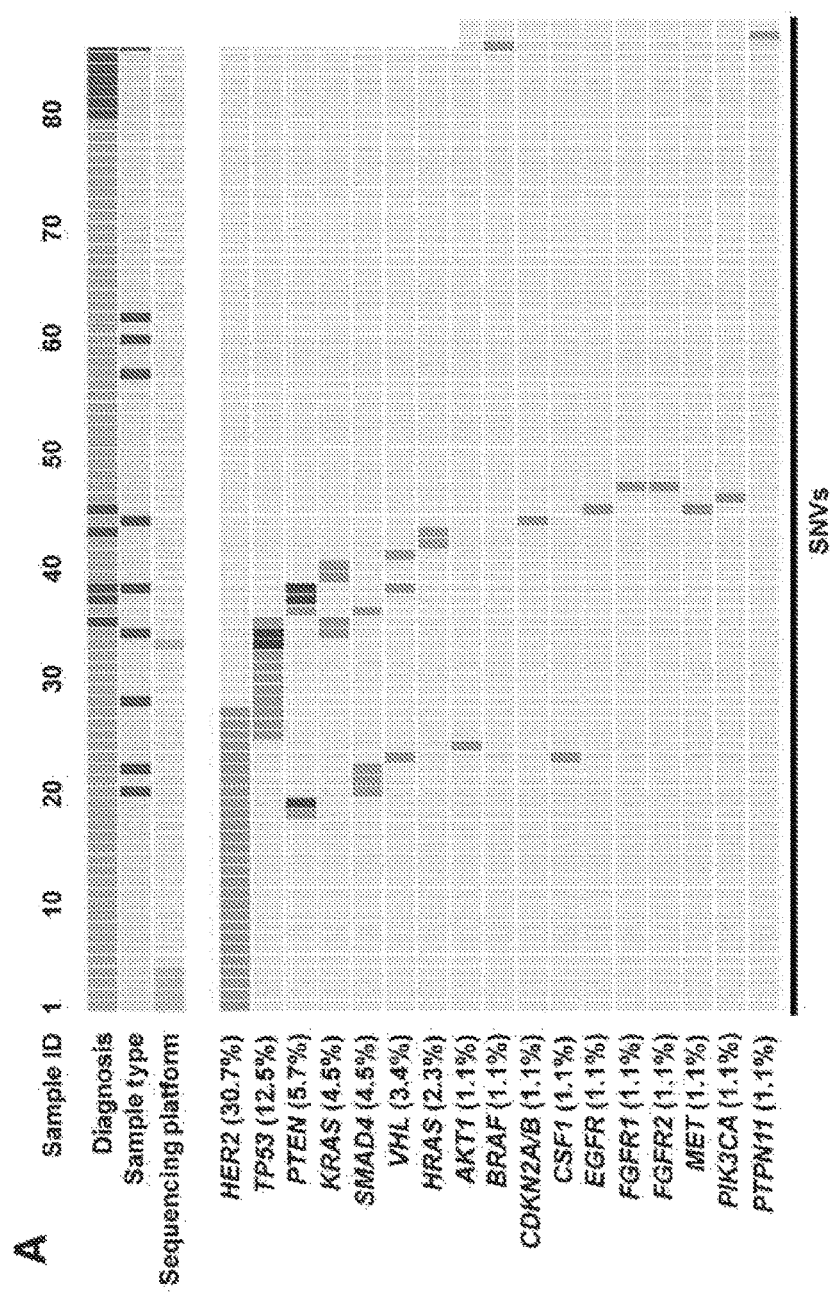
FIGS. 1A-1E illustrate the genomic landscape of primary canine lung cancer.
Figure 1B:
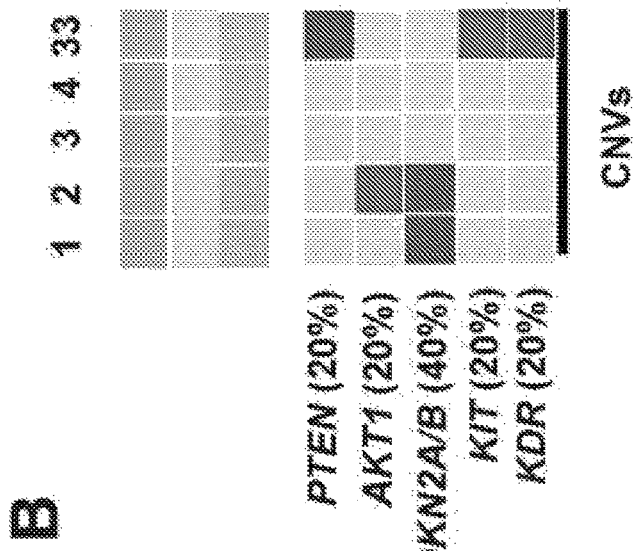
Figure 1C:
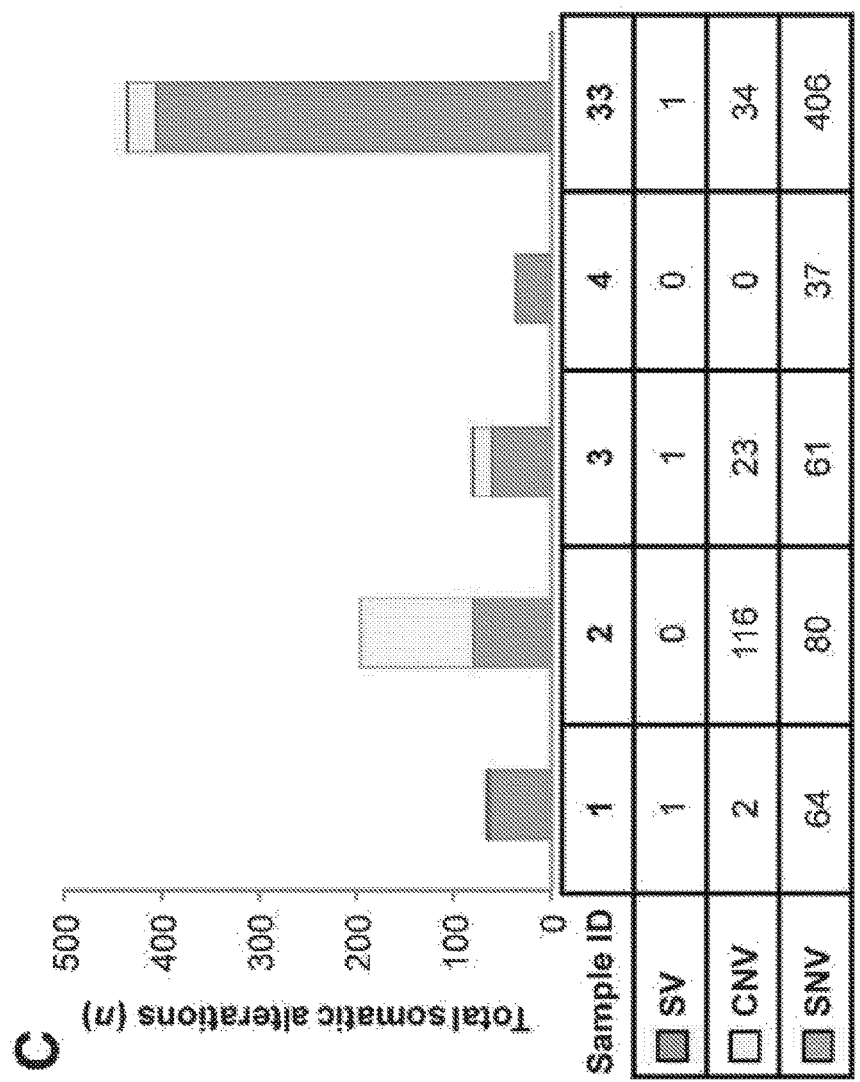

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

The present disclosure characterizes the genetic underpinnings of naturally occurring canine lung cancers and identified novel recurring mutations including HER2 V659E mutations occurring in 37% of canine pulmonary adenocarcinomas. The present disclosure further includes a digital PCR assay for detection of these recurrent hotspot mutations, including HER2 mutations.

The sample in the disclosed method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. In some embodiments, sample or biological sample may include a bodily tissue, fluid, or any other specimen that may be obtained from a living organism that may comprise additional living organisms. The subject may be any organism subject or susceptible to lung cancer including mammals, further including canines or humans.

As used herein, the term "subject" or "patient" is used in its broadest sense and may refer to any vertebrate including, without limitation, humans and other primates (e.g., chimpanzees and other apes and monkey species), domestic mammals (e.g., dogs and cats), laboratory animals (e.g., rodents such as mice, rats, and guinea pigs), farm animals (e.g., cattle, sheep, pigs, goats and horses), and birds (e.g., domestic, wild and game birds such as chickens, turkeys and other gallinaceous birds, ducks, geese, and the like). In some implementations, the subject may be a mammal, preferably a canine or a human.

The term "extraction" as used herein refers to any method for separating or isolating the nucleic acids from a sample, more particularly from a biological sample, such as blood or plasma. Nucleic acids such as RNA or DNA may be released, for example, by cell lysis. Moreover, in some aspects, extraction may also encompass the separation or isolation of extracellular RNAs (e.g., extracellular miRNAs) from one or more extracellular structures, such as exosomes. Some embodiments of the invention include the extraction of one or more forms of nucleic acids from one or more samples. In some aspects, the extraction of the nucleic acids can be provided using one or more techniques known in the art. In other embodiments, methodologies of the invention can use any other conventional methodology and/or product intended for the isolation of intracellular and/or extracellular nucleic acids (e.g., DNA or RNA).

The term "nucleic acid" as referred to herein comprises all forms of RNA (mRNA, miRNA, lRNA, tRNA, piRNA, ncRNA), DNA (genomic DNA, mtDNA, cfDNA, ctDNA, cDNA), as well as recombinant RNA and DNA molecules or analogs of DNA or RNA generated using nucleotide analogues. The nucleic acids may be single-stranded or double-stranded. The nucleic acids may include the coding or non-coding strands. The term also comprises fragments of nucleic acids, such as naturally occurring RNA or DNA which may be recovered using one or more extraction methods disclosed herein. "Fragment" as referred to herein comprises a portion of nucleic acid (e.g., RNA or DNA).

An "allele" includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frame shift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, under-expression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

The term "housekeeping genes" as used herein is meant to refer to genes that encode protein products that are not connected to, involved in or required for processes specific to a disease state (e.g., cancer) in cells, and thus, exhibit a fixed expression level in diseased and healthy cells.

Generally, some embodiments of the invention may include assessing, determining, quantifying, or altering the expression of one or more markers. Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, droplet digital PCR, ampicon sequencing, reverse transcriptase treatment followed by direct sequencing, or any other method of detecting a specific nucleic acid now known or yet to be disclosed.

Some embodiments of the present invention can be used to identify, quantify, detect, assess, isolate, and/or augment expression levels of one or more markers. A marker may be any molecular structure produced by a cell, expressed inside the cell, accessible on the cell surface, or secreted by the cell. Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

As used herein, "primer/probe set" refers to a grouping of a pair of oligonucleotide primers and an oligonucleotide probe that hybridize to a specific nucleotide sequence. Said oligonucleotide set consists of: (a) a forward discriminatory primer that hybridizes to a first location of a nucleic acid sequence; (b) a reverse discriminatory primer that hybridizes to a second location of the nucleic acid sequence downstream of the first location and (c) a fluorescent probe labeled with a fluorophore and a quencher, which hybridizes to a location of the nucleic acid sequence between the primers. In other words, a primer/probe set consists of a set of specific PCR primers capable of initiating synthesis of an amplicon specific to a nucleic acid sequence, and a fluorescent probe which hybridizes to the amplicon.

An "amplicon" refers to a nucleic acid fragment formed as a product of natural or artificial amplification events or techniques. For example, an amplicon can be produced by PCR, ligase chain reaction, or gene duplication.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays. For example, as described in greater detail herein, in some aspects of the invention, a first reagent and a second reagent can be used to detect HER2 mutations, such as HER2 V659. In some embodiments, the first and/or the second reagents may comprise one or more oligonucleotides (e.g., primers) that can specifically bind to DNA, RNA, and/or cDNA to detect the presence and/or expression of nucleic acids that correspond to HER2 V659 (SEQ ID NOS: 1 and 2).

As used herein, "digital PCR" refers to an assay that provides an end-point measurement that provides the ability to quantify nucleic acids without the use of standard curves, as is used in real-time PCR. In a typical digital PCR experiment, the sample is randomly distributed into discrete partitions, such that some contain no nucleic acid template and others contain one or more template copies. The partitions are amplified to the terminal plateau phase of PCR (or end-point) and then read to determine the fraction of positive partitions. If the partitions are of uniform volume, the number of target DNA molecules present may be calculated from the fraction of positive end-point reactions using Poisson statistics, according to the following equation (1):

$$\lambda = -\ln(1-p) \tag{1}$$

wherein $\lambda$ is the average number of target DNA molecules per replicate reaction and p is the fraction of positive end-point reactions. From 2, together with the volume of each replicate PCR and the total number of replicates analyzed, an estimate of the absolute target DNA concentration is calculated. Digital PCR includes a variety of formats, including droplet digital PCR, BEAMing (beads, emulsion, amplification, and magnetic), and microfluidic chips.

"Droplet digital PCR" (ddPCR) refers to a digital PCR assay that measures absolute quantities by counting nucleic acid molecules encapsulated in discrete, volumetrically defined, water-in-oil droplet partitions that support PCR amplification (Hinson et al., 2011, Anal. Chem. 83:8604-8610; Pinheiro et al., 2012, Anal. Chem. 84:1003-1011). A single ddPCR reaction may be comprised of at least 20,000 partitioned droplets per well.

A "droplet" or "water-in-oil droplet" refers to an individual partition of the droplet digital PCR assay. A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84:1003-1011).

Droplet digital PCR may be performed using any platform that performs a digital PCR assay that measures absolute quantities by counting nucleic acid molecules encapsulated in discrete, volumetrically defined, water-in-oil droplet partitions that support PCR amplification. The strategy for droplet digital PCR may be summarized as follows: a sample is diluted and partitioned into thousands to millions of separate reaction chambers (water-in-oil droplets) so that each contains one or no copies of the nucleic acid molecule of interest. The number of "positive" droplets detected, which contain the target amplicon (i.e., nucleic acid molecule of interest), versus the number of "negative" droplets, which do not contain the target amplicon (i.e., nucleic acid molecule of interest), may be used to determine the number of copies of the nucleic acid molecule of interest that were in the original sample. Examples of droplet digital PCR systems include the QX100™ Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000,000 to 10,000,000 picoliter-sized droplets.

The term "template" refers to nucleic acid originating from a sample that is analyzed for the presence of a marker of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

"Amplification" includes a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The present invention further provides kits to be used in assessing the expression of a marker in a subject to assess the risk of developing disease, diagnosing the subject as having a stage of the disease, or determining to which stage the disease has progressed. Kits include any combination of components that facilitates the performance of an assay. A kit that facilitates assessing the expression of the markers may include suitable nucleic acid-based and immunological reagents as well as suitable buffers, control reagents, and printed protocols.

Overall, some embodiments of the invention include systems and methods for the diagnosis of a condition, assessing the prognosis of the condition, and treating the condition. The one or more markers can be used to diagnose and/or assess the likely sensitivity of the cancer to a particular therapy or pharmaceutical composition. For example, the method of treatment may comprise determining an expression of a marker, such as a HER mutation, for example HER2 V659, to determine sensitivity of the cancer to an anti-HER agent, and subsequently administering to the patient the anti-HER agent, such as a tyrosine kinase inhibitor, for example neratinib, lapatinib, and erlotinib or a HER2 recombinant monoclonal antibody, for example trastuzumab.

Moreover, some embodiments of the invention may further provide treating a cancer, such as non-small cell lung cancer. Some embodiments of the invention may include the administration of one or more pharmaceutical compositions to a subject that has been diagnosed with cancer. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The following examples are given for purely illustrative and non-limiting purposes of the present invention.

Examples

We have discovered recurrent somatic HER2 (ERRB2) point mutations in 38% of canine pulmonary adenocarcinomas (cPAC) which confer both constitutive activation of proliferative signaling and also sensitivity to the HER2 inhibitors lapatinib and neratinib.

Through multi-platform sequencing of 90 primary canine lung tumors or cell lines, we discovered somatic, coding HER2 (ERRB2) point mutations in 38% of canine pulmonary adenocarcinomas (cPAC, 28 of 74), but none in adenosquamous (cPASC, 0 of 11) or squamous cell carcinomas (cPSCC, 0 of 3). In cPAC, recurrent somatic mutation of TP53, SMAD4, PTEN, and VHL were also identified. cPACs assessed by exome sequencing displayed a low mutation burden (median 64 SNVs, 19 CNVs and 1 SV). The majority (93%) of HER2 mutations are hotspot V659E transmembrane domain (TMD) mutations comparable to activating mutations at this same site in human cancer. Other HER2 mutations identified in this study were located in the extracellular and TMD. The HER2 V659E mutation was detected in the plasma of 33% (2 of 6) of dogs with localized tumors bearing this mutation. HER2 V659E correlated with constitutive phosphorylation of Akt in cPAC cell lines and HER2 V659E-mutant lines displayed hypersensitivity to the HER2 inhibitors lapatinib and neratinib relative to HER2 wild-type cell lines. These findings have immediate translational and comparative relevance for lung cancer and mutant HER2 inhibition.

Methods

Sample Collection: Tumors and cell lines from 89 dogs from the Canine Comparative Oncology and Genomics Consortium (CCOGC) (11) and The Ohio State University (OSU) College of Veterinary Medicine Biospecimen Repository were included. Board-certified veterinary pathologists confirmed tumor diagnosis based on histopathology. Tumor and normal tissue samples were flash frozen in liquid nitrogen or formalin-fixed and paraffin-embedded (FFPE). Cell lines were maintained in RPMI 1640 with GlutaMAX™ (Gibco™, Thermo Fisher Scientific, #61870036) supplemented with 10% heat-inactivated fetal bovine serum at 37° C. and 5% CO2 and passaged at 90% confluence. Cell lines with known passage data (except BACA) were sequenced within the first eight passages of derivation and subsequently expanded for phenotypic studies, and were authenticated by IDEXX BioResearch (Columbia, MO) using the Cell Check Canine STR Profile and Interspecies Contamination Test or by NkX2 (or TTF-1) RT-PCR. Human cell lines included BT474 (ATCC #HTB20, HER2 focal amplification) and H1781 (ATCC #CRL-5894, HER2 G776V). Blood for cell-free DNA (cfDNA) and germline DNA extraction was collected in 10 ml K2 EDTA Blood tubes (Thermo Fisher Scientific #22-253-145). Plasma separation was performed at room temperature within 1 hour (2× serial centrifugation at 2000 rpm×15 minutes). Plasma aliquots were stored frozen at −80° C. DNA extraction from plasma, white blood cells and tissue was performed with MagMAX Cell-Free DNA Isolation Kit (Thermo Fisher Scientific #A29319), DNeasy Blood and Tissue Kit (QIAGEN #69504) and Qiagen AllPrep DNA/RNA Mini Kit (QIAGEN #80204), respectively.

Exome Sequencing and Analysis: Informatic tools, versions, and flags are shown in FIGS. 7A-7C. We utilized a custom Agilent SureSelect canine exome capture kit with 982,789 probes covering 19,459 genes. Exome libraries were sequenced on the Illumina HiSeq2000 producing paired end reads of 85 bp. FASTQ files were aligned to the canine genome (CanFam3.1) using BWA v0.7.8. Aligned BAM files were realigned and recalibrated using GATK v3.3.0 and duplicate pairs were marked with Picard v1.128. Somatic copy number variants (CNVs), and structural variants (SVs) were called with tCoNutT and DELLY v0.76. Somatic single nucleotide variants (SNV) were identified from two or more of the following callers: Seurat v2.6, Strelka v1.0.13 and MuTect v1.1.4. Germline SNVs were called using Haplotype Caller (GATK v3.3.0) and Freebayes. Variant annotation was performed with SnpEff v3.5. The SomaticSignatures R package was used to identify mutation signatures.

Targeted Amplicon Sequencing and Analysis: The present disclosure, and method used herein, includes a custom-developed canine cancer amplicon sequencing panel consisting of 281 amplicons targeting exons and hotspot regions in 57 genes. Using this panel, the amplification was performed independently in each drop and resulted in amplicon sizes ranging from 91 to 271 base pair (bp) (FIGS. 13A-13G). Primers were pooled in two multiplexed pools to separate adjacent amplicons and any amplicons that showed cross-amplification using in silico PCR. Sequencing libraries were prepared using digital PCR amplification following the manufacturer's protocols for the ThunderBolts Cancer Panel (RainDance Technologies) with modifications (52). Sequencing of the amplicons was performed on the Illumina MiSeq generating paired-end 275 bp reads. Sequencing reads were demultiplexed and extracted using Picardtools. Sequencing adapters were trimmed using ea-utils and fastq files were assessed for quality using FASTQC. Sequencing reads were aligned to CanFam3.1 using BWA-mem and converted to BAM using Samtools (53). Scripts were developed based on Samtools and were used to create pileups for every sample with attached amplicon IDs. The pileups were analyzed in R to call SNVs and indels (insertions/deletions). For each potential non-reference allele at each targeted locus in a sample, we evaluated the distribution of background noise across all other sequenced samples. Variants were filtered based on stringent cutoffs to enable calling high-confidence somatic variants. To call a variant, we required the observed non-reference allele is an outlier from the background distribution with a Z-score>5. The variant filters included tumor depth ($\geq 100\times$), allele frequency ($\geq 10\%$), number of reads supporting the variation ($\geq 10$), and germline background (<0.01) or allele fraction in the germline sample (<1%). Variants were manually curated by visualization in IGV v2.3.71.

Sanger Sequencing: Twenty-three primer pairs covering all exons of HER2 were designed using Primer 3 including a universal M13 tag. Amplicons were Sanger sequenced at the DNASU sequencing facility at Arizona State University on an ABI 3730XL (Applied Biosystems, Foster City, CA) and analyzed with Mutation Surveyor DNA Variant Analysis Software (SoftGenetics, State College, PA).

HER2 Inhibitor Drug Dose-response Studies: HER2 inhibitors lapatinib (Selleckchem, #S2111), neratinib (Puma Biotechnology, Los Angeles, CA), and trastuzumab (Selleckchem, #A2007), as well as the EGFR inhibitor erlotinib (Selleckchem, #S1023) were assessed in 10-16 point 72 hour drug-dose response screens (from 2×10−7 nM to 100 µM) with CellTiter-Glo® luminescent cell viability assay (Promega, #G7570) endpoints. Cells were cultured in RPMI supplemented with 10% FBS and 1% Penicillin/Streptomycin. Luminescence was read using Synergy Mx (Biotek) plate reader. Six replicates were performed for each dose.

Curve-fitting and $IC_{50}$ calculations were performed using GraphPad Prism v7.00 (GraphPad Software).

Droplet Digital PCR: HER2 V659E genotyping was performed on tumor samples and plasma cell-free DNA with droplet digital PCR (ddPCR). 50 microliter (µl) reactions contained 2×KAPA PROBE FAST Master Mix (Kapa Biosystems, #KK4701), 200 µM dNTP Mix (New England BioLabs Inc, #N0477S), 1× Droplet Stabilizer (RainDance Technologies, #30-00826), 1 µM pooled primer mix (IDT), 1 µM mutant (FAM labeled) or wild type (TET labeled) HER2 V659E probe (IDT), and 21.75 µL of template DNA. Each reaction was partitioned into 10,000,000 droplets using the RainDrop Digital PCR Source (RainDance). PCR amplification was performed as follows: 1 cycle 3 min at 95° C., 50 cycles 15 sec at 95° C. and 1 min at 60° C. with a 0.5° C./sec ramping from 95° C. to 60° C., 1 cycle 98° C. for 10 min and hold at 4° C. Droplet fluorescence was measured using RainDrop Digital PCR Sense and analyzed using accompanying RainDrop Analyst II Software v.1.0 (RainDance).

The primer and probe sequences used for HER2 V659 detection in ctDNA were forward primer: 5'-CCCACGAC-CACAGCCA-3' (SEQ ID NO: 1), reverse primer: 5'-CCCTGTGACATCCATCATTGC-3' (SEQ ID NO: 2) and probe: 5'-CAGAATGCCC(T/A)CCACAGC-3' (SEQ ID NO: 3).

TABLE 1 shows an assay for the detection of HER2 V659, including primer and probe sequences.

TABLE 1

| | Seq Type | Sequence | SEQ ID NO |
|---|---|---|---|
| HER2 V659 detection in ctDNA | Forward Primer | CCCACGACCACAGCCA | 1 |
| HER2 V659 detection in ctDNA | Reverse Primer | CCCTGTGACATCCATCATTGC | 2 |
| HER2 V659 detection in ctDNA | Probe | CAGAATGCCC(W)CCACAGC W = A/T Alternatively written as: CAGAATGCCC(T/A)CCACAGC | 3 | qRT-PCR: cDNA was obtained by reverse transcription with iScript (Biorad, #1708891) and samples were subjected to HER2 (target) and HPRT1 (reference) amplification in a QuantStudio™ 6 Flex Real-Time PCR System under standard conditions with Syber Green technology (KapaBiosystems, #KK4602).

Primer sequences were: HER2-Forward: 5'-CATCTGCACCATTGATGTCTA-3' (SEQ ID NO: 4), HER2-Reverse: 5'-GGCCCAAGTCTTCATTCTGA-3' (SEQ ID NO: 5), HPRT1-Forward: 5'-GCAGCCCCAGCGTCGTGATT-3' (SEQ ID NO: 6), HPRT1-Reverse: 5'-CATCTCGAGCAAGCCGCTCAGT-3' (SEQ ID NO: 7).

Data was analyzed with Quantstudio Real Time PCR software v1.1. Values for ΔCt, ΔΔCt, and fold changes were calculated as follows: ΔCt=Ct HER2-Ct HPRT1; ΔΔCt=ΔCt tumor sample-ΔCt average of normal samples; and fold change=2^(-ΔΔCt).

TABLE 2 shows an assay for amplification of the HER2 target, including the primer sequences used for qRT-PCR.

TABLE 2

| | Seq Type | Sequence | SEQ ID NO |
|---|---|---|---|
| HER2-Forward | Forward Primer | CATCTGCACCATTGAT GTCTA | 4 |
| HER2-Reverse | Reverse Primer | GGCCCAAGTCTTCATT CTGA | 5 |
| HPRT1-Forward | Forward Primer | GCAGCCCCAGCGTCG TGATT | 6 |
| HPRT1-Reverse | Reverse Primer | CATCTCGAGCAAGCC GCTCAGT | 7 |

Immunohistochemistry: HER2 protein expression was evaluated on FFPE sections (4 µm) of normal lung and tumor mounted on SuperFrost™ Plus glass slides (Fisher Scientific #12-550-15). Slides were deparaffinized in xylene and rehydrated in an ethanol gradient. Antigen retrieval was performed with 1 mM EDTA adjusted to pH 9.0. An autostainer (Dako, model S3400) was used to carry out immunostaining. A HER2 rabbit monoclonal antibody (Cell Signaling Technology, #4290) was used at 1:400 dilution followed by secondary biotinylated rabbit anti-goat IgG (Vector Laboratories, BA-1000) diluted 1:200. Detection was performed with VECTASTAIN® Elite® ABC System (#PK-6100). IHC positive controls for HER2 tyrosine kinase receptor expression were single tissue samples of two canine complex mammary carcinomas (54). Negative controls were performed on all tissues using a universal rabbit negative isotype control not directed against any known antigen (Dako, #IR600).

Quantitative Image Analysis: Immunostained and control 1×3-inch microscope slides were scanned at 40× on a high-resolution Scanscope XT (Leica Biosystems). For quantification of immunoreactivity, images were imported into Visiopharm Image Analysis software (Visiopharm, Hørsholm, Denmark version 2017.27.0.3313), segmented into areas of tumor, necrosis, and normal lung tissue using color labels for each tissue type. HER2 connectivity was scored using the modified 10007-HER2, Breast Cancer APP (Visiopharm). Thresholds were adjusted to match specimen HER2 stain intensities for accurate scoring. Area (µm2) was quantified for each tissue type and percentages derived from specimen total tissue area. Tumor areas were further segmented into staining and non-staining categories and their percentages were calculated based on total tumor area in µm2. Maximum, mean, and minimum intensities were also quantified using a built-in software calculation. Staining is expressed as percentage of stain present with 100% equal to black (maximum dark brown) and 0% equal to white (no stain present). Initial thresholds and tissue types were established and mark-ups reviewed in consultation with a pathologist board-certified by the ACVP to ensure accurate measurements and to differentiate between tissue types.

Immunoblot Analyses: Subconfluent cells were serum starved overnight, then treated with 20 nM neuregulin for 15 min prior to harvest. Cells were lysed in RIPA buffer with cOmplete™ Mini Protease Inhibitor (Roche, #11836153001) and PhosSTOP™ (Roche, #4906845001) and loaded in Laemmli buffer at 1 µg/µl. Samples were separated on 4-15% SDS-PAGE Criterion Gels (BioRad, #5671085) and transferred to Immobilon-FL PVDF membrane (MilliporeSigma, #IEVH7850). Membranes were blocked for 1 hour in LiCor blocking buffer and incubated with primary antibody at 4° C., overnight, followed by fluorescence-conjugated secondary antibodies. Membranes were scanned using the LiCor Odyssey CLx instrument. Primary antibodies were AKT (CST #4691S, 1:1000), phospho-AKT (CST #4060P, 1:1000), and β-actin (CST #4970S, 1:1000).

Results and Discussion

The results herein describe the genomic landscape of naturally occurring primary canine lung cancer. In order to map the genomic landscape of canine lung cancer, we undertook multi-platform next-generation sequencing of 88 NSCLC cases including 77 tumor/normal matched pairs and 11 cell lines (TABLE 3). The cohort included 74 cPAC (Canine Pulmonary Adenocarcinoma) samples, 11 cPASC (Canine Pulmonary Adensquamous Carcinoma) samples, and 3 cSCC (Canine Squamous Cell Carcinoma) samples. Labrador Retrievers represented the most commonly affected pure breed dog (21%) with mixed breeds (25%) and multiple other single pure breeds. The predominant cPAC subtype was papillary adenocarcinoma (62%). The cohort was gender-balanced (52% females) and primarily neutered/spayed (92%) with a median age at diagnosis of 11 years. Smoking status in the pet's household was not available. Extended clinical annotation is shown in FIGS. 3A-3F and FIGS. 8A-8J.

TABLE 3

Genomic analyses performed in primary canine lung cancer

| Analysis Platform | Samples analyzed* | Type of alteration detected |
|---|---|---|
| Exome | 5 cPAC and matching normal | Germline and somatic SNVs, CNVs, and SVs in coding regions |
| Amplicon | 61 cPAC and matching normal**, 8 cell lines | Germline and somatic SNVs in 53 cancer genes |
| Amplicon | 10 cPASC and matching normal, 1 cell line | Germline and somatic SNVs in 53 cancer genes |
| Amplicon | 2 cSCC and matching normal, 1 cell line | Germline and somatic SNVs in 53 cancer genes |

*an additional cell line (OSUK9PADRi) was analyzed by Sanger sequencing
**all matching normal samples were available except one (CCB30381).

In order to identify somatic point mutations, copy number changes, and translocations we first sequenced the coding genomic regions of five cPAC tumors and matching normal samples using a custom Agilent SureSelect canine exome capture kit comprising 982,789 probes covering 19,459 genes. Tumors were exome sequenced with a mean target coverage of 298X, and matching normal samples were exome sequenced with a mean target coverage of 263X, each with 99% of target bases covered ≥40× (TABLE 4). TABLE 4 shows a table of sequencing metrics for primary canine lung cancer exome analysis, where the metrics were obtained using picardtools.

TABLE 4

Sequencing metrics for primary canine lung cancer exome analysis.

| Metrics | Normal | Tumor |
|---|---|---|
| Total number of reads | 1,074,194,664 | 1,185,003,340 |
| Average number of reads (range) | 214,838,933 (162,303,724-255,845,742) | 237,000,668 (217,580,754-245,842,622) |
| % of passing filter (PF) reads | 100% | 100% |
| Mean % of PF reads aligned (range) | 99.79% (99.78-99.80%) | 99.18% (96.68-99.815) |
| Mean target coverage (range) | 263.5 (204.11-313.46) | 298.79 (274.02-311.19) |
| % of bases at 40X | 98.54 (97.92-98.97%) | 98.66% (98.23-98.84%) |

Figure 9:
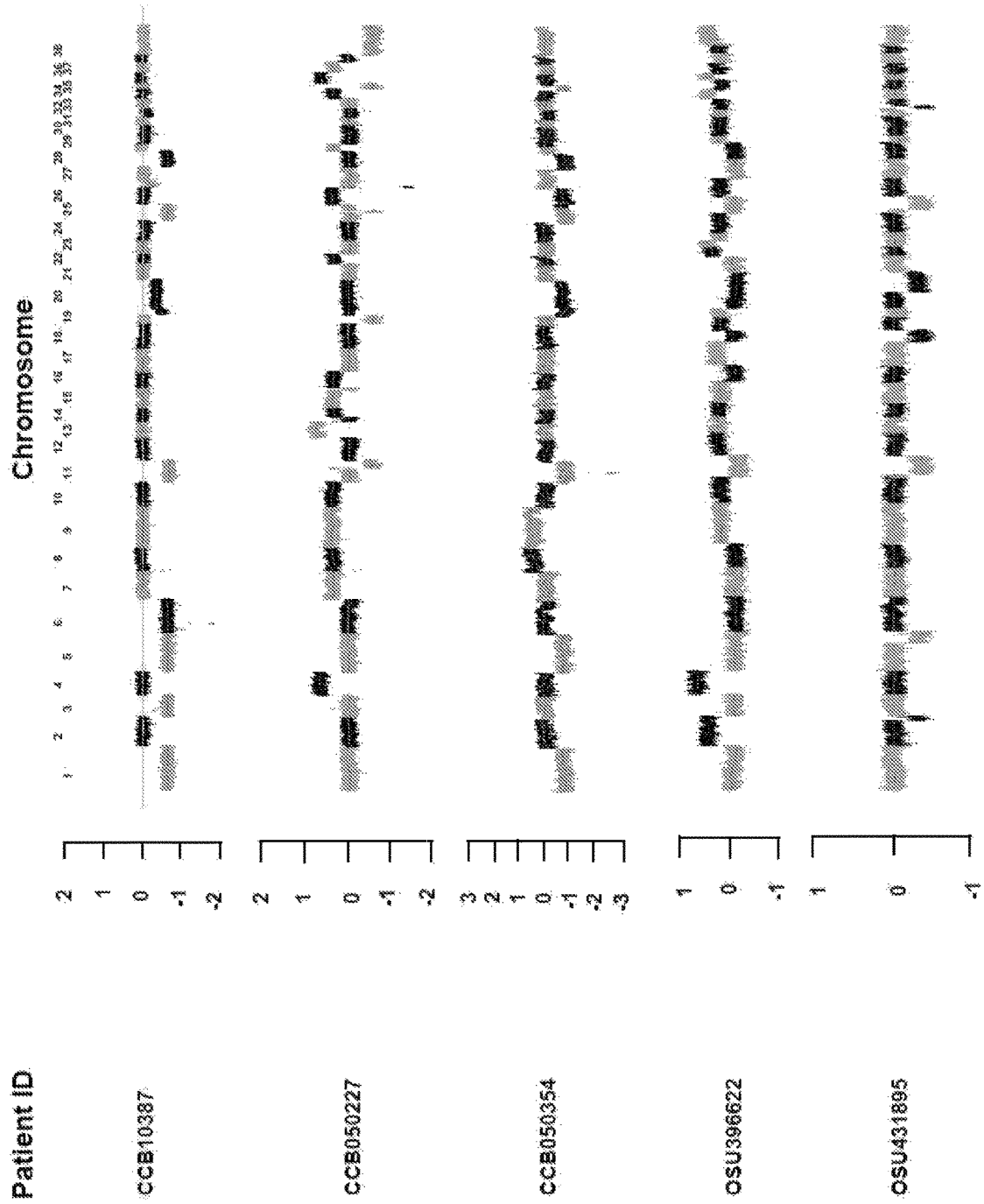
FIG. 9 illustrates somatic copy number plots derived from exome sequencing of five primary canine pulmonary adenocarcinomas (cPAC) and matched constitutional DNA; tumor copy number states determined by tCoNutT analysis of tumors and matched constitutional DNA from five cPAC cases is shown with each canine chromosome plotted on the x-axis (shown in alternating green and black) and log 2 fold change shown on the y-axis.

A total of 648 high confidence somatic SNVs (median 64, range 37-406), 165 focal copy number variants (CNVs) (median 19, range 0-116), and 3 structural variants (SVs) (median 1, range 0-1) were identified (FIGS. 1A-1C, 10A-10H, 11A-11L, and 12). The average tumor mutation burden (TMB) for somatic point mutations per haploid callable megabase (Mb) in these cases was 2.04 mutations/Mb (range 0.58-6.38). Among these somatic variants, we identified mutations in genes whose human orthologs have been implicated in human cancer according to COSMIC (11) Tiers 1 and 2 including somatic SNVs (FIGS. 10A-10H), focal CNVs (FIG. 1B and FIGS. 11A-11L), SVs and numerical chromosomal changes (whole chromosome or arm-level gains/losses) (FIG. 9). The sole gene bearing recurrent nonsynonymous SNVs was HER2 (80%) with the missense mutation V659E occurring in three cases and the missense mutation K676E in a fourth case (FIG. 1D). No HER2 amplifications were detected in these five tumors.

Figure 4A:
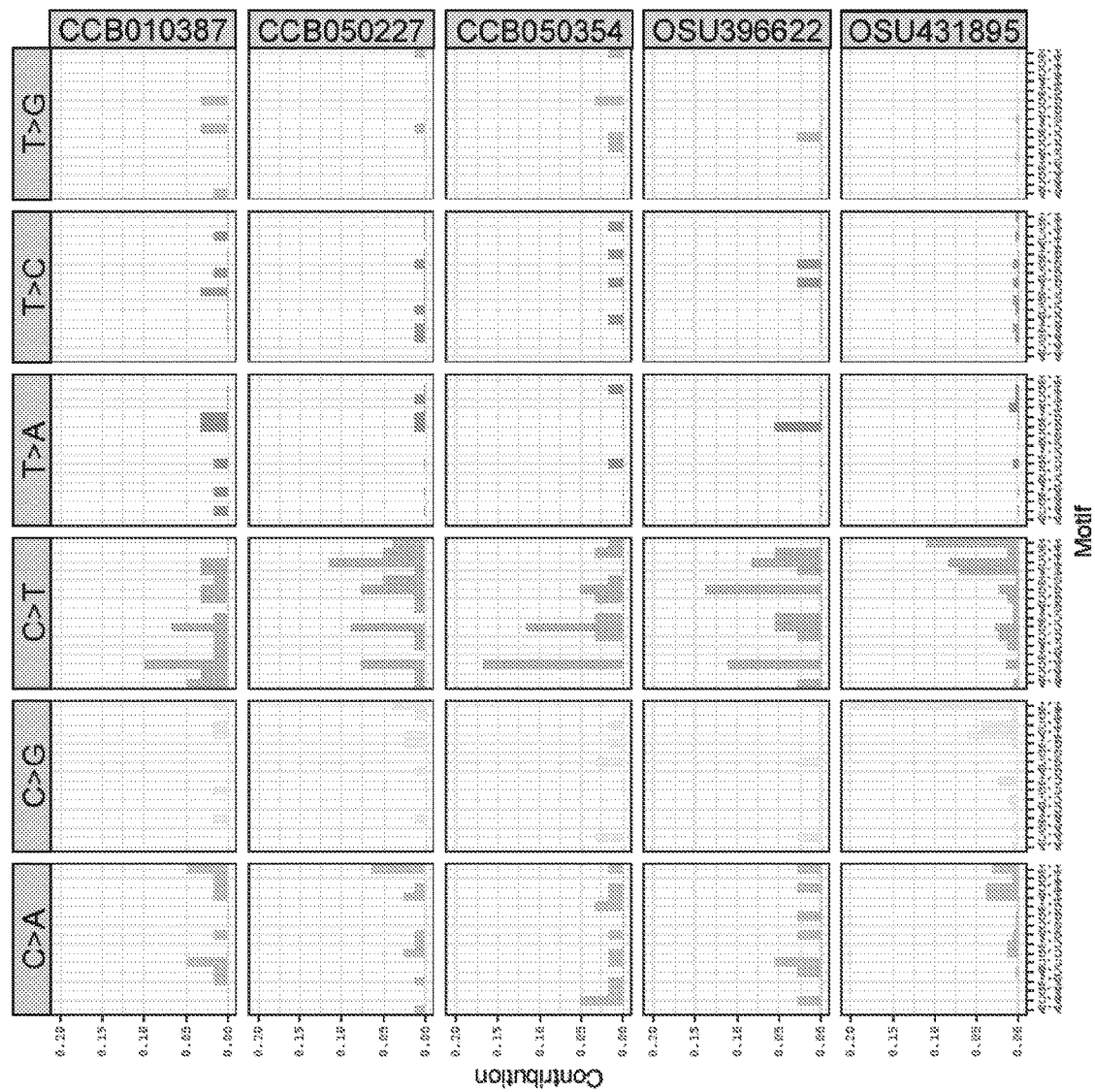
FIGS. 4A and 4B illustrate mutation signatures identified by exome sequencing in primary canine lung cancers.
Figure 4B:
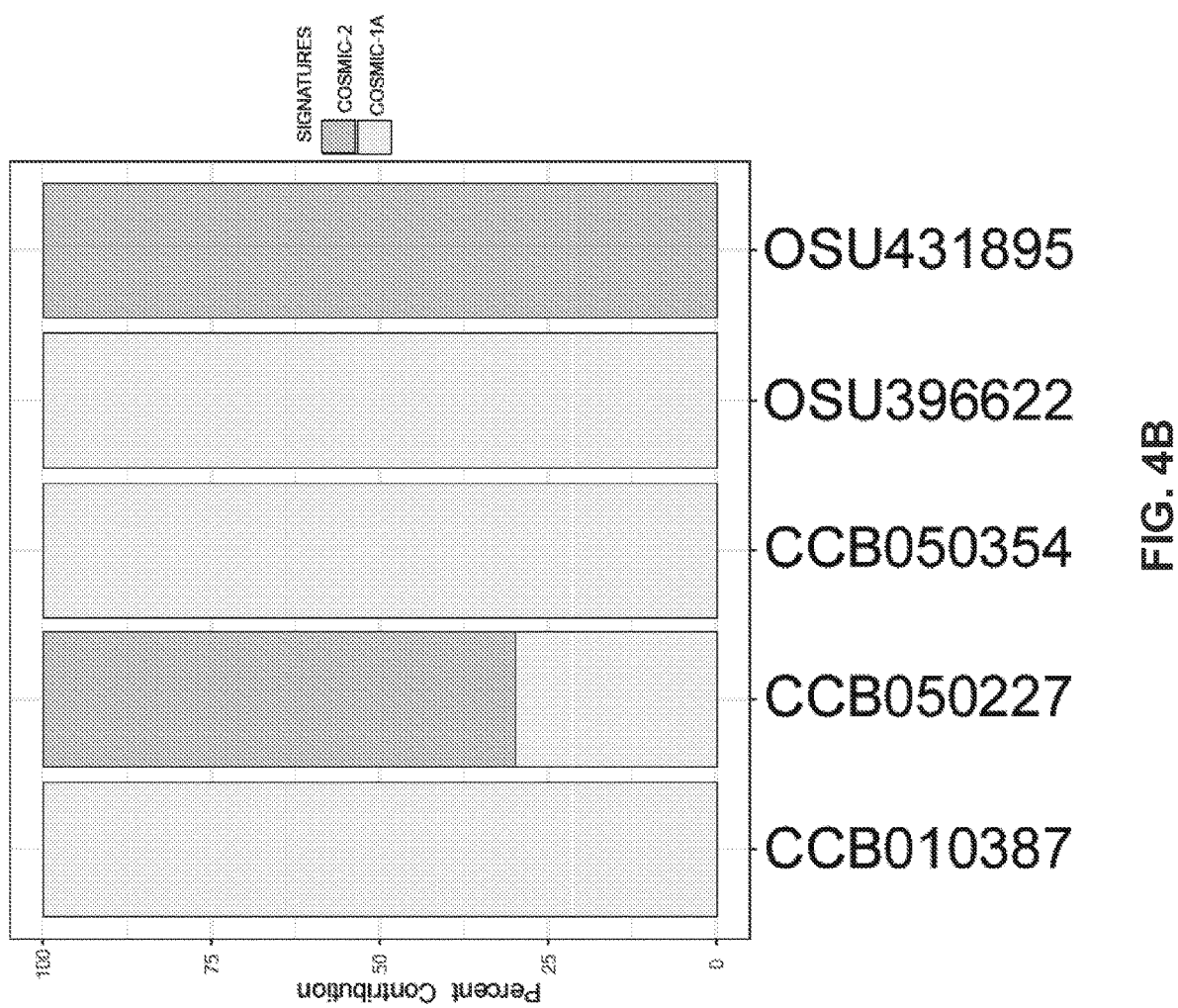
Figure 5A:
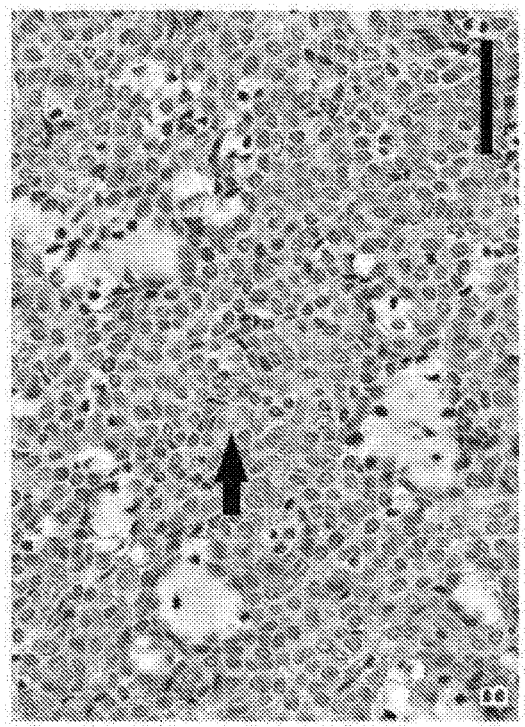
FIGS. 5A-5D illustrate the characterization of HER2 cellular location and function in primary canine lung cancer.
Figure 5B:
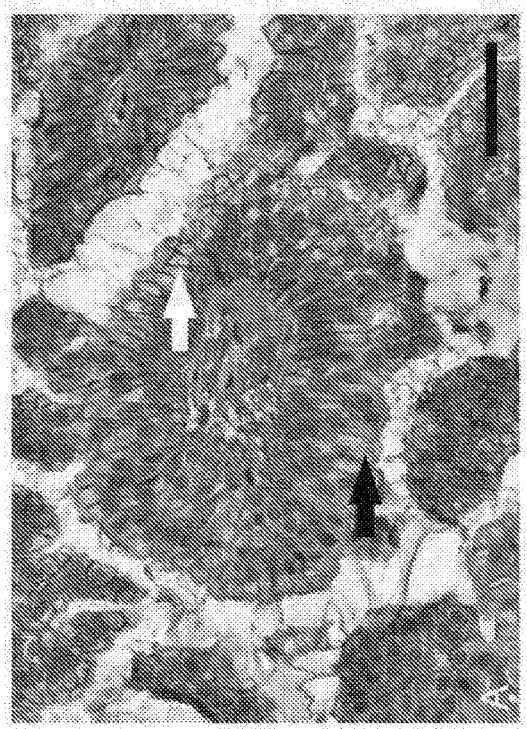
Figure 5C:
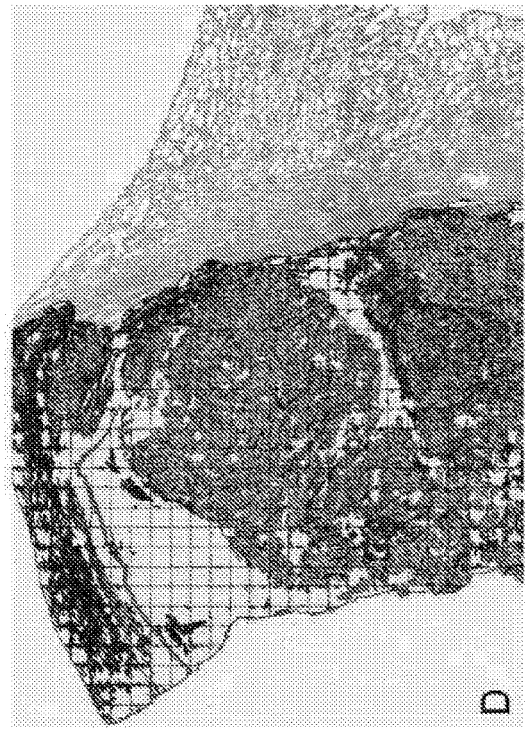
Figure 5D:
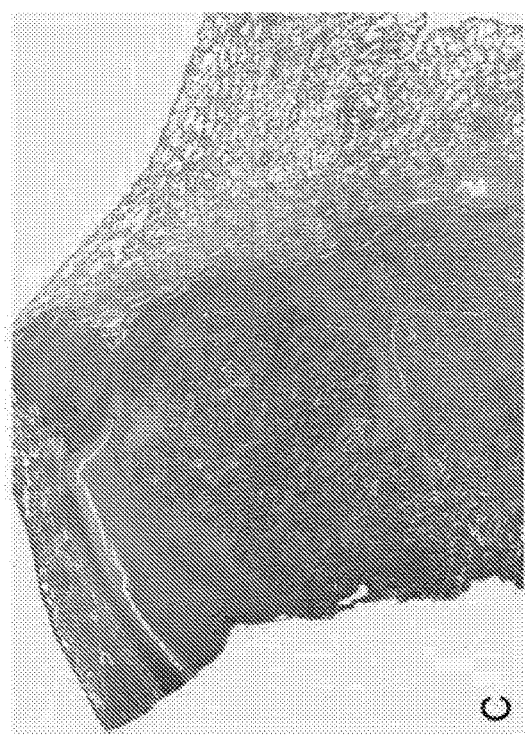

FIGS. 4A and 4B show the assessed somatic point mutation signatures according to their trinucleotide context (12, 13). The most common signature in these five cases was the age-associated COSMIC Signature 1A in 4 of 5 cases (80%). FIG. 4B shows COSMIC Signature 1A (C>T substitutions at NpCpG trinucleotides that are associated with age) was present in four cases. COSMIC Signature 2, C>T and C>G substitutions at TpCpN, associated with APOBEC cytidine deaminase activity was present in two cases, CCB050227 and OSU431895.

To identify somatic point mutations across a broader cohort of canine lung cancers, we used a custom canine cancer amplicon-based next generation sequencing panel (FIGS. 13A-13G) in 73 additional lung tumors (61 cPAC, 10 cPASC, 2 cPSCC), two previously exome-sequenced tumors with matched normal tissue, and 10 cell lines (8 cPAC, 1 cPASC, and 1 cPSCC). These cases were sequenced to an average depth of 3,383× (TABLE 5).

TABLE 5

Sequencing metrics for primary canine lung cancer amplicon analysis

| Metrics | |
|---|---|
| Number of amplicons | 281 |
| Number of genes | 53 |
| Number of amplicons passing threshold | 264 |

TABLE 5-continued

Sequencing metrics for primary canine lung cancer amplicon analysis

| Metrics | |
|---|---|
| Median sample depth (range) | 158 (64-19640) |
| Median amplicon depth (range) | 1989 (1-9466) |

A median of 1 somatic coding point mutation (range 0-3) within sequenced panel regions was identified across all cases. Likely pathogenic recurrent point mutations included HER2 V659E (29.8%), KRAS G12D/V (3.4%), SMAD4 D351Y/G (3.4%) and TP 53 R239Q/G (2.2%) (FIGS. 14A and 14B). Two additional somatic missense mutations in HER2 were identified in single cases, including A664T and K676E (FIG. 1D). Overall, recurrently mutated genes containing somatic potentially pathogenic SNVs included TP 53 (12.5%), PTEN (5.7%), SMAD4 (4.5%), KRAS (4.5%), VHL (3.4%) and HRAS (2.3%).

Based on both exome and amplicon sequencing, we evaluated germline SNPs to identify putatively pathogenic rare variants (i.e. those not previously identified in dogs based on review of presence in dbSNP 151 (14) and/or ≥10% frequency in DogSD (15) in 81 genes potentially associated with susceptibility to human lung cancer (16). We identified nine rare putatively pathogenic SNPs in five dogs in the genes CHRNA3, CYP1B1, DNAH11 and HER2 (FIG. 15). Of these SNPs, the only variant with an equivalent in its human orthologous gene was DNAH11 R1460W corresponding to human DNAH11 R1444W (rs1035326227, MAF<0.01%). The human SNP has not been associated with disease. HER2 V1189I variants occurred in two cases without somatic HER2 tumor mutations. The human orthologous position, V1184, has not shown human variation. The canine variant has been identified in 4% of cases in DogSD and based on functional effect prediction (FATHMM), it is likely neutral. None of the genes bearing rare SNPs showed second hits in tumor tissue.

Figures 1D, 1E:
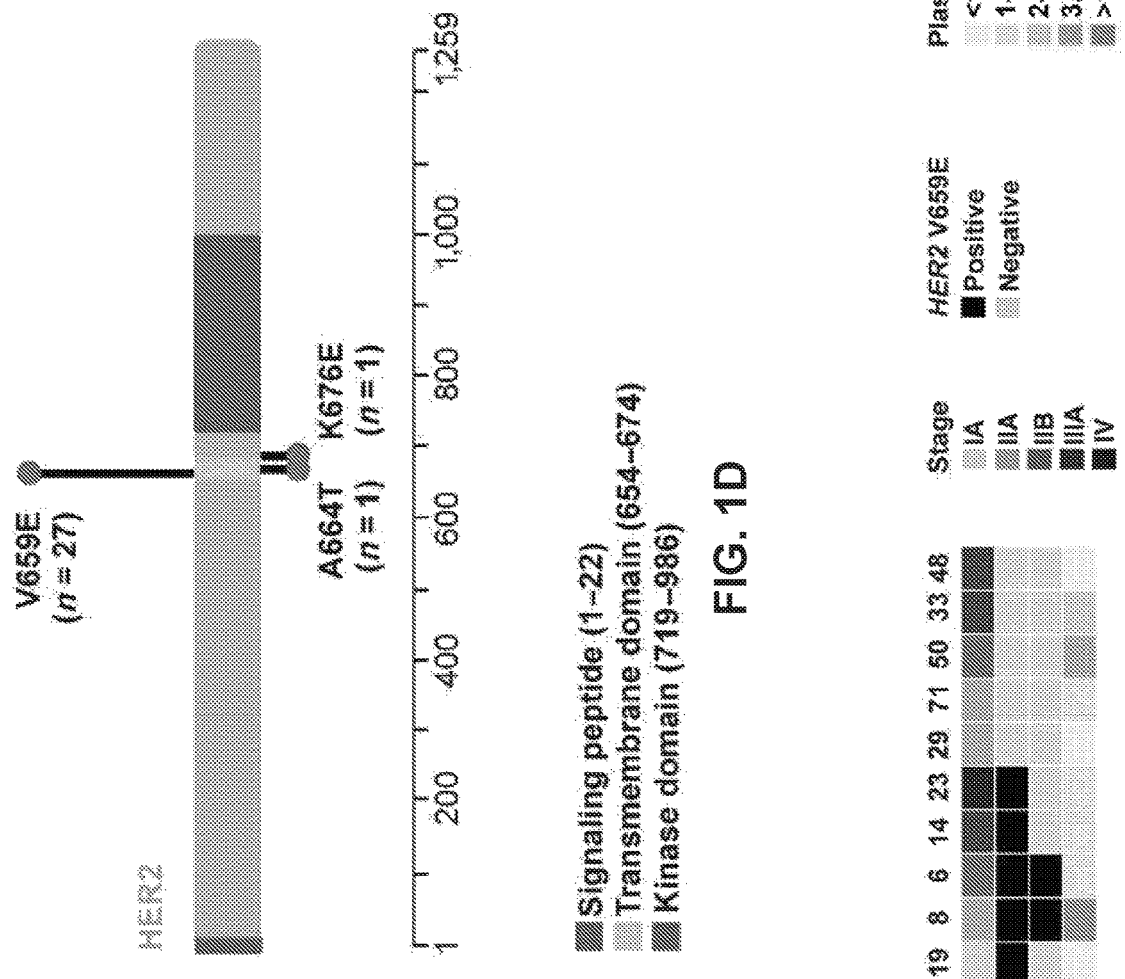

We additionally performed matched tumor/normal amplicon sequencing to evaluate the genomic landscapes of 11 cPASC and 3 cPSCCs, subtypes which are under-studied entities in dogs and humans, especially in never-smokers (FIG. 1A and FIGS. 14A-14B). In contrast with cPAC, no HER2 mutations were identified in these tumors. In cPASC, HRAS Q61L and KRAS Q61K each occurred in one case. Thus 18% of cases bore RAS hotspot mutations. PTEN stop gains additionally occurred in 2 of 11 (18%) cases at high tumor allele frequencies and were exclusive with RAS mutations. Additional likely pathogenic somatic mutations also occurred in a single cancer gene in a single tumor each including EGFR A726T, MET M1269V, TP53 R147C, and VHL P97L. Finally, while no recurrent mutations were identified in the three cPSCCs, we identified one case with a somatic BRAF V588E and another bearing PTPN11 G503V.

The results herein describe that HER2 is frequently mutated in canine pulmonary adenocarcinoma (cPAC).

HER2 was the most frequently mutated gene in our multi-platform next generation sequencing cohort, with missense mutations occurring exclusively in cPACs (27/74, 36.5%, two mutations occurring in a single patient) (FIG. 1A). No HER2 insertions were identified. We additionally identified a HER2 mutation in the cell line OSUK9PAPADRi solely by Sanger sequencing of the codon 659 locus. We thus identified 29 total HER2 mutations overall (FIG. 1D). In 24 cases, the HER2 variants were evaluated on at least two platforms including exome sequencing, amplicon sequencing, Sanger sequencing, and/or droplet digital PCR (ddPCR) (FIGS. 16A-16C). The HER2 variant tumor allele fraction (AF) median by amplicon sequencing was 21.3% (range 8.4-51.9%). All low allele fraction (<20%) cases identified by amplicon sequencing were also validated by Sanger and/or ddPCR. Notably, one cell line, OSUK9PAPADO, contained a low AF HER2 V659E variant (AFs of 15% by amplicon and 16% by ddPCR) during early short-term culture (passage 4) that was no longer detectable by Sanger sequencing or ddPCR in later passages (passage 15). Importantly, passage 15 was utilized for all functional studies described below and it was thus considered HER2 WT in this setting. Overall, V659E missense mutations located in the HER2 TMD occurred in 93.3% of HER2-mutant cases. Additional HER2 mutations included A664T (OSU419040) and K676E (CCB050354), which have not been previously described in orthologous human HER2 regions. In some cases, HER2 mutations co-occurred with mutations in TP53, SMAD4, PTEN, VHL, AKT1 or KDR.

The results herein describe that HER2 mutations are detectable in canine plasma.

Figure 19:
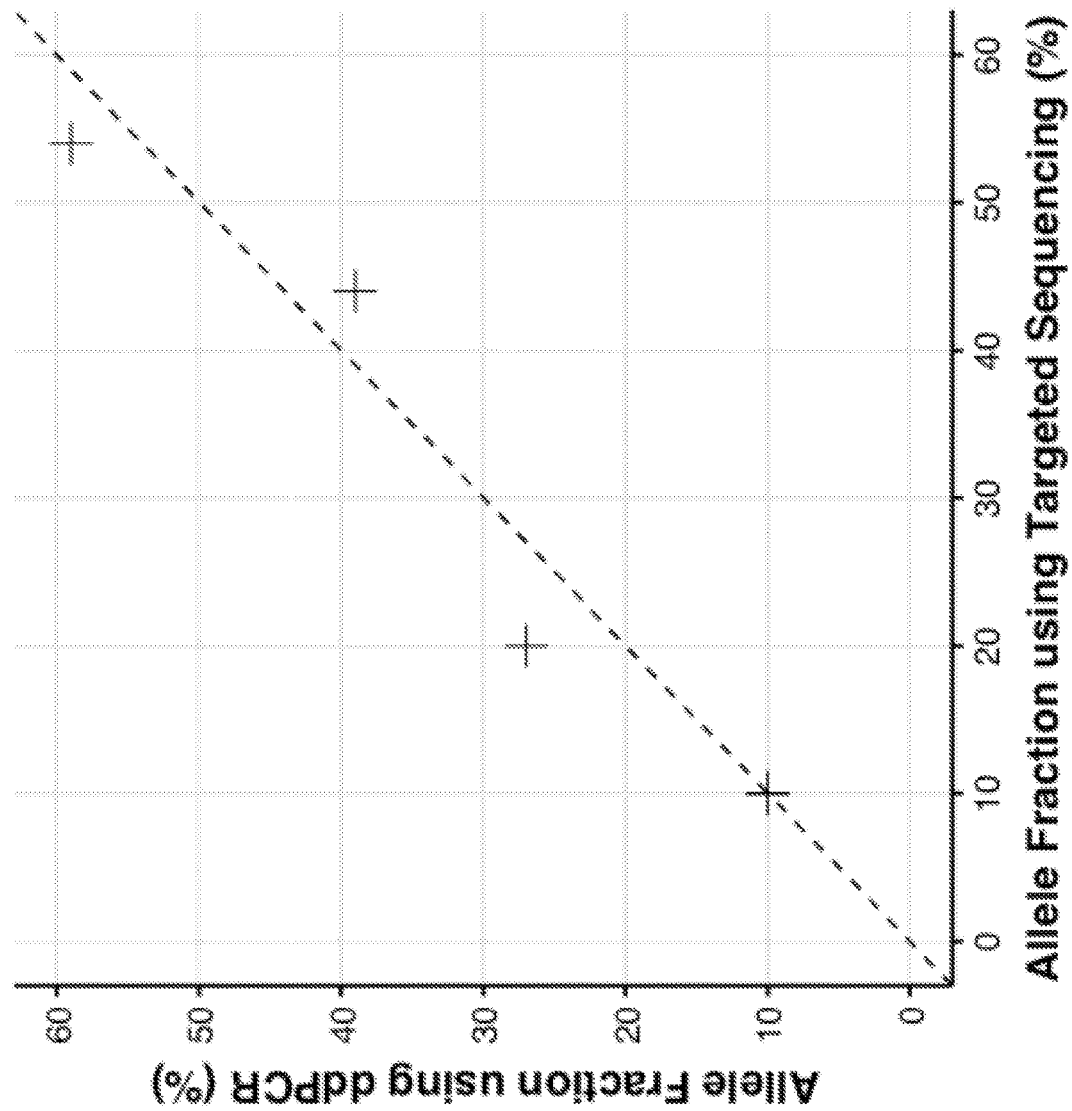
FIG. 19 illustrates a comparison of HER2 mutant allele fractions measured using droplet digital PCR and targeted sequencing in tumor tissue; HER2 V659E was evaluated by ddPCR in tumor DNA samples in which these mutations were also detected using amplicon sequencing; a high correlation was observed between allele fractions measured using both techniques (Pearson's r 0.976, p=0.0008)

Cell-free tumor DNA (ctDNA) in plasma has been increasingly used for noninvasive genotyping in human cancer patients (17). To develop a canine blood test that could rapidly identify dogs with HER2-mutant lung cancer, we investigated whether cPAC HER2 hotspot mutations are detectable in ctDNA. We evaluated plasma from 11 dogs, 5 with HER2-wild-type tumors and 6 with HER2 V659E tumors using droplet digital PCR (ddPCR) (FIG. 17). In order to evaluate assay performance (specificity), we first analyzed wild-type tumor samples, plasma DNA from unrelated commercially available canine plasma samples and template-free controls to establish assay specificity (BioreclamationIVT #BGLPLEDTA-100-P-m). Using uniform gating for all experiments, we found 1 of 7 template-free samples showed 1 wild-type droplet and no samples showed any evidence of mutant DNA amplification. In wild-type tumor and plasma DNA samples, 2 of 8 samples showed 1 mutant droplet each. Based on these results, we required at least 3 mutant droplets to confidently detect HER2 V659E. To confirm mutation detection and quantitative performance, we analyzed and detected HER2 V659E in 6 of 6 positive control tumor DNA samples where we had previously identified V659E mutations using amplicon sequencing. In these samples, we observed a high correlation between allele fractions measured using amplicon sequencing and ddPCR (Pearson's r 0.976, p=0.0008) (FIG. 19). In 11 plasma samples from dogs with cPAC tested using ddPCR, median total cell-free DNA concentration was 3.7 ng/ml plasma (range 0.7-23.0) (FIG. 17). Requiring at least three mutant droplets to support mutation detection and testing cfDNA equivalent to 435 µL plasma, the median limit of detection (LoD) for mutation allele fraction was calculated at 0.61% (range 0.10%-3.11%). HER2 V659E mutations were detected in 2 of 6 plasma samples from dogs with HER2 V659E-positive tumors at 1.9% and 2.3% allele fractions. HER2 V659E was not detected in any plasma samples from dogs with HER2 WT tumors, confirming assay specificity (FIG. 1E). Sensitivity for mutation detection in this cohort may be limited due to low total cfDNA concentration and amounts analyzed.

The results herein describe HER2 expression in cPAC.

Figure 20B:
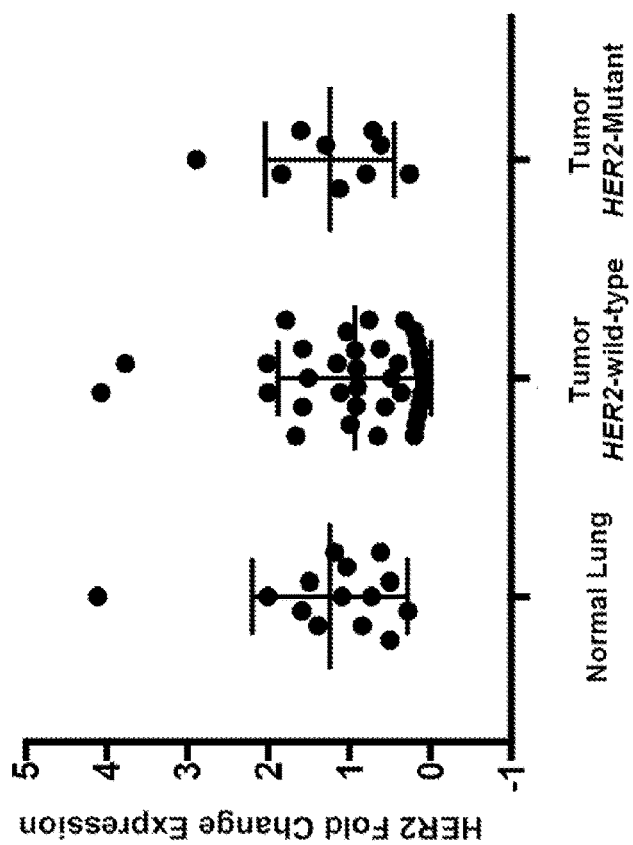
FIGS. 20A-20B illustrate HER2 expression in primary canine lung cancer based on quantitative real-time PCR analyses; box plots are shown for HER2 $2^{(-\Delta\Delta Ct)}$ expression fold-change relative to the housekeeping gene HPRT (x-axis) in 49 tumors and 14 matched normal lung tissues comparing.
Figure 20A:
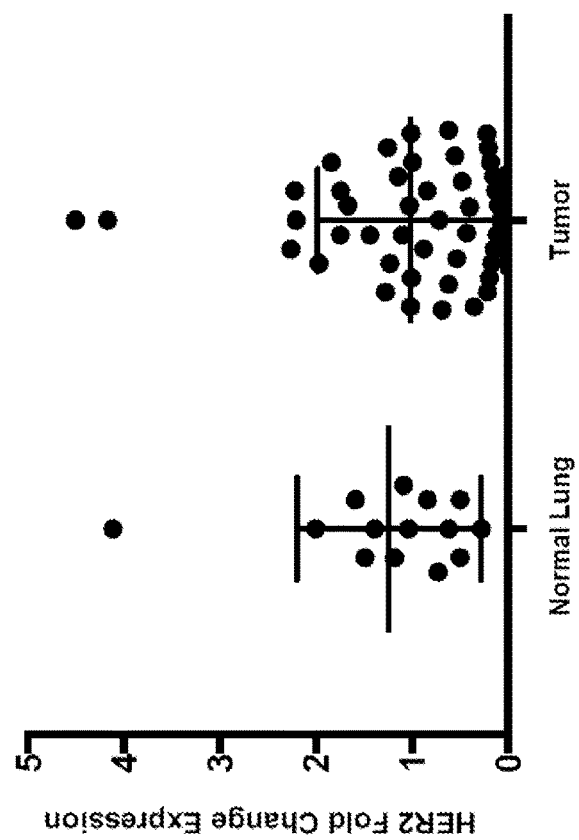

In human cancers, HER2 bears activating point mutations, copy number gains/amplifications, and RNA and protein overexpression. Amplification and overexpression are typically mutually exclusive with point mutations. HER2 copy number was first determined in the five exome-sequenced cases (FIG. 9 and FIGS. 11A-11L). No numerical CFA9 gains or focal HER2 amplifications were detected. However, these cases predominantly bore somatic putatively activating point mutations and might not be expected to contain concomitant gains. Therefore, we evaluated HER2 RNA and protein expression by qRT-PCR and IHC. RNA samples from 49 lung tumors (nine HER2-mutant) were evaluated alongside 14 normal lung tissue samples distal to tumor areas but from the same lung lobe. Median HER2 expression fold-change relative to expression of the house-keeping gene HPRT in normal lung samples was 1.06 (range 0.28-4.11) and in tumors was 0.85 (range 0.07-4.50) (FIGS. 20A-20B). No significant difference in relative HER2 expression was observed between tumor and normal or HER2-mutant and HER2 WT groups.

Figure 6:
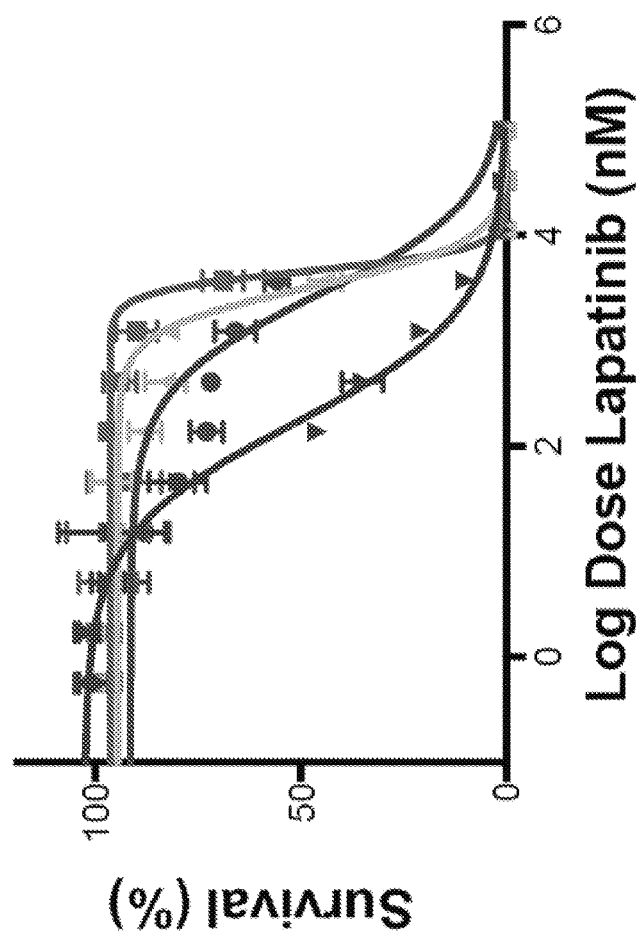
FIG. 6 illustrates canine lung cancer cell line sensitivity to lapatinib and shows four canine cell lines (three HER2 WT and one HER2 V659E) were treated with 14 lapatinib doses ranging from 100 μM to 5.5×10-2 nM for 72 hours; survival rates were assessed by luminescence using Synergy Mx (Biotek plate reader) and expressed as the percentage of survival compared to DMSO vehicle control.

Additionally, in order to quantify HER2 protein expression in cPAC, digital image analysis was performed on eight tumors from FFPE. Three of the samples bore the HER2 V659E hotspot mutations, one bore HER2 A664T, and four were HER2 WT. All cases were positive for HER2 staining with homogeneous and diffuse staining of tumor cell cytoplasm and cell membrane, but no staining in adjacent stroma or vasculature (FIG. 6). Positive staining was observed in bronchial epithelium of the adjacent non-affected lung in all cases. Consistent with absence of observed HER2 amplifications, no significant differences (mean±SEM) were detected in the tumor positivity percentage for HER2 (47±5.4 and 35±5.1) between the WT and HER2-mutant groups, respectively. No significant differences in HER2 staining were present for percent minimum (51±2.9 WT vs. 55±5.1, HER2 mutations) or percent maximum (97±0.31 WT vs. 96±0.47 HER2 mutations) stain intensity (FIGS. 18A-18B). Overall, most tumors showed moderate expression of HER2 based on qRT-PCR and IHC with some variability, but levels were typically consistent with those seen in normal tissue and did not vary based on HER2 mutation status.

The results herein describe that HER2 is constitutively active in HER2-V659E-mutant cPAC cell lines.

Figure 2A:
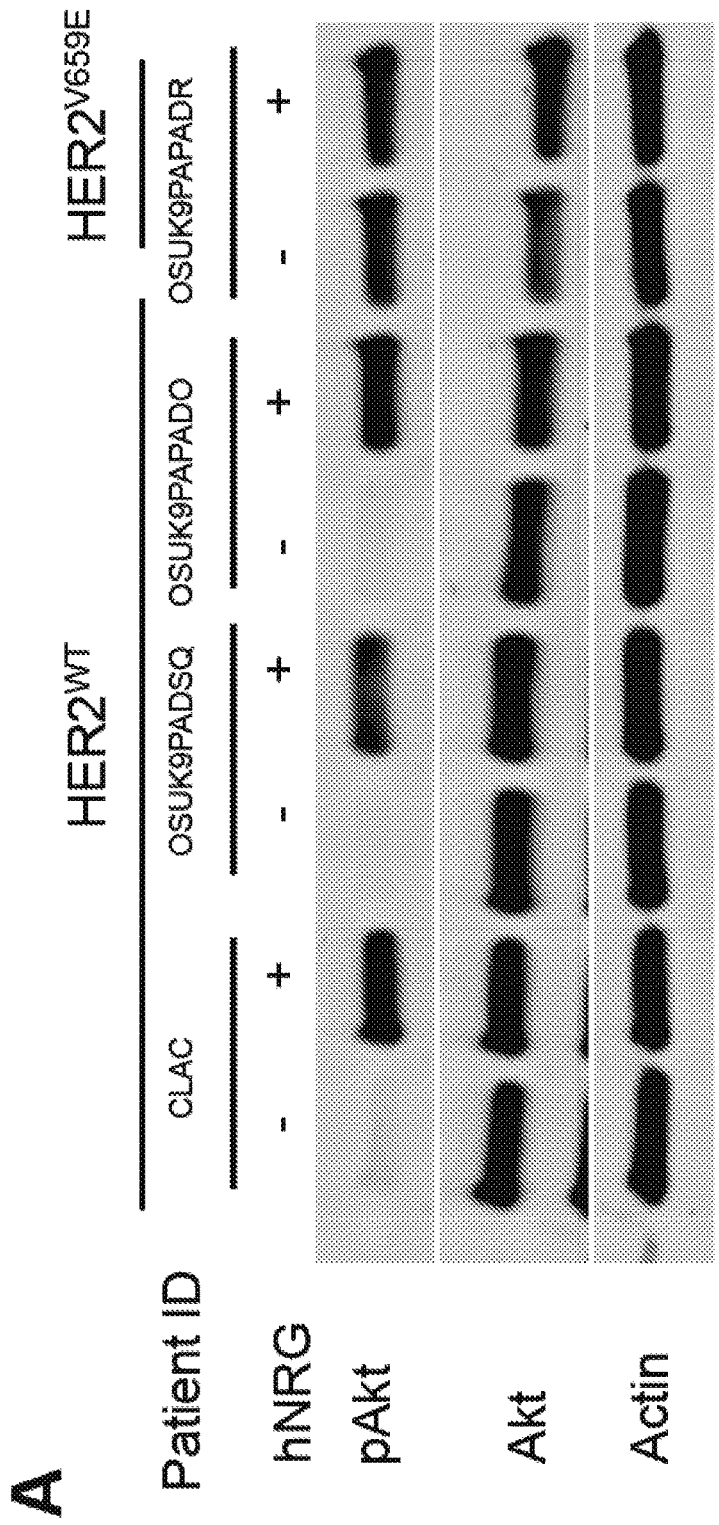
FIGS. 2A-2C illustrate results showing canine lung cancer HER2 mutant HER2 V659E constitutively activates downstream HER2 signaling and is associated with response to HER2 inhibitors in primary canine pulmonary adenocarcinoma (cPAC) cell lines.

HER2 is a transmembrane receptor tyrosine kinase typically activated by homo- or hetero-dimerization with other HER family receptors. HER2 mutations or overexpression drive constitutive downstream signaling. In human cancers, HER2 V659E mutations stabilize dimers to increase HER2 autophosphorylation, EGFR phosphorylation, activation of phosphatidyl-inositol-3-kinase (PI3K), and activation of mitogen-activated-protein-kinase (MAPK) pro-survival signaling pathway members (e.g. AKT and ERK) relative to wild-type HER2 (18,19). To determine whether HER2 V659E constitutively activates downstream signaling in cPAC, we first validated HER2 genotype in seven canine lung cancer cell lines through amplicon sequencing, ddPCR or Sanger sequencing of the V659 locus, Sanger sequencing of all HER2 coding regions, and/or aCGH to determine HER2 copy number status as previously published (FIG. 15) (20). One cell line, OSUK9PAPADO, bore a low allele frequency HER2 V659E mutation when sequenced by amplicon panel at low passage (passage 4) as a primary culture, but had lost this allele in later established passages (passage 15) characterized by Sanger sequencing and ddPCR. The latter passage were utilized for functional studies. We thus evaluated HER2 activation in one HER2 V659E cPAC cell line, OSUK9PAPADRe, and three HER2 WT cell lines (two cPAC-CLAC and OSUK9PAPAPADO- and one cPASC-OSUK9PADSQ) by Western blotting for total and phospho-AKT in the presence and absence of the ErbB ligand, neuregulin (hNRG) post-serum starvation. Only the HER2 V659E line, OSUK9PAPADRe, showed constitutively high AKT phosphorylation post-starvation even in the absence of hNRG stimulation (FIG. 2A).

The results herein describe that HER2-V659E-mutant cPAC cell lines are hypersensitive to HER2 inhibitors.

Figure 2B:
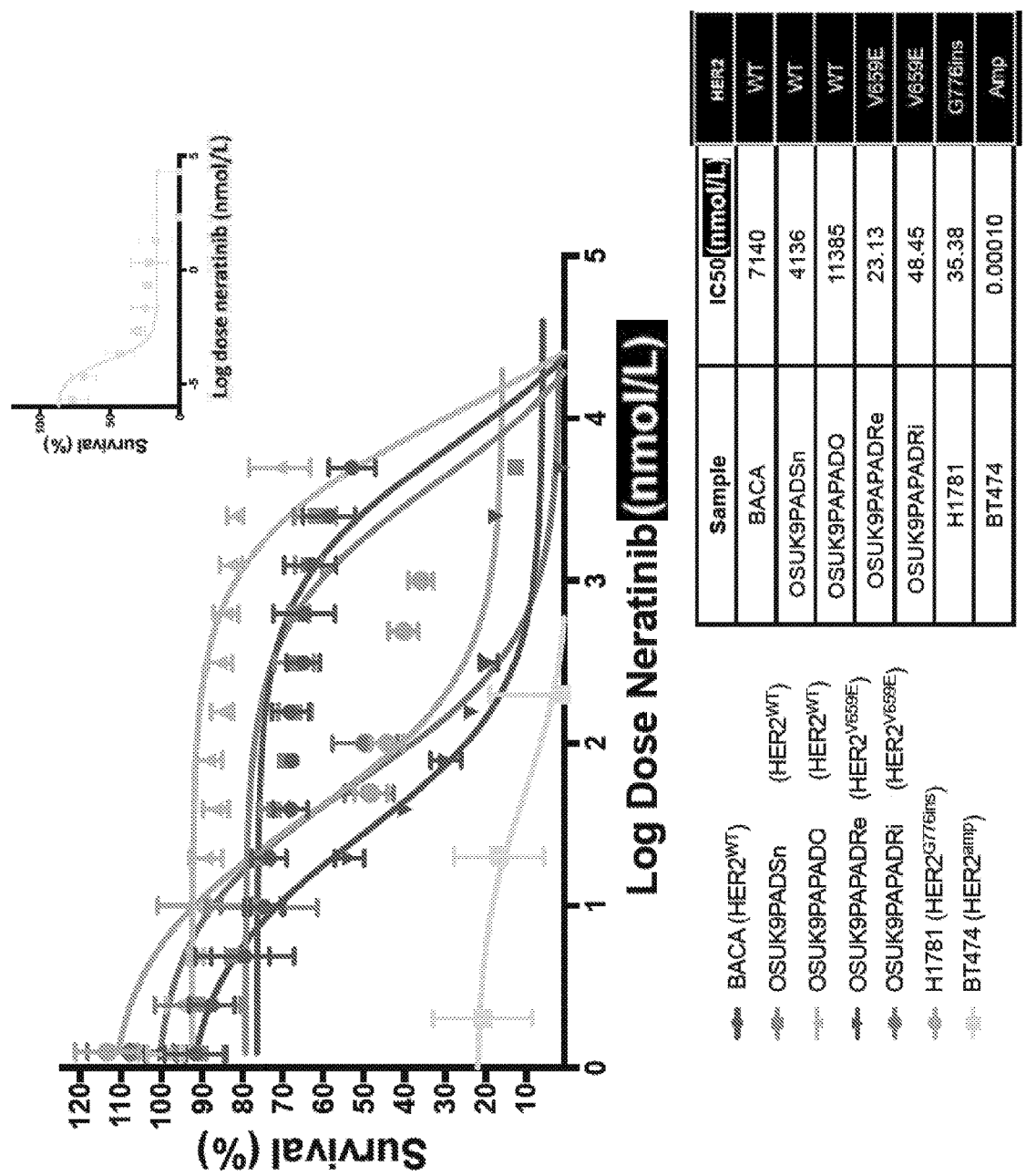
Figure 2C:
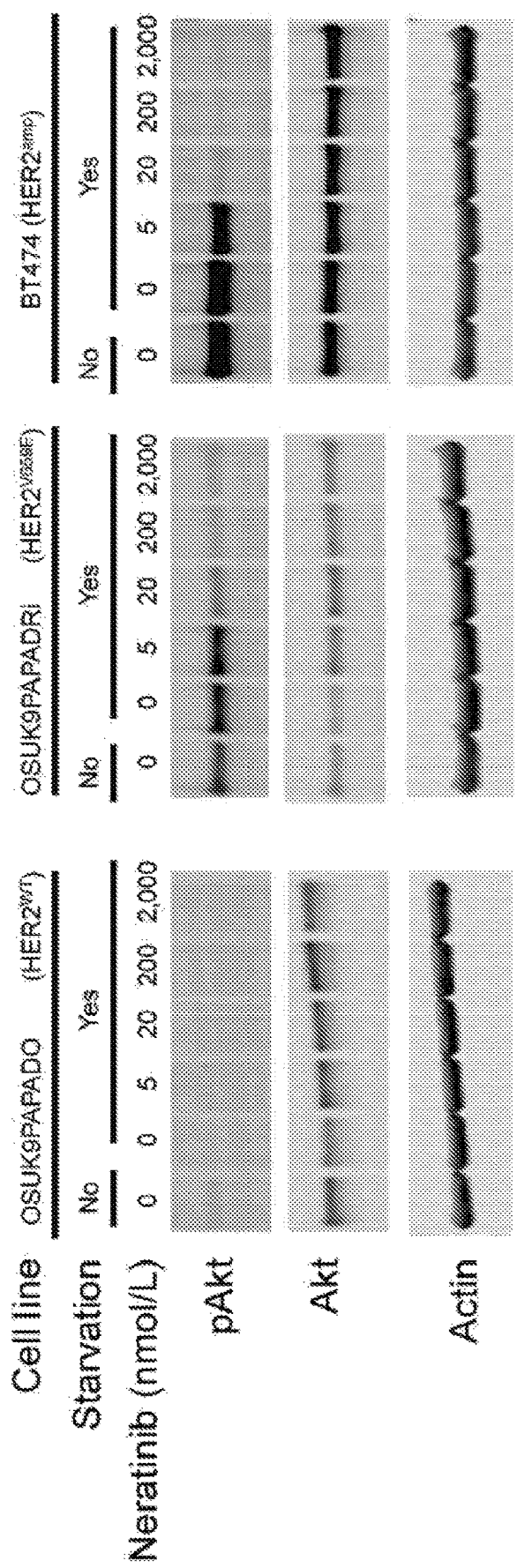
Figure 3A:
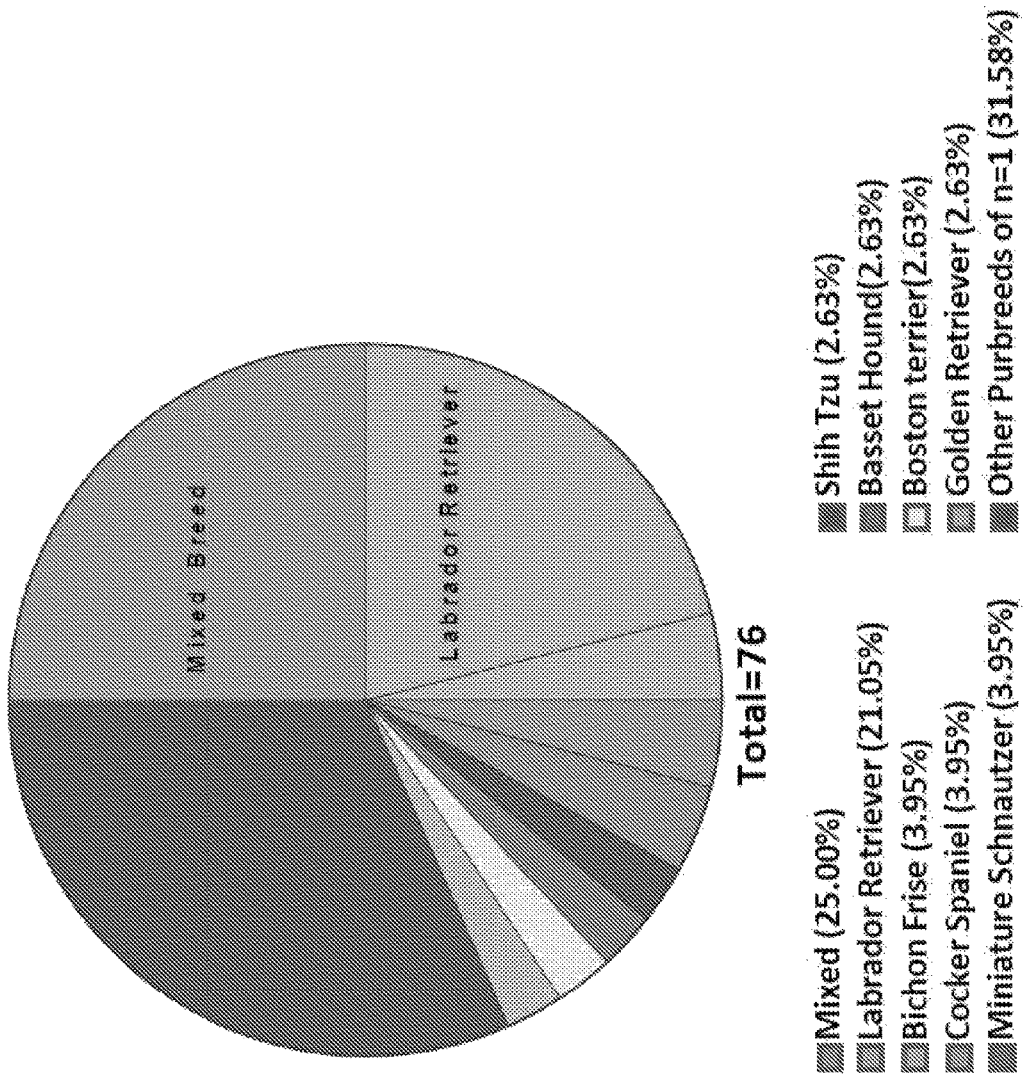
FIGS. 3A-3F illustrate extended clinical annotation of primary canine lung cancer patients.
Figure 3B:
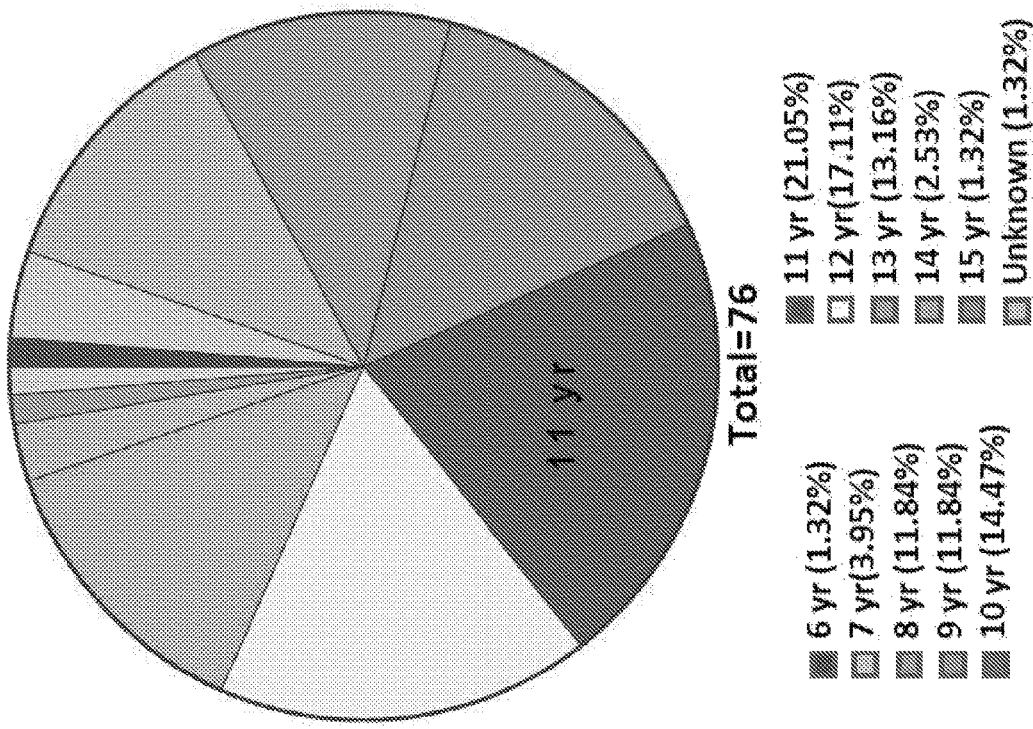
Figure 3C:
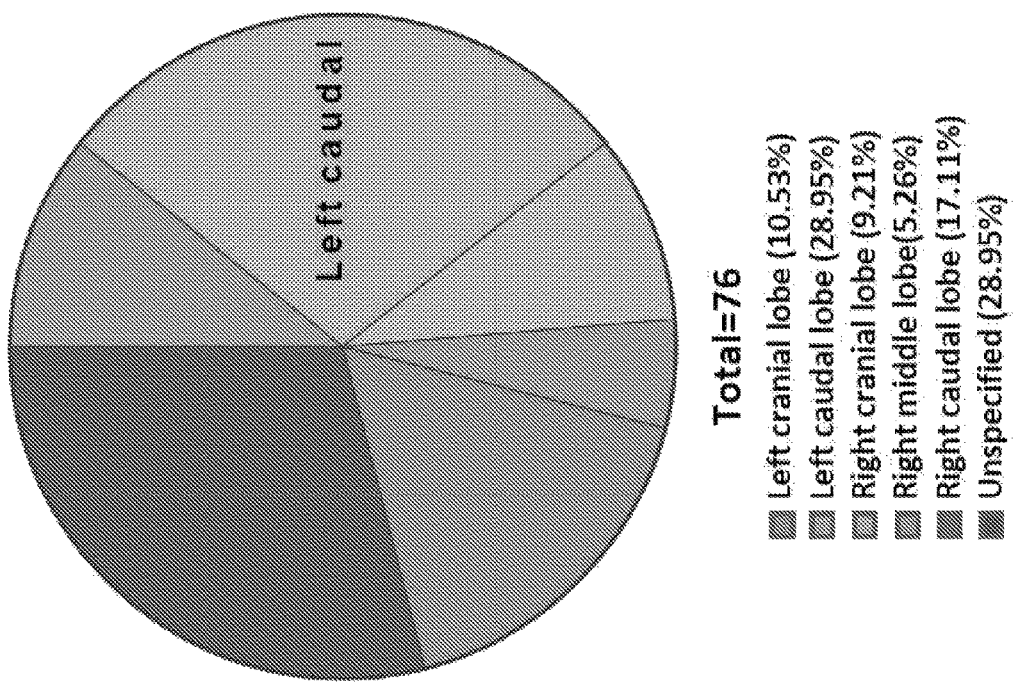
Figure 3D:
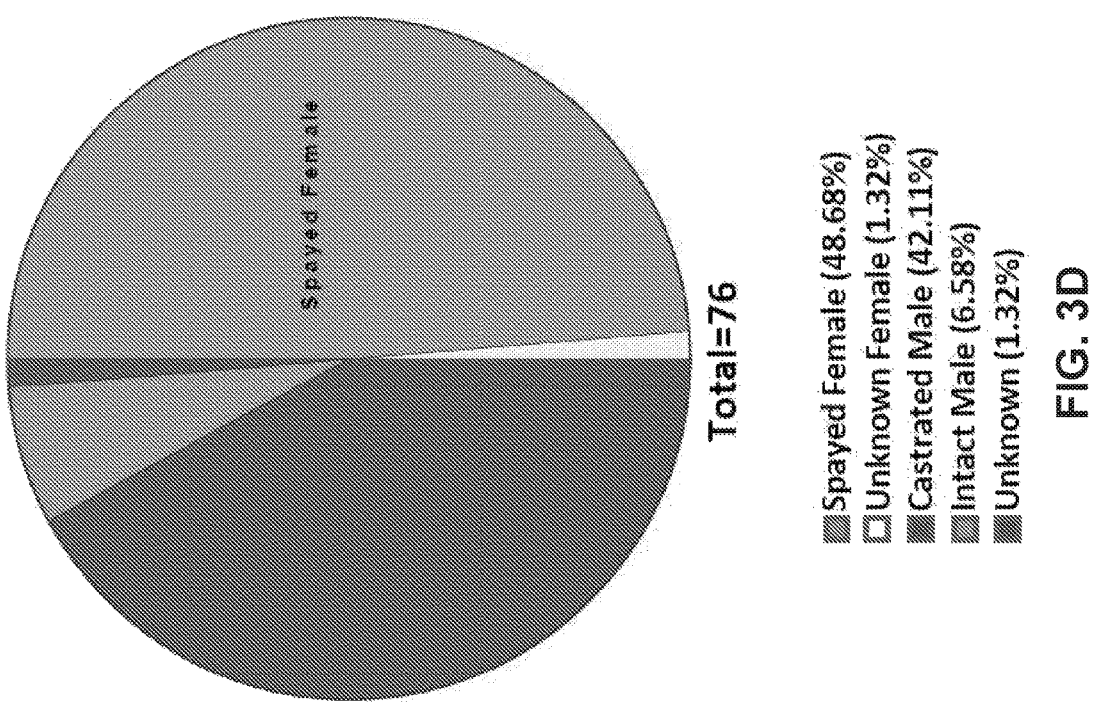
Figure 3E:
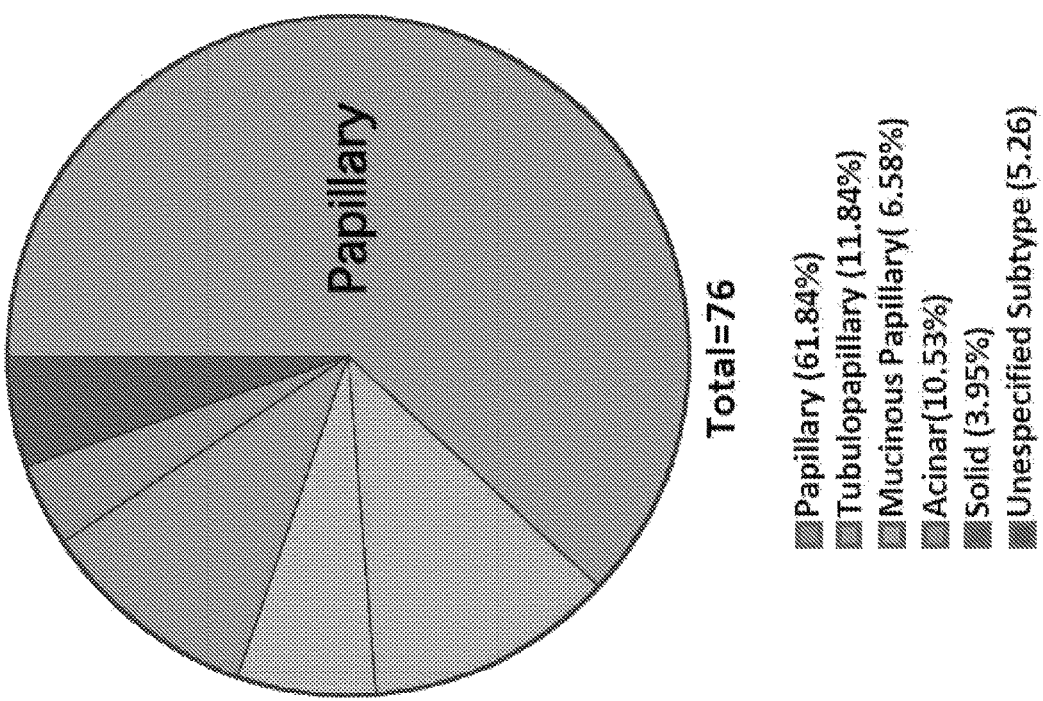
Figure 3F:
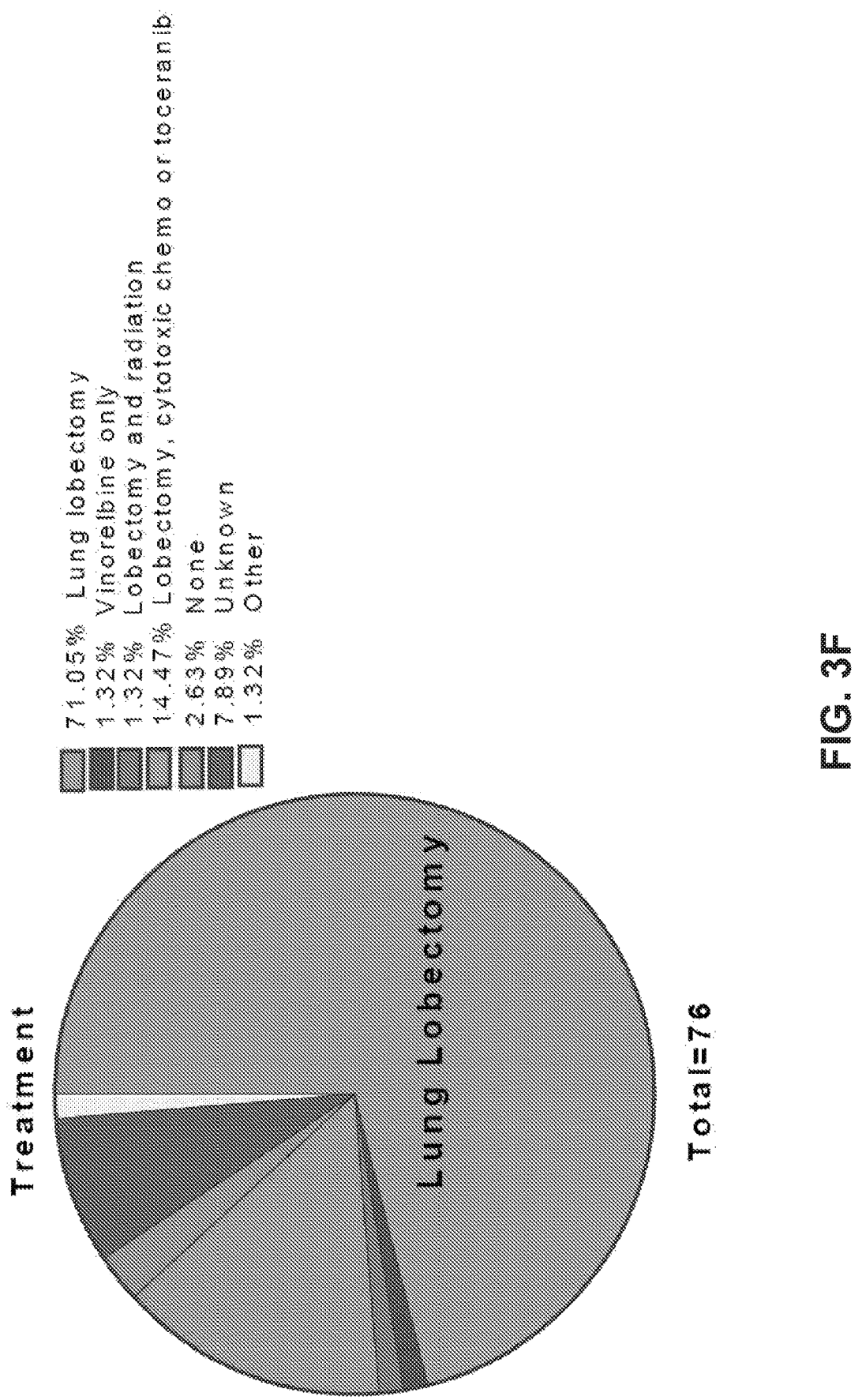
Figure 21:
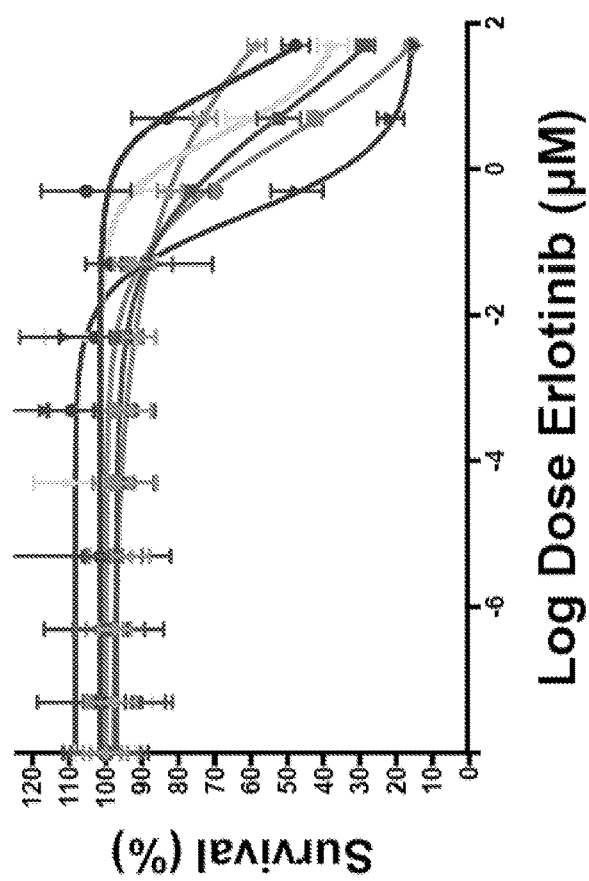
FIG. 21 illustrates canine primary lung cancer cell line sensitivity to erlotinib; five canine cell lines (three HER2 WT and two HER2 V659E) and one human cell line BT474 (HER2 amp) were treated with 10 erlotinib doses ranging from $5\times10^{-8}$ to 50 μM for 72 hours with CellTiterGlo viability endpoints measured and shown as percent growth inhibition relative to DMSO vehicle control.
Figure 22:
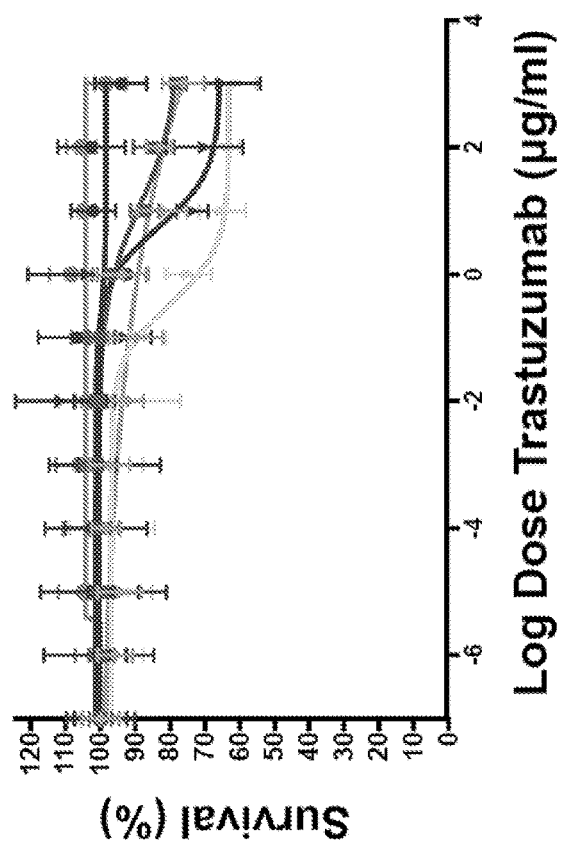
FIG. 22 illustrates canine primary lung cancer cell line sensitivity to trastuzumab; five canine cell lines (three HER2 WT and two HER2V 659E) and one human cell line BT474 (HER2 amp) were treated with 10 trastuzumab doses ranging from $1\times10^{-6}$ μg/ml to 1000 μg/ml for 72 hours with CellTiterGlo viability endpoints measured and shown as percent growth inhibition relative to PBS vehicle control. Relative survival was measured with respect of the sensitive cell line BT474.

To determine the potential efficacy of anti-HER2 agents for treatment of HER2 V659E cPAC, we performed dose-response studies of selected tyrosine kinase inhibitors (TKIs: neratinib, lapatinib, and erlotinib) and a humanized HER2 recombinant monoclonal antibody (mAb), trastuzumab, which binds the extracellular juxtamembrane domain IV of HER2. We first assessed differential sensitivity of HER2 V659E and HER2 WT canine lung cancer cell lines to lapatinib (HER2 and EGFR inhibitor) and neratinib (HER2, HER4, and EGFR inhibitor). Five cPAC cell lines (two HER2 V659E and three HER2 WT) were treated with neratinib and four (one HER2 V659E and three HER2 WT) with lapatinib for 72 hours. Two HER2-mutant human cancer cell lines-BT474 (HER2 AMP) and H1781 (kinase domain HER2 G776ins)—were treated as positive drug controls (18, 21) (FIGS. 2B and 6). Significant differences in viability were observed between HER2 V659E and HER2 WT cPAC cell lines for both TKIs (IC50s<200 nM in HER2 V659E versus IC50s>2500 nM in HER2 WT). All HER2-mutant cell lines were sensitive to neratinib with IC50s<50 nM (FIG. 2B), significantly lower than those observed for HER2WT cells (IC50s>2.7 µM, p=0.0079). We additionally observed a neratinib dose-dependent decrease in p-AKT in the HER2-mutant cell lines OSUK9PAPADRi (HER2 V659E) and BT474 (HER2amp) whereas p-AKT levels in OSUK9PAPADO (HER2 WT) were low at all treatment levels (FIG. 2C). Given that HER2 receptors dimerize with EGFR, we then evaluated differential sensitivity of the five canine cell lines and the human BT474 control line to the EGFR inhibitor, erlotinib. HER2 V659E IC50s were greater than those of neratinib at 220 nM and 1.17 µM. HER2 WT IC50s ranged from 1.10-15.38 µM (FIG. 21). Finally, we evaluated the HER2-mutation-dependent effects of trastuzumab in the five cPAC cell lines described above (two HER2 V659E and three HER2 WT) and the positive control cell line, BT474, at doses ranging from $1 \times 10^{-6}$ µg/ml to 1 mg/ml for 72 hours. While trastuzumab did not decrease viability below 50% for any of the cell lines at 72 hours, the greatest dose-dependent responses were observed in the BT474 control line (65% viability at 10 µg/ml, consistent with prior publications) and in the HER2 V659E line OSUK9PAPADRe (74% viability at 10 µg/ml). More limited responses were observed in OSUK9PAPADO (HER2 V659E) and OSUK9PADSn (HER2 WT) and no responses at any dose in OSUK9PAPDRi (HER2 V659E) and BACA (HER2 WT) (FIG. 22). Overall, these studies support that HER2 V659E in cPAC is an activating event that stabilizes HER2 homo- and hetero-dimers, confers dependency on downstream signaling, and confers sensitivity to targeted HER2 tyrosine kinase inhibition.

Discussion and Conclusion

Through multi-platform next-generation sequencing of 88 naturally occurring primary canine NSCLC cases (77 tumors and 11 cell lines), we describe for the first time the detailed genomic underpinnings of this cancer. The cohort included major NSCLC subtypes occurring in dogs and humans: cPAC (n=74, cPASC (n=11), and cPSCC (n=3) (FIGS. 7A-7D, FIGS. 3A-3F). Although lung cancer may be over-represented in Doberman pinschers, Australian shepherds, Irish setters, and Bernese mountain dogs (7), Labrador retrievers comprised the largest pure breed in this cohort (21%) followed by mixed breeds (25%). The cohort was gender-balanced (52% females), primarily neutered/spayed (92%), and bore a median age at diagnosis of 11 years. Given that dogs are companion and service animals that typically share the same environment with humans, they may have a role to play as sentinels for human lung cancer environmental risk factors. Some data suggests that environmental risks are shared across species. For example, an increased risk of developing cPAC (OR: 2.4, CI 95%: 0.7-7.8; p=not given) trends towards association with having a smoker in the home in dogs with short (brachycephalic) or medium length (mesocephalic) noses, such as Labrador retrievers (22).

Although second-hand smoke exposure in the dogs in our cohort is possible given that exposure was not recorded, genomic landscapes of human lung cancers in never-smokers have not been shown to differ based on exposure to second-hand smoke (23). Exposure to other environmental carcinogens such as air pollutants may also play a role in development of lung cancers. For example, increased lung cancer risk may be present in dogs with higher amounts of carbon deposits known as anthracosis (OR: 2.1, CI95%: 1.20-3.70; p<0.01) (24), although in humans anthracosis has been commonly observed in normal lungs as well as tumors and lymph nodes. In this cohort, anthracosis was recorded in 15 cases and pneumoconiosis (lung disease associated with pollutant exposure) in one case. However, no associations between anthracosis annotation and genetic features of these cases were observed. Overall, our studies included broad representation of lung cancer across histologic subtypes, breeds, ages, and pollutant exposures reflective of primary canine lung cancer diversity seen in the clinical setting in the United States. Overall, support exists for shared etiologies between canine and human never-smoker lung cancer including secondhand smoke, organic dusts, and outdoor and indoor air pollution, suggesting that study of canine lung cancer can be informative for understanding human lung cancer risks and etiologies. Genomic characterization of canine lung cancers is a first major step towards understanding variables influencing lung cancer development in pet dogs.

Unique genomic characteristics of human never-smoker lung cancer include low somatic mutation burden, C:G>T:A enrichment, and activating mutations or fusions impacting EGFR (45%), ALK (5-11%), ROS (1.5-6%), HER2 (3-5%), and RET (2%) (4,25). Here, we also observed a low somatic burden of SNVs, CNVs, and SVs through exome sequencing in five matched tumor/normal cPAC pairs. We additionally observed that the most common mutation signature in these five cases was the age-associated COSMIC Signature 1A in 4 of 5 (80%) similar to the enrichment seen in human NSCLC (FIGS. 4A and 4B). This signature is associated with age in many human cancers, putatively the result of spontaneous deamination of 5-methyl-cytosine. COSMIC Signature 2, associated with APOBEC cytidine deaminase activity, was also present in two cases. This signature, is most prominently associated with cervical and bladder cancers, but is also commonly found in lung adenocarcinoma and squamous cell carcinoma. While these signatures are sometimes associated with APOBEC gene variants in human cancers (26), no putatively pathogenic germline or somatic APOBEC mutations were observed. Based on our studies, primary canine lung cancers bear a low mutation burden (TMB mean of 2.04 mutations/Mb) and mutation signatures reflective of those seen in human never-smoker lung cancers.

The most common recurrently mutated genes containing somatic potentially pathogenic SNVs in the full cohort included HER2 (31.5%), TP53 (12.5%), PTEN (5.7%), SMAD4 (4.5%), KRAS (4.5%), VHL (3.4%) and HRAS (2.3%). Recurrent CDKN2A/B focal deletions were also observed in 2 of 5 (40%) cases (FIGS. 1A and 1B) along with a homozygous missense mutation, G50R, equivalent to human codon G101 mutations. CDKN2A deletions were the most common alteration by frequency, occurring at rates comparable to those in human NSCLC. Two focal deletions were observed out of five exome-sequenced cases with signs of larger-scale CFA11 losses in remaining cases (FIG. 9). CDKN2A is mutated in approximately 30% of all human NSCLC, primarily via homozygous deletion, and this number is reduced to around 25% in never-smokers. The next most common alterations after CDKN2A and HER2 were TP53 missense and truncating mutations comparable to DNA binding domain mutations in human TP53. Similar to human NSCLC, we observed a reduced burden of TP53 mutations (12.4%, two stop gains and nine likely pathogenic missense mutations) relative to human smoker NSCLC in which more than half of tumors are mutated. PTEN mutations were the next most common at 5.6%. PTEN is mutated in ~9% of human NSCLC, but only ~2% of never-smoker NSCLC.

We additionally identified four somatic mutations in the tumor suppressor SMAD4, mutated in ~5% of human NSCLC at comparable rates in smoker and never-smoker cancer. KRAS mutations are the most common oncogenic mutations in human smoker NSCLC (~30-40% of cases), but occur at reduced frequencies in never-smoker lung cancer (0-7%). KRAS mutations in our cohort were rare (2 G12V, 1 G12D, and 1 Q61K), but comparable to human hotspots. Canine HRAS missense mutations were also located in human-equivalent hotspots (Q61L, F78S). Additional likely pathogenic somatic mutations included individual cases of AKT1 amplification, KIT/KDR amplification, EGFR A726T (human A755), MET M1269V (human M1268), and VHL P97L (human P97). WWTR1, the only COSMIC gene bearing a somatic translocation in exome-sequenced cases, has been shown to undergo translocation with CAMTA1 in human epithelioid hemangioendothelioma (27). We identified a WWTR1 translocation of unknown consequence with ATP5F1. Although we identified translocations occurring in coding regions in five exome-sequenced tumors, it remains possible that, as in human never-smoker lung cancer, EML4-ALK fusions, ROS1 fusions, RET fusions, and other fusions may also be present in canine lung cancer.

In addition to charting the landscape of cPAC, we have found recurrent KRAS and TP 53 mutations in cPASC and provide a view of possible drivers in cPSCC. In cPASC, HRAS Q61L and KRAS Q61K each occurred in one case. Finally, while no recurrent mutations were identified in the three cPSCCs, we identified one case with somatic BRAF V588E (equivalent to the human V600E hotspot) and another bearing PTPN11 G503V (equivalent to the human G503V hotspot).

HER2 contained the most somatic mutations with hotspot mutations occurring solely in cPAC (37.8%). HER2 is a well-characterized human oncogene and drug target mutated in ~6% of all cancers based on cBioPortal query of 10,967 cases in the TCGA pan-cancer atlas (28,29). Most alterations are focal amplifications, but activating point mutations and insertions are also common. In human NSCLC, HER2 mutations are oncogenic drivers in ~1-4% of cases with mutations and insertions mostly in exon 20 at codon 776 resulting in constitutive HER2 kinase domain activation and downstream signaling through PI3K and MAPK pathways (25,30,31). HER2 may also be more commonly mutated in human never-smoker lung cancer, with point mutations at frequencies reported at 3-5% (32), predominately in female never-smokers who carry a median OS of ~2 years (31). HER2 TMD polar mutations (HER2 V659E/D, HER2 G660D) are present in 0.18% of human lung adenocarcinomas and are exclusive with HER2 kinase domain mutations (33). Amplicon analysis capable of identification of point mutations and small insertions or deletions covered canine HER2 exons 8 and 17-22 including transmembrane and kinase domains. Additionally, Sanger sequencing of all exons in five canine cell lines with wild-type HER2 based on amplicon sequencing (OSUK9PAD, BACA, CLAC, K9PADSQ and OSULSCC1) found no somatic HER2 mutations in other sites (FIG. 15). It is nonetheless possible that somatic mutations occurring in other regions of HER2 were not identified in amplicon-sequenced samples even though data facilitating functional interpretation of these variants would be limited.

In addition to point mutations, HER2 amplification has also been identified in ~1% of human NSCLC (25), with enrichment in EGFR-inhibitor-resistant tumors (34). Protein overexpression is reported in 6-35% of tumors including up to 42% of adenocarcinomas and correlates with poor prognosis (35-38). We detected no somatic HER2 focal amplifications or numerical CFA9 gains in five exome-sequenced cases (FIGS. 1B and 9) or two previously aCGH-profiled cell lines. However, four of these seven cases contained somatic, putatively activating HER2 SNVs. Given that HER2 amplification/overexpression and SNVs are typically mutually exclusive, it remains possible that our broader amplicon cohort contained undetected HER2 amplifications. We therefore utilized qRT-PCR and IHC studies to more broadly assess HER2 overexpression and did not find evidence for significant tumor-specific HER2 overexpression (FIGS. 20A-20B and FIGS. 6 and 17). Thus, it is unlikely that HER2 is frequently amplified in canine lung cancer.

Overall, though we observed a similar mutation spectrum in canine lung cancer relative to human never-smoker NSCLC, the notable exception is abundance of HER2 mutations and lack of EGFR mutations. EGFR mutations occur at low frequency in human smoker lung cancers (0-7%), but are enriched in human never-smokers (~45%). Canine HER2 shares normal and oncogenic roles with human HER2 based on sequence conservation (92.2% protein identity) and prior study of its role in canine cell signaling. HER2V659E occurs at a highly conserved residue (100% identity in the TMD from amino acids 654-674) and to the neu (rat HER2) variant identified in a rat glioblastoma cell line that originally led to discovery of HER2's oncogene status (39). HER2 has previously been implicated in canine cancers via overexpression by IHC and qRT-PCR in canine mammary tumors (40), through its utility as a vaccine target in canine osteosarcoma (41), and through downstream signaling activation in canine lung cancer (10). Thus, HER2 sequence and pathway biology is conserved, so the predominance of HER2 mutations as erbB signaling activators in lieu of EGFR mutations in cPAC may be the result of cell-of-origin and genetic background influences. Cell of origin determination in canine lung cancers is challenging because the pulmonary adenocarcinoma diagnosis includes tumors arising from primary, secondary and tertiary bronchioles and thus topographic origin can be difficult to determine. However, evidence supports that HER2 is broadly important for canine pulmonary epithelium. For example, neuregulin-stimulated HER2 increases proliferation in pulmonary epithelial cells by activation of the JAK-STAT pathway. Further, when HER2 activation is blocked via antibodies to neuregulin or HER2 in a scratch wound-healing assay of pulmonary epithelial cells, wound closure is significantly delayed, suggesting HER2 activation is necessary for epithelial proliferation (42).

We have also found that IHC of canine normal lung showed stronger HER2 staining of all bronchioalveolar regions when compared to EGFR staining of normal adult canine lung. These data suggest that HER2 may play a more central role than EGFR in canine alveolar and airway epithelial cells during chronic lung injury and for general proliferative processes. Prolonged activation could lead to cellular transformation and neoplasia. Further, EGFR mutations have been associated with particular histotypes—i.e. they are frequent in lepidic and acinar patterns and infrequent in mucinous patterns in female Asian never-smoker PAC. In this population, the most frequent adenocarcinoma histotype was acinar (142 cases, 71.7%), followed by papillary (18 cases, 9.1%), solid (17 cases, 8.6%), lepidic (9 cases, 4.5%), and micropapillary (1 case, 0.5%). Interestingly, our canine cohort had predominantly papillary morphology (69%) with only 5% acinar (5%). Therefore, differences in cell of origin in both species could account for the differences in EGFR mutation frequencies. Background genetic context likely also plays a primary role in shaping enrichment for HER2 mutations in cPAC. This is also true in human lung cancer where EGFR mutation frequency varies by more than 3-fold between different human populations. The Asian population has a very high rate of EGFR mutation among the never-smoking population, up to 51.4% overall and as high as 64% in some populations such as the Kinh, versus about 20% in Caucasians (43-45). These differences in human populations suggest a sensitivity of EGFR mutations to genetic context. Conversely, HER2 mutations are found in all human populations at about the same frequency, suggesting that HER2 mutations in humans may not be as sensitive to genetic background.

We have additionally shown that HER2 hotspot mutations can be detected in the plasma of dogs bearing HER2 V659E cPACs even at early disease stages (FIG. 1E and FIGS. 16A-16C). In human NSCLC, ctDNA has been shown to be significantly enriched in plasma relative to controls with key genetic features identifiable via liquid biopsy. Associations have been found between ctDNA levels and tumor stage, grade, lymph node status, metastatic sites, response, and survival (46,47). The first FDA-approved liquid biopsy test was the cobas EGFR Mutation Test v2, a real-time PCR assay utilized in NSCLC for the detection of EGFR exon 18-21 mutations in tissue or plasma to guide EGFR inhibitor treatment assignment (48,49). Our proof-of-principle study supports that ctDNA is also detectable in primary canine lung cancer patient plasma. A non-invasive HER2 V659E assay will enable genotyping patients when tumor tissue is limited and may have a role in treatment monitoring or detection of minimal residual disease. This assay will also facilitate prospective analysis of HER2 V659E's diagnostic and prognostic value.

In human cancers, HER2 TMD mutations constitutively activate pro-survival HER2 signaling (33) and are associated with HER2 inhibitor responses (19). We have confirmed in this study that, similar to human HER2 TMD mutants, canine HER2 V659E cell lines constitutively activate downstream signaling through AKT and are selectively sensitive to the HER2 TKI inhibitors neratinib and lapatinib in vitro (FIGS. 2A-2B and FIG. 6). In order to further assess the role of dimerization in HER2 activation in cPAC, we also performed drug dose response studies for erlotinib and trastuzumab (FIGS. 21 and 22). One of two HER2-mutant cell lines showed erlotinib sensitivity. Trastuzumab responses were poor overall and did not correlate with HER2 status, although dose-response relationships were observed in three of five cell lines. Trastuzumab's human binding site is highly conserved in canine (only a single amino acid difference) and trastuzumab has been shown to bind canine HER2 and inhibit proliferation of HER2-overexpressing canine cancer cell lines (50). However, even the human HER2-amplified cell line, BT474, did not show viability reduction below 50% in our hands. It is likely that the effects of trastuzumab on CellTiterGlo viability are broadly muted at the 72-hour timepoints we utilized. Overall, these studies indicate that HER2 V659E in cPAC is an activating event that stabilizes HER2 homo- and heterodimers, confers dependency on downstream signaling, and confers sensitivity to targeted HER2 tyrosine kinase inhibition. We have charted the genomic landscape of primary canine lung cancers including the NSCLC subtypes cPAC, cPASC, and cPSCC. We have identified recurrent HER2 mutations in these cancers and present, to our knowledge, the first complete suite of evidence supporting an oncogenic role for and dependency on constitutively activating mutations in HER2 in a canine cancer.

Further work is needed to exhaustively profile these tumors, particularly according to variation across breeds and through integration of additional data types including epigenomics, RNA sequencing, and proteomics. However, these data nonetheless offer significant immediate diagnostic and therapeutic opportunities for dogs with primary lung cancer and aid comparative understanding of never-smoker and HER2-mutant lung cancer. These findings set the stage for HER2 inhibitor toxicity, dose-finding, and efficacy studies in dogs that will guide utilization of HER2 inhibitors in the veterinary clinic.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

1. Wilson D W. Tumors of the Respiratory Tract. In: Meuten D J, editor. Tumors in domestic animals. 5th ed: John Wiley & Sons; 2017. p 467-98.
2. Clément-Duchêne C, Wakelee H. Lung Cancer Incidence in Never Smokers. European Journal of Clinical & Medical Oncology 2010; 2 (2).
3. Samet J M, Avila-Tang E, Boffetta P, Hannan L M, Olivo-Marston S, Thun M J, et al. Lung cancer in never smokers: clinical epidemiology and environmental risk factors. Clin Cancer Res 2009; 15(18): 5626-45 doi 10.1158/1078-0432.CCR-09-0376.
4. Govindan R, Ding L, Griffith M, Subramanian J, Dees N D, Kanchi K L, et al. Genomic landscape of non-small cell lung cancer in smokers and never-smokers. Cell 2012; 150(6): 1121-34 doi 10.1016/j.cell.2012.08.024.
5. Hellmann M D, Ciuleanu T E, Pluzanski A, Lee J S, Otterson G A, Audigier-Valette C, et al. Nivolumab plus Ipilimumab in Lung Cancer with a High Tumor Mutational Burden. N Engl J Med 2018; 378(22): 2093-104 doi 10.1056/NEJMoa1801946.
6. Hahn F F, Muggenburg B. A., Griffith W. C., editor. Primary lung cacer in the longevity study/control population of the ITRI beagle dog colony. Springfield, V A: National Technical Information Service; 1992. 133-6 p.
7. Griffey S M, Kraegel S A, Madewell B R. Rapid detection of K-ras gene mutations in canine lung cancer using single-strand conformational polymorphism analysis. Carcinogenesis 1998; 19(6): 959-63.
8. Kraegel S A, Gumerlock P H, Dungworth D L, Oreffo V I, Madewell B R. K-ras activation in non-small cell lung cancer in the dog. Cancer Research 1992; 52(17): 4724-7.
9. Tierney L A, Hahn F F, Lechner J F. p53, erbB-2 and K-ras gene alterations are rare in spontaneous and plutonium-239-induced canine lung neoplasia. Radiation Research 1996; 145(2): 181-7.
10. Mariotti E T, Premanandan C, Lorch G. Canine pulmonary adenocarcinoma tyrosine kinase receptor expression and phosphorylation. BMC veterinary research 2014; 10:19 doi 10.1186/1746-6148-10-19.
11. Forbes S A, Beare D, Boutselakis H, Bamford S, Bindal N, Tate J, et al. COSMIC: somatic cancer genetics at high-resolution. Nucleic acids research 2017; 45 (D1): D777-D83 doi 10.1093/nar/gkw1121.
12. Alexandrov L B, Nik-Zainal S, Wedge D C, Aparicio S A, Behjati S, Biankin A V, et al. Signatures of mutational processes in human cancer. Nature 2013; 500(7463): 415.
13. Gehring J S, Fischer B, Lawrence M, Huber W. SomaticSignatures: inferring mutational signatures from single-nucleotide variants. Bioinformatics 2015; 31(22): 3673-5 doi 10.1093/bioinformatics/btv408.
14. Sherry S T, Ward M-H, Kholodov M, Baker J, Phan L, Smigielski E M, et al. dbSNP: the NCBI database of genetic variation. 2001; 29(1): 308-11.
15. Bai B, Zhao W-M, Tang B-X, Wang Y-Q, Wang L, Zhang Z, et al. DoGSD: the dog and wolf genome SNP database. 2014; 43 (D1): D777-D83.
16. Liu C, Cui H, Gu D, Zhang M, Fang Y, Chen S, et al. Genetic polymorphisms and lung cancer risk: Evidence from meta-analyses and genome-wide association studies. 2017; 113:18-29.
17. Perdigones N, Murtaza M. Capturing tumor heterogeneity and clonal evolution in solid cancers using circulating tumor DNA analysis. Pharmacol Ther 2017; 174:22-6 doi 10.1016/j.pharmthera.2017.02.003.
18. Suzawa K, Toyooka S, Sakaguchi M, Morita M, Yamamoto H, Tomida S, et al. Antitumor effect of afatinib, as a human epidermal growth factor receptor 18. ...2-targeted therapy, in lung cancers harboring HER2 oncogene alterations. Cancer Sci 2016; 107(1): 45-52 doi 10.1111/cas.12845.
19. Ou S I, Schrock A B, Bocharov E V, Klempner S J, Haddad C K, Steinecker G, et al. HER2 Transmembrane Domain (TMD) Mutations (V659/G660) That Stabilize Homo- and Heterodimerization Are Rare Oncogenic Drivers in Lung Adenocarcinoma That Respond to Afatinib. J Thorac Oncol 2017; 12(3): 446-57 doi 10.1016/j.jtho.2016.11.2224.
20. Clemente-Vicario F, Alvarez C E, Rowell J L, Roy S, London C A, Kisseberth W C, et al. Human genetic relevance and potent antitumor activity of heat shock protein 90 inhibition in canine lung adenocarcinoma cell lines. PloS one 2015; 10(11): e0142007.
21. Canonici A, Gijsen M, Mullooly M, Bennett R, Bouguern N, Pedersen K, et al. Neratinib overcomes trastuzumab resistance in HER2 amplified breast cancer. Oncotarget 2013; 4(10): 1592.
22. Reif J S, Dunn K, Ogilvie G K, Harris C K. Passive smoking and canine lung cancer risk. Am J Epidemiol 1992; 135(3): 234-9 doi 10.1093/oxfordjournals.aje.a116276.
23. Couraud S, Debieuvre D, Moreau L, Dumont P, Margery J, Quoix E, et al. No impact of passive smoke on the somatic profile of lung cancers in never-smokers. Eur Respir J 2015; 45(5): 1415-25 doi 10.1183/09031936.00097314.
24. Bettini G, Morini M, Marconato L, Marcato P S, Zini EJTVJ. Association between environmental dust exposure and lung cancer in dogs. 2010; 186(3): 364-9.
25. Campbell J D, Alexandrov A, Kim J, Wala J, Berger A H, Pedamallu C S, et al. Distinct patterns of somatic genome alterations in lung adenocarcinomas and squamous cell carcinomas. 2016; 48(6): 607.
26. Nik-Zainal S, Wedge D C, Alexandrov L B, Petljak M, Butler A P, Bolli N, et al. Association of a germline copy number polymorphism of APOBEC3A and APOBEC3B with burden of putative APOBEC-dependent mutations in breast cancer. 2014; 46(5): 487.
27. Errani C, Zhang L, Sung Y S, Hajdu M, Singer S, Maki R G, et al. A novel WWTR1-CAMTA1 gene fusion is a consistent abnormality in epithelioid hemangioendothelioma of different anatomic sites. 2011; 50(8): 644-53.
28. Gao J, Aksoy B A, Dogrusoz U, Dresdner G, Gross B, Sumer S O, et al. Integrative analysis of complex cancer genomics and clinical profiles using the cBioPortal. 2013; 6(269): pl1-pl.
29. Weinstein J N, Collisson E A, Mills G B, Shaw K R M, Ozenberger B A, Ellrott K, et al. The cancer genome atlas pan-cancer analysis project. 2013; 45(10): 1113.
30. Mazieres J, Peters S, Lepage B, Cortot A B, Barlesi F, Beau-Faller M, et al. Lung cancer that harbors an HER2 mutation: epidemiologic characteristics and therapeutic perspectives. J Clin Oncol 2013; 31(16): 1997-2003 doi 10.1200/JCO.2012.45.6095.
31. Mazieres J, Barlesi F, Filleron T, Besse B, Monnet I, Beau-Faller M, et al. Lung cancer patients with HER2 mutations treated with chemotherapy and HER2-targeted drugs: results from the European EUHER2 cohort. Ann Oncol 2016; 27(2): 281-6 doi 10.1093/annonc/mdv573.
32. Shigematsu H, Takahashi T, Nomura M, Majmudar K, Suzuki M, Lee H, et al. Somatic mutations of the HER2 kinase domain in lung adenocarcinomas. Cancer Research 2005; 65(5): 1642-6.
33. Kanika Bajaj Pahuja T T N, Bijay S. Jaiswal, Kumar Prabhash, Tarjani M. Thaker, Kate Senger S C, Noelyn M. Kljavin, Aju Antony, Sameer Phalke, Prasanna Kumar, Marco Mravic, Eric W. Stawiski, Derek Vargas, Steffen Durinck, Ravi Gupta, Arati Khanna-Gupta, Sally E. Trabucco, Ethan S. Sokol, Ryan J. Hartmaier, Ashish Singh, Anuradha Chougule, Vaishakhi Trivedi, Amit Dutt, Vijay Patil, Amit Joshi, Vanita Noronha, James Ziai, Sripad D. Banavali, Vedam Ramprasad, William F. DeGrado, Raphael Bueno, Natalia Jura, and Somasekar Seshagiri. Actionable Activating Oncogenic ERRB2/HER2 Transmembrane and Juxtamembrane DomainMutations. Cancer Cell 2018(34): 15.
34. Takezawa K, Pirazzoli V, Arcila M E, Nebhan C A, Song X, de Stanchina E, et al. HER2 amplification: a potential mechanism of acquired resistance to EGFR inhibition in EGFR-mutant lung cancers that lack the second-site EGFRT790M mutation. Cancer discovery 2012.
35. Pellegrini C, Falleni M, Marchetti A, Cassani B, Miozzo M, Buttitta F, et al. HER-2/Neu alterations in non-small cell lung cancer: a comprehensive evaluation by real time reverse transcription-PCR, fluorescence in situ hybridization, and immunohistochemistry. Clinical cancer research 2003; 9(10): 3645-52.
36. Rouquette I, Lauwers-Cances V, Allera C, Brouchet L, Milia J, Nicaise Y, et al. Characteristics of lung cancer in women: importance of hormonal and growth factors. Lung Cancer 2012; 76(3): 280-5.
37. Langer C J, Stephenson P, Thor A, Vangel M, Johnson D H. Trastuzumab in the treatment of advanced non-small-cell lung cancer: is there a role? Focus on Eastern Cooperative Oncology Group study 2598. Journal of clinical oncology 2004; 22(7): 1180-7.
38. Lara Jr P N, Laptalo L, Longmate J, Lau D H, Gandour-Edwards R, Gumerlock P H, et al. Trastuzumab plus Docetaxel in HER2/neu-Positive Non-Small-Cell Lung Cancer: A California Cancer Consortium Screening and Phase I I Trial. Clinical lung cancer 2004; 5(4): 231-6.
39. Bargmann C I, Hung M C, Weinberg R A. Multiple independent activations of the neu oncogene by a point mutation altering the transmembrane domain of p185. Cell 1986; 45(5): 649-57.
40. Gama A, Alves A, Schmitt FJVA. Identification of molecular phenotypes in canine mammary carcinomas with clinical implications: application of the human classification. 2008; 453(2): 123-32.
41. Mason N J, Gnanandarajah J S, Engiles J B, Gray F, Laughlin D, Gaurnier-Hausser A, et al. Immunotherapy with a HER2-targeting listeria induces HER2-specific immunity and demonstrates potential therapeutic effects in a phase I trial in canine osteosarcoma. 2016; 22(17): 4380-90.
42. Vermeer P D, Einwalter L A, Moninger T O, Rokhlina T, Kern J A, Zabner J, et al. Segregation of receptor and ligand regulates activation of epithelial growth factor receptor. Nature 2003; 422(6929): 322-6 doi 10.1038/nature01440.
43. Yatabe Y, Kerr K M, Utomo A, Rajadurai P, Tran V K, Du X, et al. EGFR mutation testing practices within the Asia Pacific region: results of a multicenter diagnostic survey. J Thorac Oncol 2015; 10(3): 438-45 doi 10.1097/JTO.0000000000000422.
44. Shigematsu H, Lin L, Takahashi T, Nomura M, Suzuki M, Wistuba, I I, et al. Clinical and biological features associated with epidermal growth factor receptor gene 45. Shi Y, Au J S, Thongprasert S, Srinivasan S, Tsai C M, Khoa M T, et al. A prospective, molecular epidemiology study of EGFR mutations in Asian patients with advanced non-small-cell lung cancer of adenocarcinoma histology (PIONEER). J Thorac Oncol 2014; 9(2): 154-62 doi 10.1097/JTO.0000000000000033.
46. Nie K, Jia Y, Zhang XJTB. Cell-free circulating tumor DNA in plasma/serum of non-small cell lung cancer. 2015; 36(1): 7-19.
47. Jiang T, Ren S, Zhou CJLC. Role of circulating-tumor DNA analysis in non-small cell lung cancer. 2015; 90(2): 128-34.
48. Kwapisz DJAotm. The first liquid biopsy test approved. Is it a new era of mutation testing for non-small cell lung cancer? 2017; 5(3).
49. Wu Y-L, Zhou C, Liam C-K, Wu G, Liu X, Zhong Z, et al. First-line erlotinib versus gemcitabine/cisplatin in patients with advanced EGFR mutation-positive non-small-cell lung cancer: analyses from the phase III, randomized, open-label, ENSURE study. 2015; 26(9): 1883-9.
50. Singer J, Weichselbaumer M, Stockner T, Mechtcheriakova D, Sobanov Y, Bajna E, et al. Comparative oncology: ErbB-1 and ErbB-2 homologues in canine cancer are susceptible to cetuximab and trastuzumab targeting. Molecular immunology 2012; 50(4): 200-9.
51. Gordon I, Paoloni M, Mazcko C, Khanna C. The Comparative Oncology Trials Consortium: using spontaneously occurring cancers in dogs to inform the cancer drug development pathway. PLOS medicine 2009; 6(10): e1000161.
52. Murtaza M D S, Pogrebniak K, Rueda O M, Provenzano E, Grant J, Chin S F, Tsui D W, Marass F, Gale D, Ali H R, Shah P, Contente-Cuomo T, Farahani H, Shumansky K, Kingsbury Z, Humphray S, Bentley D, Shah S P, Wallis M, Rosenfeld N, Caldas C. Multifocal clonal evolution characterized using circulating tumour DNA in a case of metastatic breast cancer. Nat Commun 2015; 4(6): 8760.
53. Li H, Handsaker B, Wysoker A, Fennell T, Ruan J, Homer N, et al. The Sequence Alignment/Map format and SAMtools. Bioinformatics 2009; 25(16): 2078-9 doi 10.1093/bioinformatics/btp352.
54. Hsu W L, Huang H M, Liao J W, Wong M L, Chang S C. Increased survival in dogs with malignant mammary tumours overexpressing HER-2 protein and detection of a silent single nucleotide polymorphism in the canine HER-2 gene. Veterinary Journal 2009; 180 (1): 116-23 doi 10.1016/j.tvjl.2007.10.013.

What is claimed is:

1. A method of treating lung cancer in a canine subject, comprising the steps of:
   receiving a biological sample from the subject;
   analyzing the biological sample for one or more missense mutations in HER2, wherein the one or more missense mutations in HER2 comprises V659E, A664T and/or K676E;
   and treating the subject with an inhibitor of HER2 if the one or more missense mutations is present.

2. The method of claim 1, wherein the HER2 inhibitor is selected from the group comprising trastuzumab, neratinib, lapatinib, erlotinib, and pertuzumab.

3. The method of claim 1, wherein the lung cancer is canine pulmonary adenocarcinoma.

4. The method of claim 1, wherein the biological sample is a tumor sample or a plasma sample.

5. The method of claim 4, wherein cell-free tumor DNA (ctDNA) from plasma is analyzed.

6. The method of claim 1, wherein the analyzing step comprises subjecting the biological sample to amplicon and/or exome sequencing.

7. A method of treating lung cancer in a canine subject, comprising the steps of:
   receiving a biological sample from the subject;
   adding to a mixture comprising the biological sample a first primer consisting of SEQ ID NO: 1 and a second primer consisting of SEQ ID NO: 2;
   subjecting the mixture to conditions that allow nucleic acid amplification;
   detecting in the amplified nucleic acid the presence of a HER2 V659E missense mutation; and
   treating the subject with an inhibitor of HER2 if the HER2 V659E missense mutation is present.

8. The method of claim 7, wherein the detecting step comprises sequencing a product of the nucleic acid amplification.

9. The method of claim 7, wherein the HER2 inhibitor is selected from the group comprising trastuzumab, neratinib, lapatinib, erlotinib, and pertuzumab.

10. The method of claim 7, further comprising adding to the mixture a probe consisting of SEQ ID NO: 3.

11. The method of claim 10, wherein the lung cancer is canine pulmonary adenocarcinoma.

12. The method of claim 7, wherein the biological sample is a tumor sample or a plasma sample.

13. The method of claim 12, wherein cell-free tumor DNA (ctDNA) from plasma is analyzed.

14. A method of treating lung cancer in a canine subject, comprising the steps of:
   receiving a biological sample from the subject;
   analyzing the biological sample for one or more missense mutations selected from the group consisting of HER2 V659E, HER2 A664T, and HER2 K676E, and one or more missense mutations selected from the group consisting of KRAS G12D/V, SMAD4 D351Y/G, and TP53 R239Q/G;
   and administering, if one or more of the HER2 mutations is present, a therapeutically effective amount of a pharmaceutical composition selected from the group consisting of trastuzumab, neratinib, lapatinib, erlotinib, and pertuzumab.

15. The method of claim 14, wherein the analyzing step comprises subjecting the biological sample to amplicon and/or exome sequencing.

16. The method of claim 14, wherein the lung cancer is canine pulmonary adenocarcinoma.

17. The method of claim 14, wherein the biological sample is a tumor sample or a plasma sample.

18. The method of claim 17, wherein cell-free tumor DNA (ctDNA) from plasma is analyzed.

\* \* \* \* \*

SEQUENCE LISTING

<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
cccacgacca cagcca                                               16

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ccctgtgaca tccatcattg c                                         21

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
cagaatgccc wccacagc                                             18

<210> SEQ ID NO 4
<211> LENGTH: 21
<212> TYPE: DNA
<213> ORGANISM: Artificial Sequence
<220> FEATURE:
<223> OTHER INFORMATION: Primer

```
<400> SEQUENCE: 4
catctgcacc attgatgtct a                                          21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggcccaagtc ttcattctga                                            20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6 gcagcccccag cgtcgtgatt                                           20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
catctcgagc aagccgctca gt                                         22
```